(12) United States Patent
Lagrone et al.

(10) Patent No.: US 12,198,243 B2
(45) Date of Patent: *Jan. 14, 2025

(54) ONLINE INTERACTIVE PLATFORM WITH MOTION DETECTION

(71) Applicant: TuringSense Inc., Santa Clara, CA (US)

(72) Inventors: Wade I. Lagrone, Santa Clara, CA (US); Edwin Angkasa, Santa Clara, CA (US); Bullit Sesariza, Forli (IT); Indra Madyasiwi, Santa Clara, CA (US); Ali Alhabsyi, Oakland, CA (US); Cecylia Wati, Santa Clara, CA (US); Joseph Chamdani, Santa Clara, CA (US)

(73) Assignee: Turingsense Inc., Santa Clara, CA (US)

( * ) Notice: Subject to any disclaimer, the term of this patent is extended or adjusted under 35 U.S.C. 154(b) by 16 days.

This patent is subject to a terminal disclaimer.

(21) Appl. No.: 18/211,280

(22) Filed: Jun. 18, 2023

(65) Prior Publication Data

US 2024/0135617 A1  Apr. 25, 2024

Related U.S. Application Data

(63) Continuation of application No. 17/729,742, filed on Apr. 26, 2022, now Pat. No. 11,682,157, which is a (Continued)

(51) Int. Cl.
*G06T 13/40* (2011.01)
*G06F 3/01* (2006.01)

(52) U.S. Cl.
CPC .............. *G06T 13/40* (2013.01); *G06F 3/011* (2013.01); *G06F 3/014* (2013.01); *G06F 3/017* (2013.01)

(58) Field of Classification Search
CPC .......... G06T 13/40; G06F 3/011; G06F 3/012; G06F 3/014; G06F 3/015; G06F 3/017; (Continued)

(56) References Cited

U.S. PATENT DOCUMENTS 10,157,488 B2 * 12/2018 Chamdani ............... G06F 3/017
10,304,230 B2 *  5/2019 Chamdani ............... G06F 3/014
(Continued)

*Primary Examiner* — Vijay Shankar
(74) *Attorney, Agent, or Firm* — Joe Zheng

(57) ABSTRACT

Techniques for a motion-based online interactive platform are described. The platform makes a motion-based online class realistic and allows a teacher to visualize motions performed by a student in a perspective and how close the motion is in view of an authoritative instructor (model). Each of computing devices used respectively by students is coupled to or includes a camera, where the camera is used by a student to show his/her presence or poses he/she performs. Data streams from the computing devices are received in a control computer associated with the teacher, where each of the data streams includes a video and a set of sensing data. A 3D avatar of a student is generated from the sensing data in the control computer and may be shown alone or along with an avatar of an instructor or model to visualize any differences between the student and the model in reference to a pose or motion.

20 Claims, 54 Drawing Sheets

Related U.S. Application Data continuation-in-part of application No. 16/687,635, filed on Nov. 18, 2019, now Pat. No. 11,321,894, which is a continuation of application No. 16/423,130, filed on May 27, 2019, now Pat. No. 10,672,173, which is a continuation of application No. 16/219,727, filed on Dec. 13, 2018, now Pat. No. 10,304,230, which is a continuation of application No. 15/271,205, filed on Sep. 20, 2016, now Pat. No. 10,157,488.

(60) Provisional application No. 62/221,502, filed on Sep. 21, 2015.

(58) Field of Classification Search
CPC .. G06F 18/251; G06F 2218/12; A63F 13/213; A63F 13/428; A63F 13/655; A63F 13/816; G09B 19/0038; G06V 10/95; G06V 20/20; G06V 20/42; G06V 40/23; G16H 20/30; G16H 40/63; G16H 50/30; G16H 80/00; G16H 40/67; G16H 50/70; A61B 2503/12; A61B 2505/09; A61B 2560/0238; A61B 5/1122; A61B 5/1123; A61B 5/6804; A61B 5/744; A61B 5/0022
See application file for complete search history.

(56) References Cited

U.S. PATENT DOCUMENTS

| | | | |
|---|---|---|---|
| 10,672,173 B2* | 6/2020 | Chamdani | G16H 50/30 |
| 11,321,894 B2* | 5/2022 | Garofalo | G06F 3/017 |
| 11,682,157 B2* | 6/2023 | Lagrone | A63F 13/816 |
| | | | 345/156 |

* cited by examiner

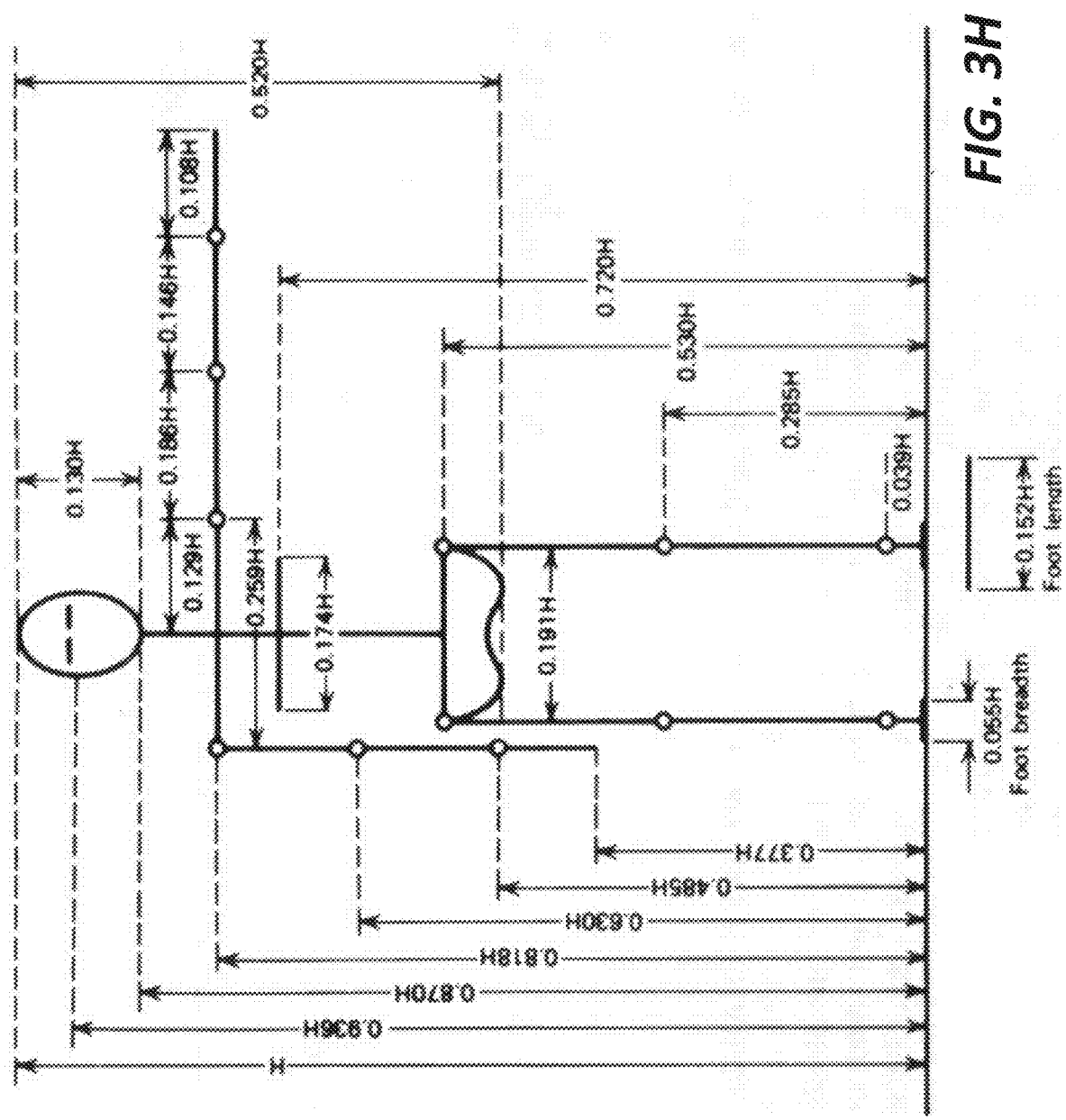

LEFT (a) Grid search algorithm working principle for one body segment (right upper arm): angular grid (in blue), anatomical longitudinal axis (green), mediolateral direction initial guess (red) and refined mediolateral direction (black); RIGHT (b) Cost function over the grid for four body segments left and right upper arm and left and right upper leg

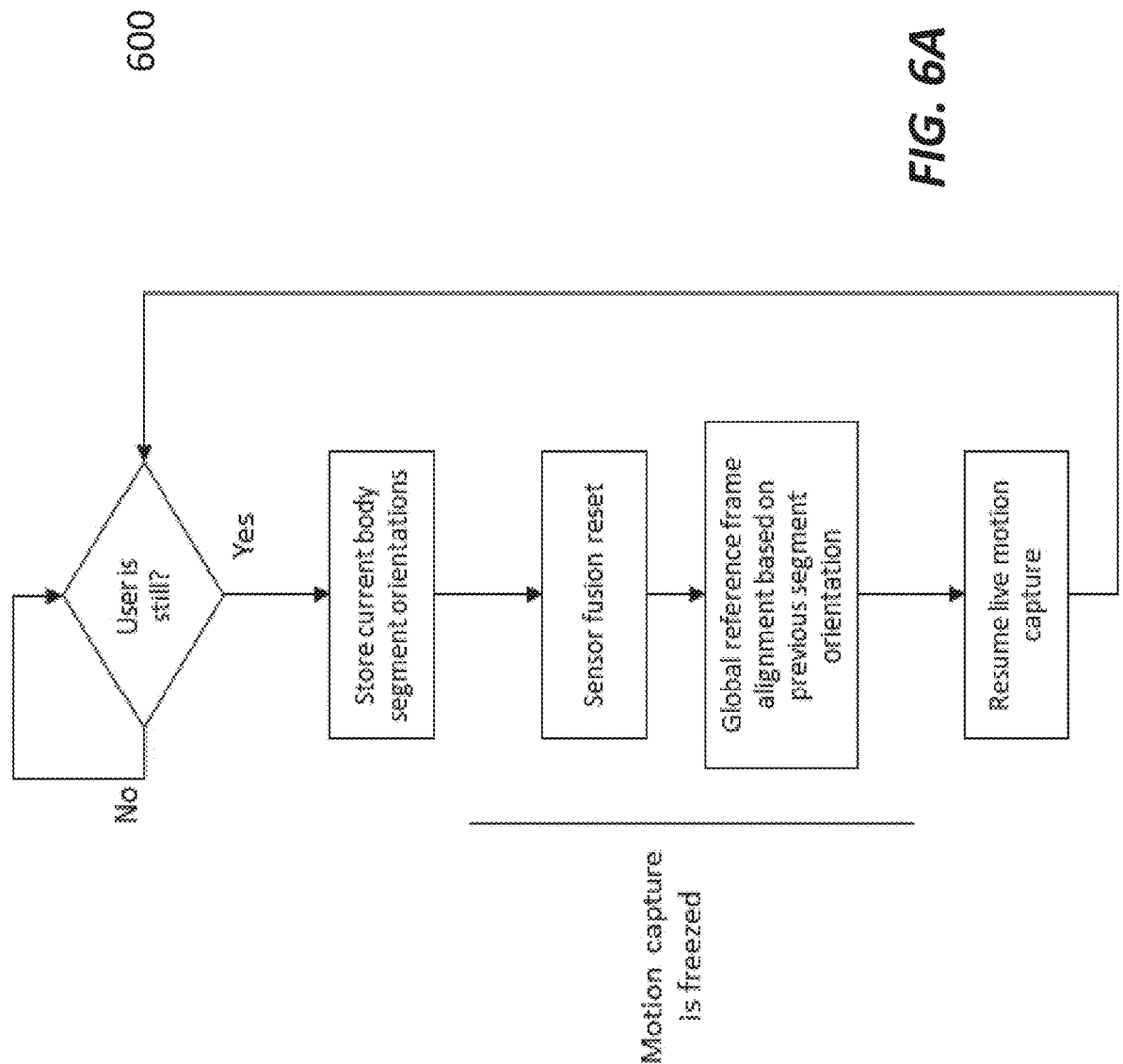

ONLINE INTERACTIVE PLATFORM WITH MOTION DETECTION

CROSS REFERENCE TO RELATED APPLICATIONS

This application is a continuation of U.S. application Ser. No. 17/729,742, entitled "Motion-based online interactive platform", filed on Apr. 26, 2022, now U.S. Pat. No. 11,682,157, which is a continuation of U.S. application Ser. No. 16/687,635, entitled "Motion control via an article of clothing", filed on Nov. 18, 2019, now U.S. Pat. No. 11,321,894, which is a continuation-in-part of U.S. application Ser. No. 16/423,130, entitled "System and method for capturing and analyzing motions to be shared", filed on May 27, 2019, now U.S. Pat. No. 10,672,173, which is a continuation of U.S. application Ser. No. 16/219,727, entitled "System and method for capturing and analyzing motions to render a human avatar animation", filed on Dec. 13, 2018, now U.S. Pat. No. 10,304,230, which claims the priority of U.S. Prov. App. Ser. No. 62/768,967, entitled "Motion control based on artificial intelligence", filed on Nov. 18, 20118, and a continuation of U.S. application Ser. No. 15/271,205, entitled "System and method for capturing and analyzing motions", filed on Sep. 20, 2016, now U.S. Pat. No. 10,157,488, which claims the priority of U.S. Prov. App. Ser. No. 62/221,502, entitled "System and method for capturing and analyzing complex motions", filed on Sep. 21, 2015. This application also claims the benefits of U.S. provisional application No. 63/181,504, entitled "Motion-based online classes", filed on Apr. 29, 2021, which is hereby incorporated by reference for all purposes.

BACKGROUND OF THE INVENTION

Field of the Invention

The present invention is generally related to motion controls and more particularly related to methods and systems for providing interactive instructions to users based on detection of their respective motions, and more particularly related to a platform to facilitate an instructor to analyze the respective motions and provide various feedback to the users to allow the users to make suggested correct or guided movements.

Related Art

The COVID-19 pandemic, also known as the coronavirus pandemic, is an ongoing global pandemic of coronavirus disease 2019 (COVID-19) has resulted in various schools shut down all across the world. As a result, education has changed dramatically with the distinctive rise of e-learning, whereby teaching is undertaken remotely and on digital platforms. Research suggests that online learning has been shown to increase retention of information, and take less time, meaning the changes coronavirus have caused might be here to stay.

Even before COVID-19, there was already high growth and adoption in education technology, with global edtech investments reaching nearly US$19 Billions in 2019 and the overall market for online education projected to reach $350 Billions by 2025. Whether it is language apps, virtual tutoring, video conferencing tools, or online learning software, there has been a significant surge in usage since COVID-19.

In response to the significant demand, many online learning platforms are offering free or paid access to their services. For example, Tencent classroom has been used extensively since mid-February in 2019 after the government instructed a quarter of a billion full-time students to resume their studies through online platforms. This resulted in the largest "online movement" in the history of education. Other companies are bolstering capabilities to provide a one-stop shop for teachers and students. For example, Lark, a Singapore-based collaboration suite initially developed by ByteDance, as an internal tool to meet its own exponential growth, began offering teachers and students unlimited video conferencing time, auto-translation capabilities, real-time co-editing of project work, and smart calendar scheduling, amongst other features. To do so quickly and in a time of crisis, Lark ramped up its global server infrastructure and engineering capabilities to ensure reliable connectivity.

Some school districts in United States are forming unique partnerships, like the one between The Los Angeles Unified School District and PBS SoCal/KCET to offer local educational broadcasts, with separate channels focused on different ages, and a range of digital options. Media organizations such as the BBC are also powering virtual learning; Bitesize Daily, launched in April 2019, is offering 14 weeks of curriculum-based learning for kids across the UK with celebrities like Manchester City footballer Sergio Aguero teaching some of the content.

All these efforts are focused on how to convey or exchange knowledge from one side to another side or among all sides, requiring no or minimum physical motions in the knowledge sharing online. When coming to learning or sharing various movements online, for example, yoga, dancing and sporting, the current edtech tools are inadequate. Given the current display technologies, 3D movements in these types of learning are essentially projected onto a 2D display, any fine movements along one dimension would be lost in the 2D display. For example, an instructor facing a camera makes a leg backward movement, how much the movement has been made would not be clearly displayed in the 2D display or viewed clearly by the students unless the camera is moved, for example, 90 degrees. Likewise, the instructor would not be able to see any error in the leg movement by a student. It is also true in learning golf swinging with a trainer. A trainee/trainer would not be able to see how much the upper body of the trainer/trainee spins out unless the camera goes around or a second 2D view is timely provided. Even if a second or more cameras are provided, it is not convenient for the trainer/trainee to follow the actual move or notice the difference in movements. Accordingly, there is a strong need for techniques to capture the full motion and share any differences immediately between the movements made by a trainer and a trainee.

Today, wearable technology is on the rise in personal and business use. For example, in sports and fitness, wearable technology has applications in monitoring and real-time feedback. The decreasing cost of processing power and other components is encouraging widespread adoption and availability. However, the known technology is limited in its ability to provide useful analysis and high-speed algorithms. There is thus another need for techniques to better present movements in 3D to 2D displays.

SUMMARY OF THE INVENTION

This section is for the purpose of summarizing some aspects of the present invention and to briefly introduce some preferred embodiments. Simplifications or omissions may be made to avoid obscuring the purpose of the section. Such simplifications or omissions are not intended to limit the scope of the present invention.

In general, the present invention is related to capturing and analyzing complex motions performed by a person according to an activity (e.g., a sport, an exercise or dance). According to one aspect of the present invention, a platform is provided to demonstrate 3D postures effectively on a 2D display screen, allow an instructor to examine various movements of each or all of trainees performing a set of complex motions in accordance of a standard, and demonstrate ways how to correct certain moves to the standard.

According to another aspect of the present invention, modular sensing devices or sensor modules are attached to different parts of a body of a user or trainer. As the person makes moves, the sensor modules, each including at least one inertial sensor, producing sensing data that are locally received in one module in communication with an external device either remotely or locally. Relying on the resources on the external device, the combined sensing data received from these sensor modules are processed and analyzed to derive the motions in a 3D space made the person. Depending on implementation, the external device is a computing device that may be a mobile device, a server or a part of servers (a.k.a., cloud computing).

According to still another aspect of the present invention, a motion-based online interactive platform is proposed. Depending on implementation, the platform may be implemented as an application, a Teacher App or a student App. Each may be executed in a computer or control computer associated with an instructor or teacher or computing devices associated with students. Each of the computing devices is coupled to or includes a camera, where the camera is used by a student to show his presence or poses he performs. Data streams from the computing devices are received in the control computer, where each of the data streams includes a video and a set of sensing data. A 3D avatar of a student is generated from the sensing data in the control computer. The video is not used for generating the avatar. The avatar may be shown alone or along with an avatar of an instructor or model to visualize any differences between the student and the model in reference to a pose or motion. A corresponding matching score may be conducted to show how close the student has performed in view of the model.

According to still another aspect of the present invention, the platform allows a viewer (e.g., an instructor or teacher in a class) to view or share the avatar or the avatars in a perspective with the student or the class, where the avatars are superimposed on top of each other to highlight the differences between the student and the model in reference to a pose or motion.

According to still another aspect of the present invention, the platform facilitates automatic control on the control computer of the plurality of computing devices according to different modes of a class. The exemplary control includes mute or unmute of mics in the computing devices when an online class enters a predefined mode of the class. The control computer also sends out a periodic signal (heartbeat) to the computing devices to facilitate the synchronization of the displays on all computers.

According to still another aspect of the present invention, a cloud architecture, design, or implementation is provided with features to support real-time sensor data streaming from thousands of users simultaneously, compute-intensive sensor/motion processing with milliseconds latency, streaming back to a client device for 3D motion animation/analysis, synchronization of user metadata, motion library and session recordings, instant playback of current/previous recording, remote coaching/viewing/broadcast, and sharing one's motions with one or more other users. According to still another aspect of the present invention, 3D graphics animation is provided with features to compare reference motion vs. actual motion having continuous and/or multi-pose motion, shadow train with imitation game, live on-court train with instant audio feedback, and materialize real movement of an object held in a user hand (e.g., tennis racquet).

According to still another aspect of the present invention, a motion library is provided with features to allow users to store reference motions trimmed from recorded motions, select a motion to setup a specific lesson and train on-court with instant audio feedback, select a motion to imitate in a shadow motion game, share a library with a group of users (e.g., tennis academy group), and immortalize and monetize motions of elite pros/users.

According to still another aspect of the present invention, a wearable system is architected for many applications involving motions, wherein the system is designed for analyzing complex motions by one or more persons in areas, such as, sports, ARNR, healthcare, and etc. The system is applicable or modified uniquely for each target application. This application-oriented approach provides a more efficient and accurate design.

According to yet another aspect of the present invention, the system can be a camera-less, full-body motion capture and motion analysis product built specifically for a sport (e.g., tennis). A wireless and portable device provides instant biomechanics feedback for technique optimization and injury prevention. Scalable, cloud-based technology enables users to store and share session data in real-time with coaches, friends and family anywhere in the world via a mobile application (App), as well as compare a user's technique versus reference players (including pros) in a stored motion library.

The present invention may be implemented as a system, a part of a system, a method, a process or a product. Different embodiments may yield different advantages, benefits or objectives. It is believed that various implementations may lead to results that may not be achieved conventionally. According to one embodiment, the present invention is a method for instructing a class online, the method comprising receiving in an instructor or control computer data streams from computing devices respectively associated with students performing poses in accordance with a predefined activity, wherein each of the streams includes a video recording a student and sensing data from a plurality of sensor modules disposed respectively to designated body parts of the student. The method further comprises deriving attributes from the sensing data to generate an avatar of the student; and displaying on the control computer the avatar in a chosen perspective while the student performs the poses.

According to another embodiment, the present invention is a computer comprising: a display screen, a memory space for storing code, a processor coupled to the memory space and executing the code to cause the computer to perform operations of: receiving streams from computing devices remotely located and respectively associated with students performing poses in accordance with a predefined activity, wherein each of the streams includes a video recording a student performing the poses and sensing data from a plurality of sensor modules disposed respectively to designated body parts of the student. The operations further comprise deriving attributes from the sensing data to generate an avatar of the student; and displaying on the display screen the avatar in a chosen perspective while the student performs the poses.

BRIEF DESCRIPTION OF THE DRAWINGS

Throughout this document, drawings are provided to illustrate various embodiments of the invention. Reference numbers may be re-used to indicate correspondence between referenced elements. The drawings are provided to illustrate example embodiments described herein and are not intended to limit the scope of the disclosure.

FIG. 3H shows that the length of all body segments can be approximated as a ratio of user height (H);

FIG. 6A shows a workflow or process of soft pose reset;

FIG. 8F shows a view by a teacher that includes what is referred herein as auto-student;

FIG. 8G shows the teacher has switched to the avatar view of the auto-student;

FIG. 8O shows an exemplary snapshot of a student for a predefined period (e.g., last 12 weeks);

DETAILED DESCRIPTION OF THE PREFERRED EMBODIMENTS

Figure 1A:
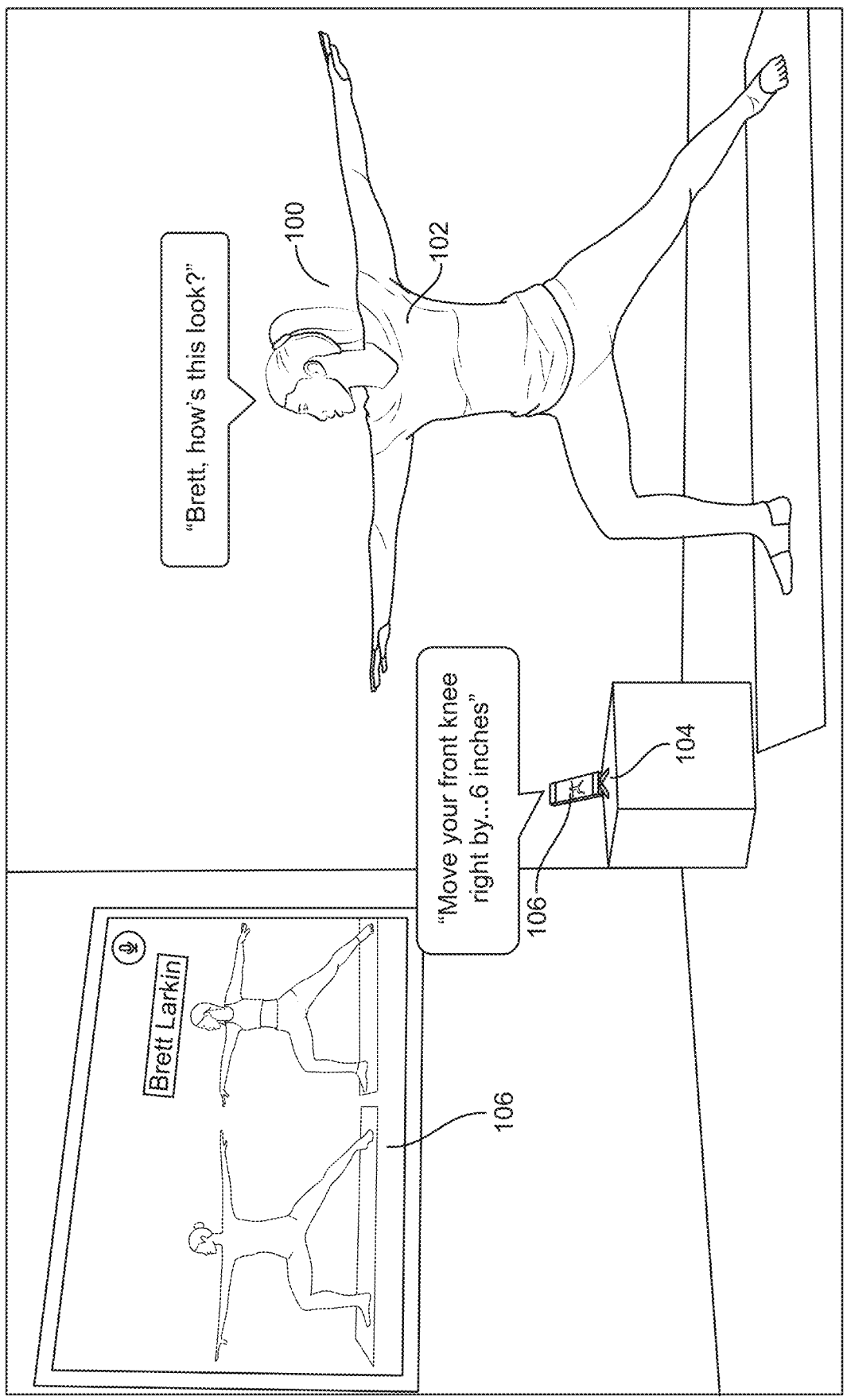
FIG. 1A shows an exemplary configuration in which a user 100 in specially-designed shirt and pants performs a pose or certain motions according to one embodiment of the present invention.

The detailed description of the present invention is presented largely in terms of procedures, steps, logic blocks, processing, or other symbolic representations that directly or indirectly resemble the operations of data processing devices. These descriptions and representations are typically used by those skilled in the art to most effectively convey the substance of their work to others skilled in the art. Numerous specific details are set forth in order to provide a thorough understanding of the present invention. However, it will become obvious to those skilled in the art that the present invention may be practiced without these specific details. In other instances, well known methods, procedures, components, and circuitry have not been described in detail to avoid unnecessarily obscuring aspects of the present invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments.

The present invention pertains to a system, a method, a platform and an application each of which is uniquely designed, implemented or configured to use distributed placement of sensor modules for capturing and analyzing motions of a human being performing various activities (e.g., per a sport). In one embodiment, full and/or partial body motion capture and analysis are performed using an application-oriented, multi-sensor, high-speed algorithms and scalable system platform. As used herein, any pronoun references to gender (e.g., he, him, she, her, etc.) are meant to be gender-neutral. Unless otherwise explicitly stated, the use of the pronoun "he", "his" or "him" hereinafter is only for administrative clarity and convenience. Additionally, any use of the singular or to the plural shall also be construed to refer to the plural or to the singular, respectively, as warranted by the context.

One of embodiments in the present invention is to provide an interactive platform for demonstrating 3D postures effectively on a 2D display screen, allowing an instructor to examine various movements of each or all of trainees performing a set of complex motions in accordance of a standard, and demonstrating ways how to correct certain moves to the standard.

According to one embodiment, sensorized electronic garments are used to capture full-body motions performed by a wearer (user) in a 3-dimension space (3D), where the motions are viewed by a trainer or an instructor to give real-time coaching feedback to the user to correct his moves or poses. The instructor may be remotely located. With the technologies to be disclosed herein, human motions can be readily digitized into 3D data without using cameras and used for all kinds of creative 3D motion applications in sports, healthcare, AR/VR/gaming, and etc. For example, Yoga is an exemplary sport/exercise application that may practice one embodiment of the present invention. One of the advantages, benefits and objectives in the present invention is to help user learn quickly how to move or pose properly in fitness, golf, tennis, soccer, dance, physical therapy rehabilitation, and etc.

Yoga will be used as an example or exemplary sport to facilitate the description of the present invention. A system providing Yoga employing one embodiment of the present invention is herein referred to as PIVOT Yoga herein. According to one embodiment, PIVOT Yoga is a system, a method, an apparatus or a part of system, wherein PIVOT Yoga includes at least two elements. 1. An article of clothing or garment (a.k.a., eGarment), worn by a yoga practitioner, is embedded with a plurality of (digital) sensors that observe and transmit the angles and relative positions of body parts of the user in real time and 3D space to an external device (e.g., a computing device or smartphone). 2. A program or (mobile) application, executed in the external device, is designed to receive, process, and interpret sensor data from the sensor modules, and displays a representation of motions performed by a user. Within the application, the instructor can view the 3D motion of a chosen student, compare the 3D motion with the same performed by a skilled one (e.g., a trainer or instructor). The comparison is shown in avatars in one embodiment, 3D motions performed by two avatars respectively representing the user and the skilled one.

FIG. 1A shows an exemplary configuration in which a user 100 in specially-designed shirt and pants 102 performs a pose or certain motions according to one embodiment of the present invention. As further described below, the shirt and pants 102 include a plurality of sensor modules (preferably not visible), each being affixed to a designated location, preferably inside, of the clothing 102. With a designated App executing in a portable device 104 (iPhone or wearable device), the user 100 (i.e., a wearer of the clothing 102) can view on a display 106 how she is performing a pose (motion), sees demonstration of a trainer and receives instructions from her trainer.

Subject to a preference, the user 100 may place such an exemplary device 104 anywhere as long as it can maintain communication with the sensors in the clothing 102. A display 106 may be shown from the device 104 or on a larger screen (e.g., via Chromcast). The user 100 may choose a yoga routine from a list of activities in the App executed in the portable device 104, and then proceed with the routine. As will be further detailed below, the user 100 may further choose an instructor or teacher from a list of available instructors to guide her exercise, where the chosen instructor may be asked for feedback for each pose or motion the user 100 has just performed. In one embodiment, the portable device 104 may provide verbal instructions from the chosen instructor or show a video, where the user may control the video in various ways, e.g., voice command or taping on some body parts, and at any point during a pose, ask for comparison between the motions of herself and the chosen instructor.

Figure 1B:
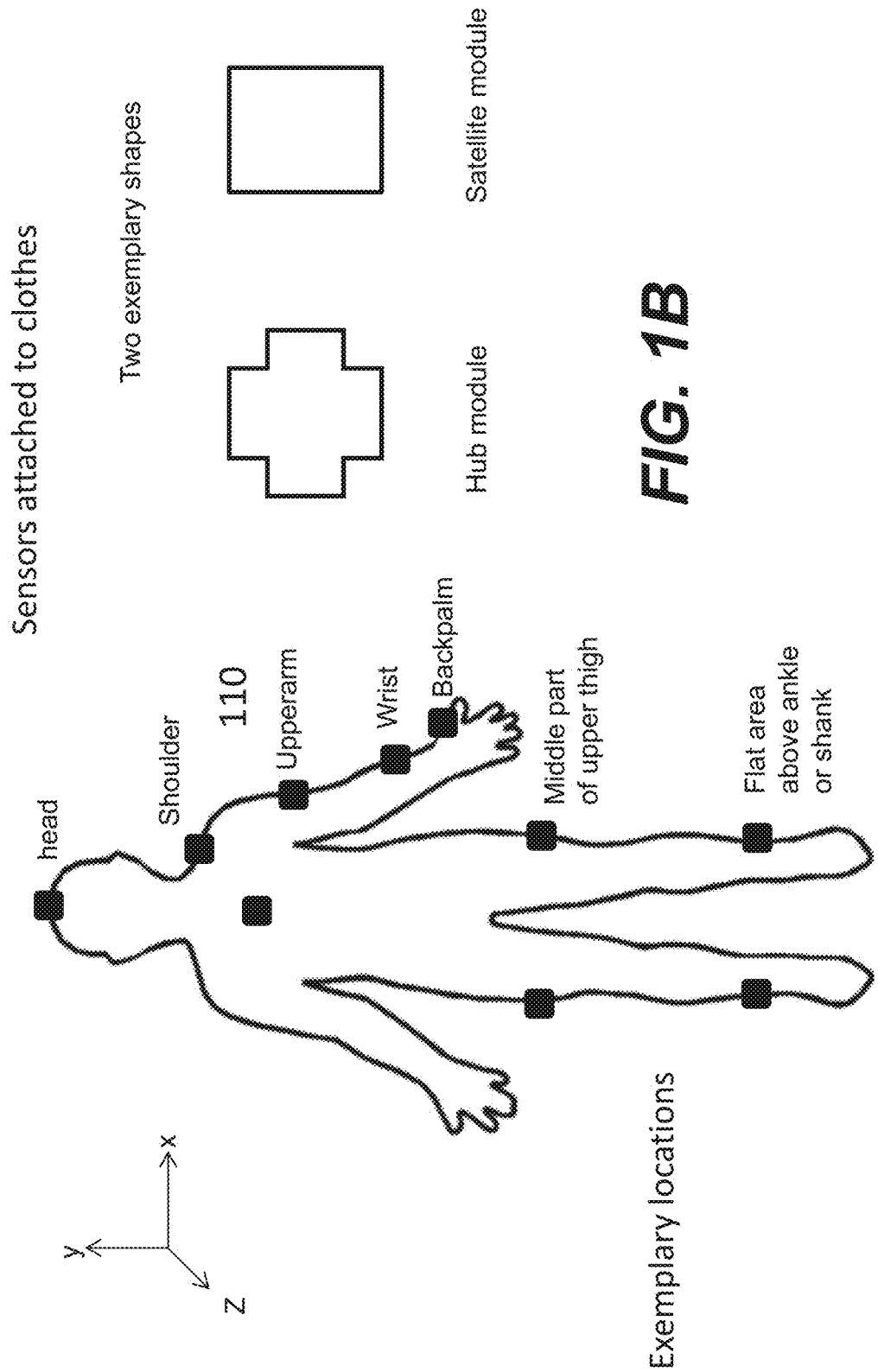
FIG. 1B shows there are a number of sensor devices, sensor modules or simply sensors placed respectively near certain human body parts.

In one embodiment, the user 100 is participating in a class or session coached by an instructor. The instructor sees on his device a group of users performing substantially similar moves, where his device remotely located receives sensor data or 3D data of each of the users. As will be further described below, the instructor can examine how each of the users performs in all perspectives on his 2D display. The instructor can then verbally tell or show a user, for example, which body part to move, in which direction, and how far. FIG. 1B shows there are a number of sensor devices, sensor modules or simply sensors 100 to be placed respectively near certain human body parts. According to one embodiment, these sensors are affixed to respective designated locations within the clothes 102 corresponding to designated human body parts, for example, one sensor is responsible for monitoring a chest, another sensor is responsible for monitoring an upper arm, still another sensor is responsible for monitoring a flat area just above an ankle. Depending on implementation, each of the sensors includes one or more inertial sensors that produce sensing signals when the sensors are caused to move around with the wearer. The sensing signals are sampled periodically (e.g., every 10 millisecond) to produce sensing samples or data.

In one embodiment, the portable device 104 executing an App is caused to receive or collect some or all the sensor samples from the sensors and track every sample point if needed. A system is remotely located with respect to but communicates with the portable device, wherein the system is referred to as a server, a cloud computer or simply cloud, and configured or designed to perform motion analysis by processing a set of raw sensor samples received remotely from one, more or all of the sensors (via the portable device), and derive joint angle outputs to detect start/end of motion, classify a motion type (e.g., forehand topspin, backhand slice, flat serve, etc.) and compute important attributes of the motion (e.g., speed, mass, distance, volume, velocity, acceleration, force, and displacement in scalar or vector). The body segment frames and motion analysis attributes are then sent to a designated App (e.g., Yoga App) running in a mobile device, for 3D graphics rendering into a human avatar, animation and motion chart analysis. Depending on implementation, some or all of the functions in the system may be performed within the portable device 104.

FIG. 1B also shows two exemplary types of the sensor modules, a satellite module and a hub module. For ease of identification in one embodiment, the hub module or hub is designed to have a unique shape, different from the rest of the satellite modules. The hub module is made in a distinct "+" medic shape in one embodiment. In some embodiments, the satellite modules connect wirelessly to a single Hub module, for example, via Wi-Fi, Bluetooth, and etc. In one embodiment, the modules may communicate via a proprietary high-speed 2.4 GHz protocol. For some sport (e.g., tennis), the hub module may be typically disposed near the chest location and is configured to combine the sensor data with the same timestamp and streams, for example, via Wi-Fi or Wi-Fi-Direct to a cloud datacenter or a mobile device (phone, tablet, or laptop). In another embodiment, as will be further described below, the modules may communicate via a communication medium (e.g., conductive threads embedded in an article of clothing).

In one embodiment, each of the satellite modules includes a microcontroller, at least an inertial sensor and a transceiver for intercommunication with the hub module that includes a microcontroller, at least an inertial sensor and a transceiver for intercommunication with the satellite modules and another transceiver for communicating with an external computing device (e.g., the portable device). Each of the sensor modules produces sensing data at a predefined frequency when a user makes moves, the sensing data from the satellite modules are received in the hub module and combined with the sensing data generated within the hub module and transported wirelessly to the external device designed to derive the motion of the user performing activities and facilitate a comparison between the derived motion with stored motion to illustrate a difference between the motion made by the user and motion made by another person.

In another embodiment, each of the satellite modules includes an inertial sensor while the hub module includes a microcontroller, an inertial sensor and an interface for intercommunication with inertial sensors in the satellite modules and a transceiver for communicating with an external computing device (e.g., the portable device). Each of the inertial sensors produces sensing signals when a user makes moves, the sensing signals from the inertial sensors are received in the hub module via a communication medium (e.g., the conductive threads) and combined with the sensing signal generated within the hub module. The sensing signals are sampled at a predefined frequency and transported wirelessly to the external device designed to derive the motion of the user performing activities and facilitate a comparison between the derived motion with stored motion to illustrate a difference between the motion made by the user and motion made by another person.

Figure 1C:
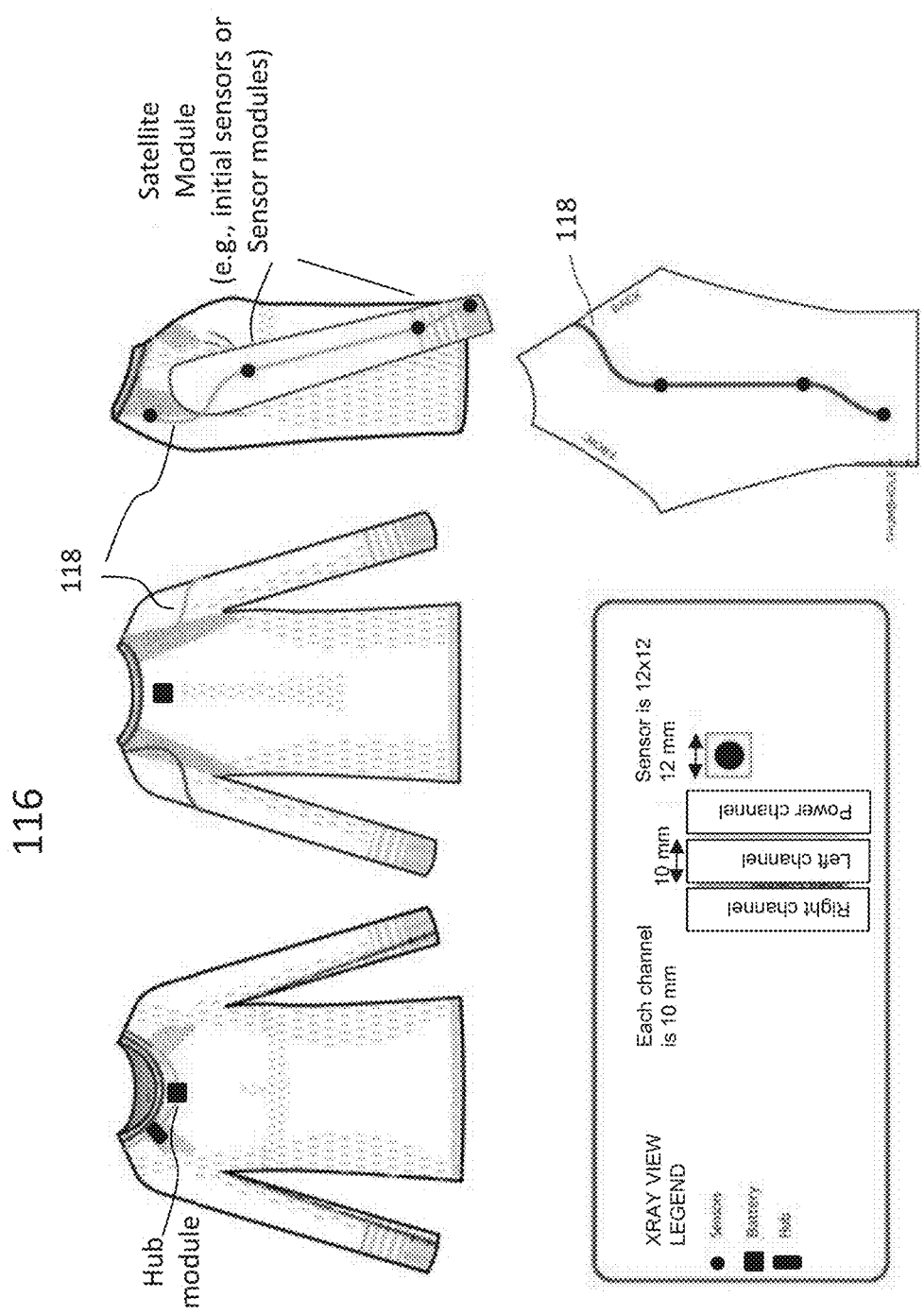
FIG. 1C shows an exemplary layout of locations of the sensors on a long-sleeve shirt.
Figure 1D:
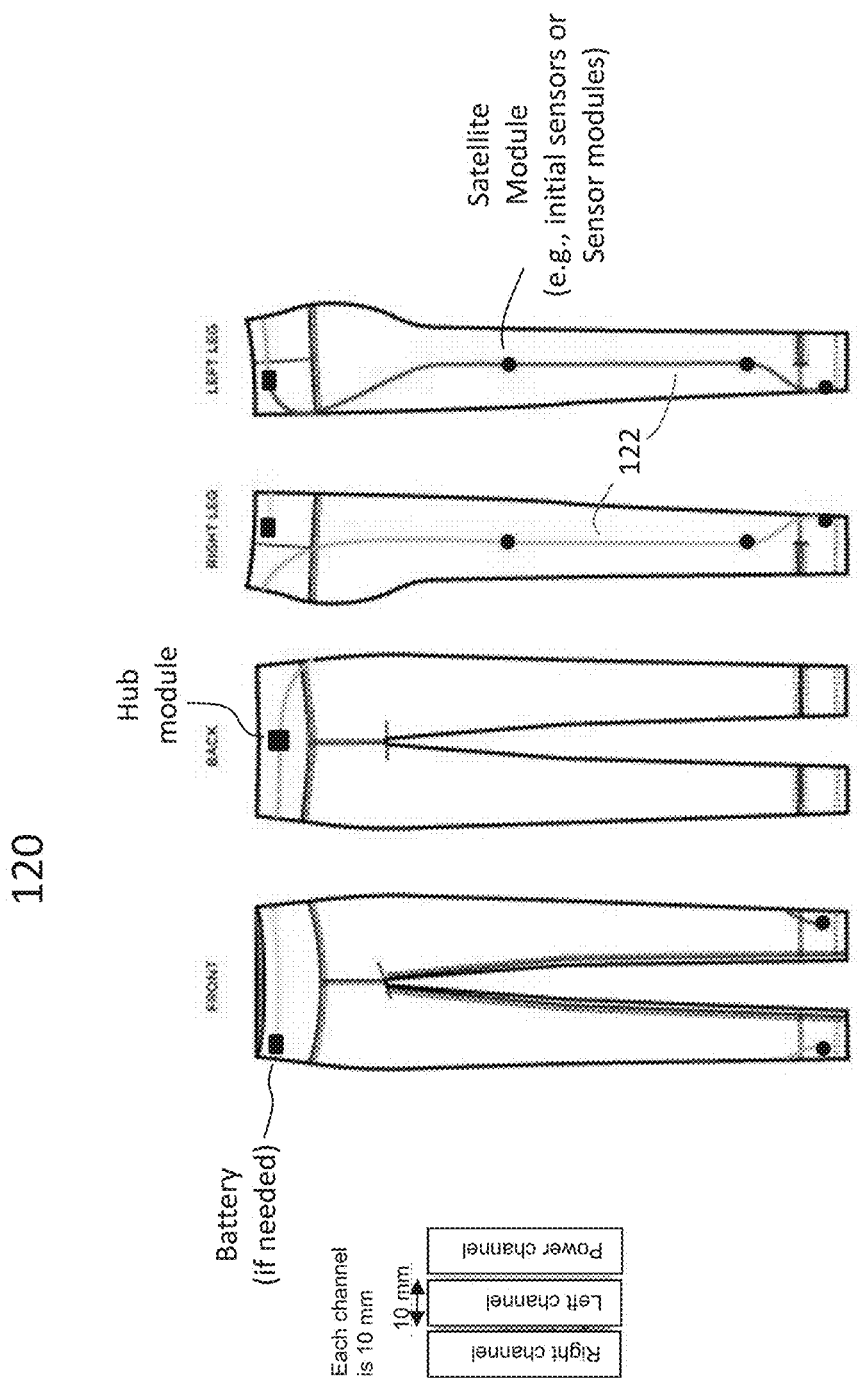
FIG. 1D shows an exemplary layout of locations of the sensors on a pair of pants.

According to one embodiment, an article of clothing, also referred to herein as sensorized eGarments (washable), body motions can be captured and transmitted to an external device so that an authoritative teacher may be engaged to dynamically, in real-time, instruct a user how to improve his motions, for nearly anything from sports to physical therapy. An exemplary sensor module may be, but not limited to, an inertial sensor, such an inertial sensor may be a 9-axis inertial sensor having accelerometer, gyroscope, and magnetometer, or a 6-axis inertial sensor having only accelerometer and gyroscope. Each sensor is placed in a specific location on the inner side of the garment to track the motion of every major limb (bone, body part or body segment). FIG. 1C shows an exemplary layout 116 of locations of the sensors on a long-sleeve shirt, these sensors are located specifically to capture the motion of a particular body part (e.g., a finger or a forearm), where a hub sensor is to be disposed near the chest area of a human body when the shirt is worn. FIG. 1D shows an exemplary layout 120 of locations of the sensors on a pair of pants, these sensors are located specifically to capture the motion of a particular body part (e.g., a knee or an ankle), where a hub sensor is to be disposed near the waist area of a human body. Depending on implementation, one or more batteries (e.g., button batteries) are also embedded in the clothes or enclosed in the sensor modules.

According to one embodiment, a specially designed conductive thread 118 or 122 is used in the clothing to provide connections between batteries and the sensor modules if the batteries are not within each of the sensor modules, and between the hub module and satellite modules. The conductive thread 118 or 122 has textile properties like a regular yarn, composed of low-resistivity (less than 1.5 Ohms per meter) copper core with nano fiber insulation and capable of transmitting high speed electrical signal (up to 10 Mbits per second). In one embodiment, the diameter of the conductive thread 118 or 122 is only 0.32 millimeters. In another embodiment, the conductive thread 118 or 122 goes a zigzag pattern to allow more stretches when needed. When worn, the eGarments look and feel like regular athletic-leisure clothes (athleisure) with the electronics hidden and unfelt.

With the voice capabilities on the portable device, a user is able to pause, resume, skip forward, freeze a video provided by the app. For example, a video or an avatar showing a perfect pose can be paused or repeated, or viewed from different perspectives. The user may ask for feedback while the video of an authoritative teacher is running. Depending on implementation, there are two ways to do this with voice and/or gestures. Without using a wake word, a user, after a one-time setup routine, can simply issue a command within earshot of his phone. The user can issue commands that the system pays attention to as the system is trained to recognize only his voice in one embodiment. As far as the gestures are concerned, since the clothes worn by the user are sensorized, the user may double-tap on various places on his body as a way of controlling the app. In one embodiment, double-tapping on the left hand pauses or resumes the video, double-tapping on the right hand skips to the next chapter in the video, and double-tapping on the chest sensor asks the system for feedback. In another embodiment, a gesture is designed to freeze an avatar in a video. In still another embodiment, one of the sensors (e.g., the one on the waist) is designed to signal a pause of the avatar or feedback of a chosen instructor.

Figure 2:
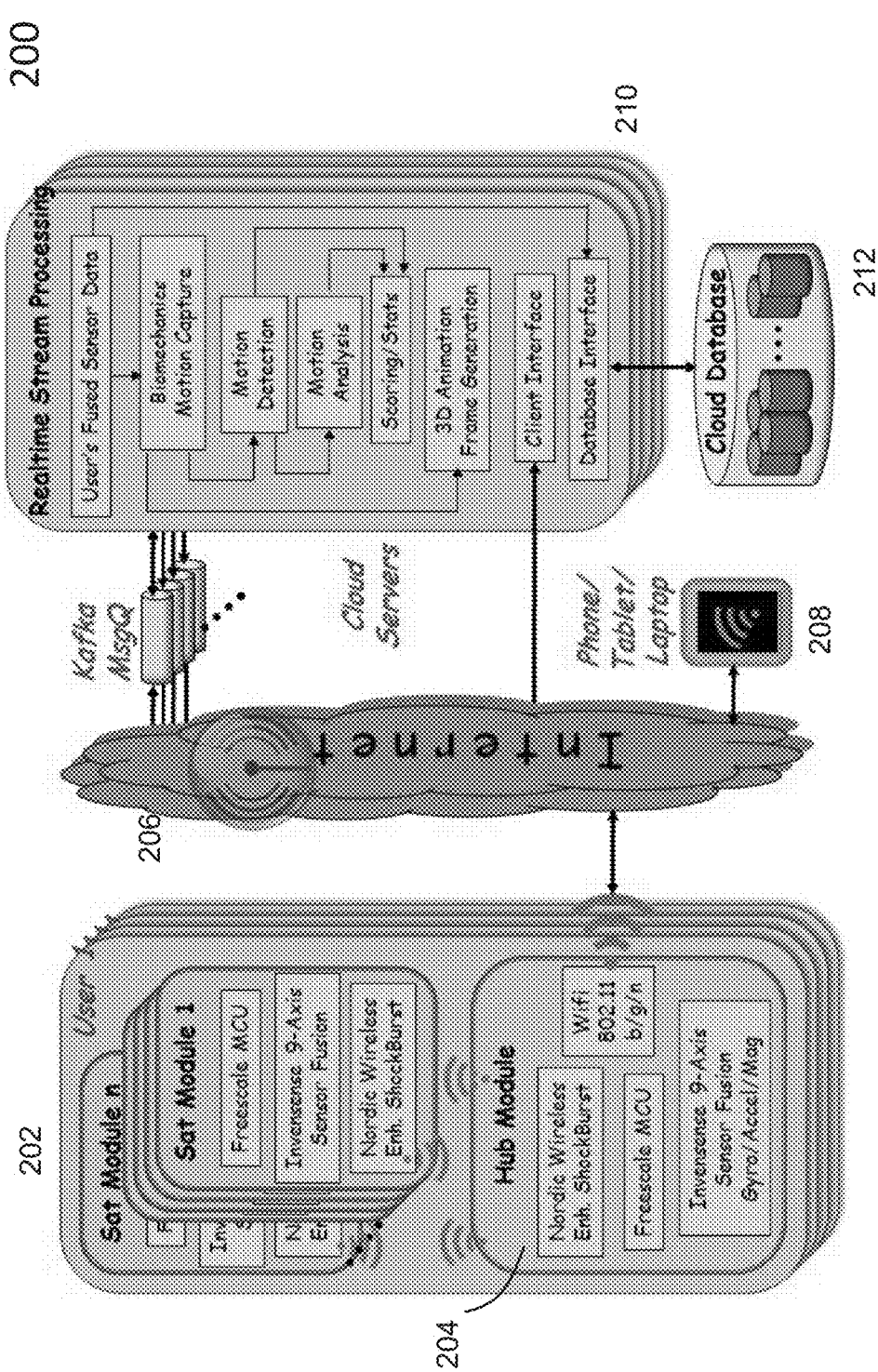
FIG. 2 shows a systemic functional block diagram according to one embodiment of the present invention.

FIG. 2 shows a systemic functional block diagram 200 according to one embodiment of the present invention. A user wears a set of garments embedded with sensor modules 202. The number of sensor modules 202 and placement can be determined depending on a target application and types of motion to be captured and analyzed. According to one embodiment, each sensor module comprises:

- a 9-axis sensor chip having integrated 3-axis gyroscope, 3-axis accelerometer, 3-axis magnetometer, such as those manufactured by Invensense;
- a 32-bit ARM Cortex M4F microcontroller (MCU) with floating point arithmetic unit (FPU) to perform floating-point math-intensive sensor fusion processing at every sensor module, such as those manufactured by Freescale; and
- a wireless chip with embedded 32-bit ARM Cortex M0 MCU to support 2 Mbps wireless communication, such as a Nordic 2.4 GHz wireless chip.

In one embodiment, the wireless chip is based on a proprietary and enhanced Shockburst protocol, which has been deployed for medical/industrial devices. Other standard wireless protocols like Bluetooth/BLE, Ant+ and Zig-Bee may also be employed. One of the sensor modules 202 is designed to function as a hub 204 of all the satellite sensor modules, controlling and collecting sensor data from the satellite sensor modules. The sensor data from the satellite sensor modules are received and combined with the sensor data generated in the hub 204 into one record having the same timestamp and streamed out to the cloud or the portable device. Typically, the sensor data sampling rate is at 100 Hz, producing gyro x/y/z, accel x/y/z, mag x/y/z, and quaternion w/x/y/z values for each satellite every 10 milliseconds. To get robust data bandwidth and wireless distance to a Wi-Fi router/hotspot, the system may include a Wi-Fi module supporting 802.11b/g/n. In the absence of Wi-Fi router/hotspot, the hub module can stream the sensor data directly to a mobile device 208 (e.g., smartphone/tablet/laptop), for example, via Wi-Fi-Direct protocol. If the mobile device 208 has limited computing resources compared to one or more cloud servers 210, motion capture/analysis may be performed based on reduced information from the sensor modules, but overall still delivering the benefits in the present invention.

In the presence of an Internet connection 206 to a cloud datacenter (e.g., the servers 210), the captured and combined sensor data records are streamed continuously to the cloud datacenter. The data stream queuing and processing may use a framework suitable for real-time stream analytics and having sub-second response time. In one embodiment, the system uses open-source software components, such as Kafka (for message queuing), Jetty (for application session management), and Rserve (for executing R math programs).

With a Kafka framework, the system can queue sensor data streaming from thousands to millions of users, while maintaining low latency requirement for real-time processing. Multiple sensor records may be batched to be processed by the known R math program. One or more R processes may be dedicated for each user to compute the following: Joint angle estimate of each joint based on multi-sensor data and human biomechanics model, rotational direction values of corresponding body segments, detection of the start, middle, end, and type of a motion that is unique to a target application, all based on a sequence of multi-sensor samples (called frames).

For example in tennis, a motion could be a forehand topspin with start frame at ready position, middle frame at ball contact, and end frame at completion of swing follow through. The motion is analyzed for different attributes or statistics, such as (for tennis) number of repetitions, footwork quality metrics (number of steps before ball contact, knee bend angle, balance), power metrics (swing speed, hand acceleration, ball strike zone), injury risk analysis (elbow, shoulder, wrist, back, knee), and etc., all based on the available joint angles, approximate rotation values of all 21 segments of human skeleton (wire body) that is ready to be rendered and animated by a 3D graphics software like Unity (commercially available 3D game engine software).

To complete the streaming, the output of various (joint angle) processing and motion attributes/stats can be streamed out to a user associated portable device to be further processed for live avatar animation and chart views. For playback and data analytics, every user's recording session may be stored in a cloud database or in the portable device. Both the raw sensor data input and output results (e.g., joint angle frames, motion attributes/stats) can be part of the session record. For animation playback and chart views, the output data may be retrieved and sent to a mobile device. When there is enhancement or addition to the motion capture and motion analysis algorithms, the system can re-generate the output results from the original input data.

The overall system stack comprises layers of hardware, firmware, wireless network, cloud infrastructure, real-time streaming software, biomechanics motion algorithms, database, big data analytics, 3D graphics, and a user interface. The following table summarizes the various aspects of the system.

| | Requirement | System Feature |
|---|---|---|
| 1. | Capture and analyze human motions with or without camera | Employ inertial sensor chips in smartphones and wearables to track movements. Multiple inertial sensors may track movement of body segments. To get better sensor fusion and positioning accuracy, a processor is employed to integrate all 3 micro-electro-mechanical (MEM) accelerometer, gyroscope, and magnetometer. To further improve human motion capture and analysis, biomechanics modeling and knowledge of the target application's activities are combined. |
| 2. | Instant biomechanics feedback | System performs high-speed algorithms to analyze motions based on human biomechanics model, joint angles, raw sensor data, and sensor fusion. System incorporates proper biomechanics knowledgebase and patterns into the motion library to compare with, based on the specifics of target application. |

| | Requirement | System Feature |
|---|---|---|
| | | These algorithms require substantial mathematical computations. To give instant feedback in sub-second, the system provides a real-time stream processing in the cloud for scalable computing. |
| 3. | Injury prevention analysis | The system may incorporate injury analysis and motion library patterns/signatures based on studies in biomechanics, physical therapy/rehabilitation, sports medicine, and experiments in the target application area. The system may continuously add more injury patterns into the motion library and algorithms and allow users to add their own injury patterns to recognize possible injury. |
| 4. | Live remote motion monitoring or coaching | In one embodiment, the system leverages the cloud capabilities to enable real-time motion monitoring of a user by other authorized users (coach, doctor, supervisor) from any distant places. Unlike video monitoring, the sensor stream bandwidth requirement may be several orders of magnitude less. |
| 5. | Share motion recordings with authorized users | In one embodiment, the system leverages the cloud infrastructure to share motion recordings with other authorized users. The system may record both the raw sensor data input and output results (animation frames, motion attributes). When there is enhancement or addition to the motion capture and motion analysis algorithms, the system can re-generate the output results from the original input data. |
| 6. | Data analytics insight | The system may store all user profiles and recordings in the cloud's scalable database/storage. The system may deploy big data analytics tools and search queries to gain insight information upon request on user's own data, or anonymous business intelligence. |
| 7. | Scalable and adaptable to many target applications | The system platform is based on an architecture with common building blocks that can scale and adapt to customization and many target applications. In one embodiment, the system leverages cloud's "infinite" computing resources to scale increased application complexity, the number of active users, concurrent sessions at peak usage, and newly developed applications. The system may implement on-demand cloud resource management with load balancing to handle changing requirements and demands. |
| 8. | Affordable | The system may optimize COGS (cost of goods sold) by choosing commodity/volume hardware components, cost-efficient contract manufacturers, and license-free open source software packages. The system may optimize operational costs through on-demand cloud resources. |
| 9. | Easy to use | The system may use an intuitive UI (user interface) with game technology where users of all ages can operate easily without a manual or complex instructions. The system may select features that give most benefits to users and present the feature capabilities in multi-level UI, starting from simple to deep analysis. The system may use sensor packaging and harness designed for simplicity and ease of use. |

Figure 3A:
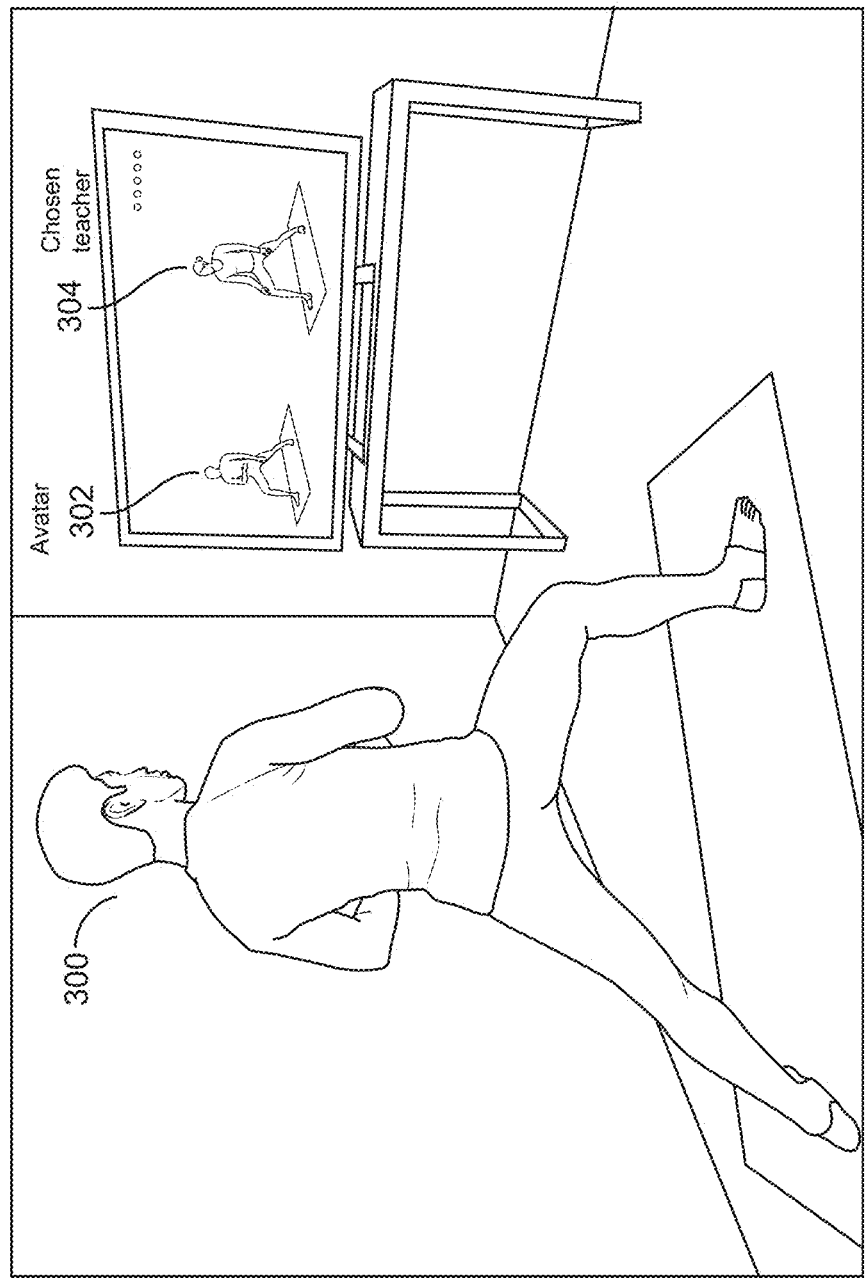
FIG. 3A shows an exemplary display a user may see, where a live avatar is rendered and inserted into a display video.

Referring now to FIG. 3A, it shows an exemplary display a user 300 may see a live avatar 302 is inserted into a display video. During the playback of an instructional video by a chosen teacher 304 in the PIVOT Yoga App, there are some extra spaces on one side of a frame. Into the extra space, the live avatar 302 representing the user 300 may be inserted as a comparison to the chosen teacher 304. For example, as the user raises his left arm, the corresponding avatar on the screen raises its left arm as well. In one embodiment, the avatar is rendered based on the sensor data received from the clothing embedded with the sensors. In another embodiment, one or more cameras are used to capture the pose of the user, images from the cameras are analyzed to derive a pose of the user, where the derived pose is used to render the avatar. As different camera angles come into view, the avatar, or appropriate portion of the avatar in the event of a close-up, will automatically move into correct position in view of the teacher.

Once in a pose, the user 300 may ask the system or strictly speaking, the chosen teacher for feedback on his pose. The request is received and recognized (nearly instantaneously), the view on the display may change. Instead of being in a side-by-side video environment, the user is now presented in an environment that has been specially designed for pose comparison. It is herein to refer this environment as Live Pose Comparison. According to one embodiment, the request may be generated from one or more sensors by the user tapping on a specific part of his body or a voice from the user.

In one embodiment, the avatar representing the user is superimposed on top of a reference avatar representing the teacher or a model designated by the teacher. Directly to the side is a numbered diagram of the mat, each side of the mat presents a perspective view of the avatar-teacher combination, and the user may switch among those views by calling out a selected view with his voice.

Figure 3B:
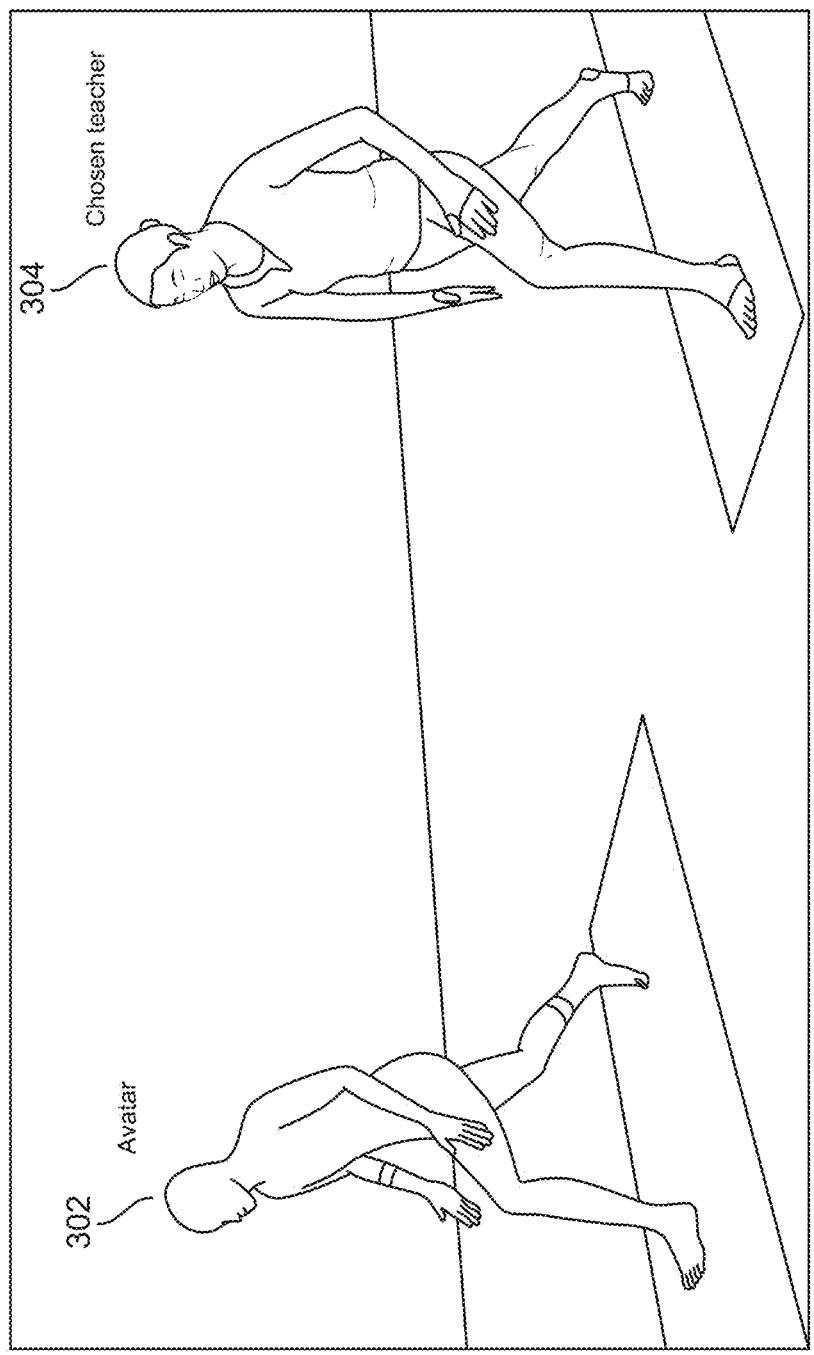
FIG. 3B shows an example of a perspective view (e.g., a 45-Degree view) in which a user avatar is placed on the right side of a representation of a chosen teacher.
Figure 3C:
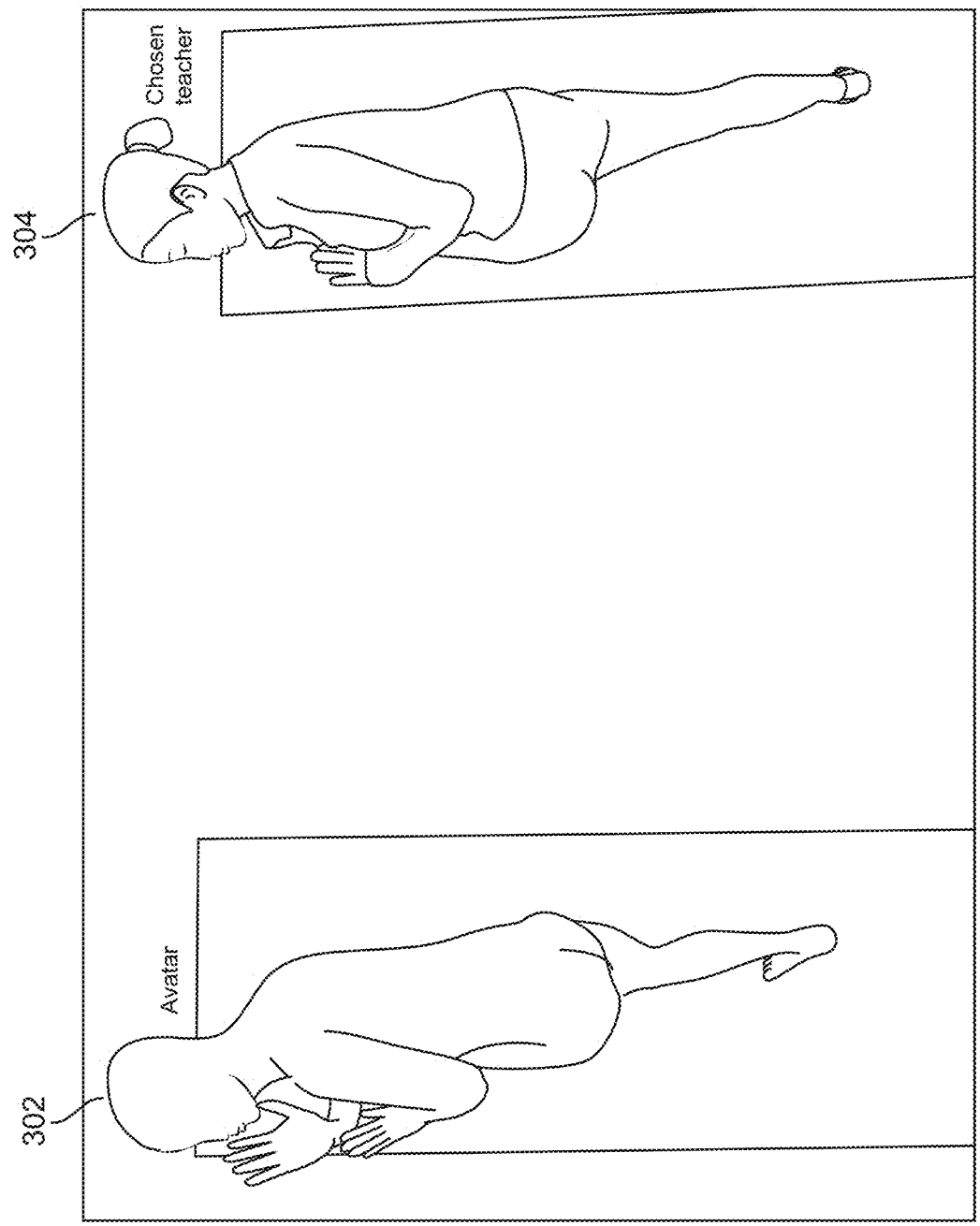
FIG. 3C shows an example of a direct overview, where a user avatar is placed on the left side of a representation of a chosen teacher.
Figure 3D:
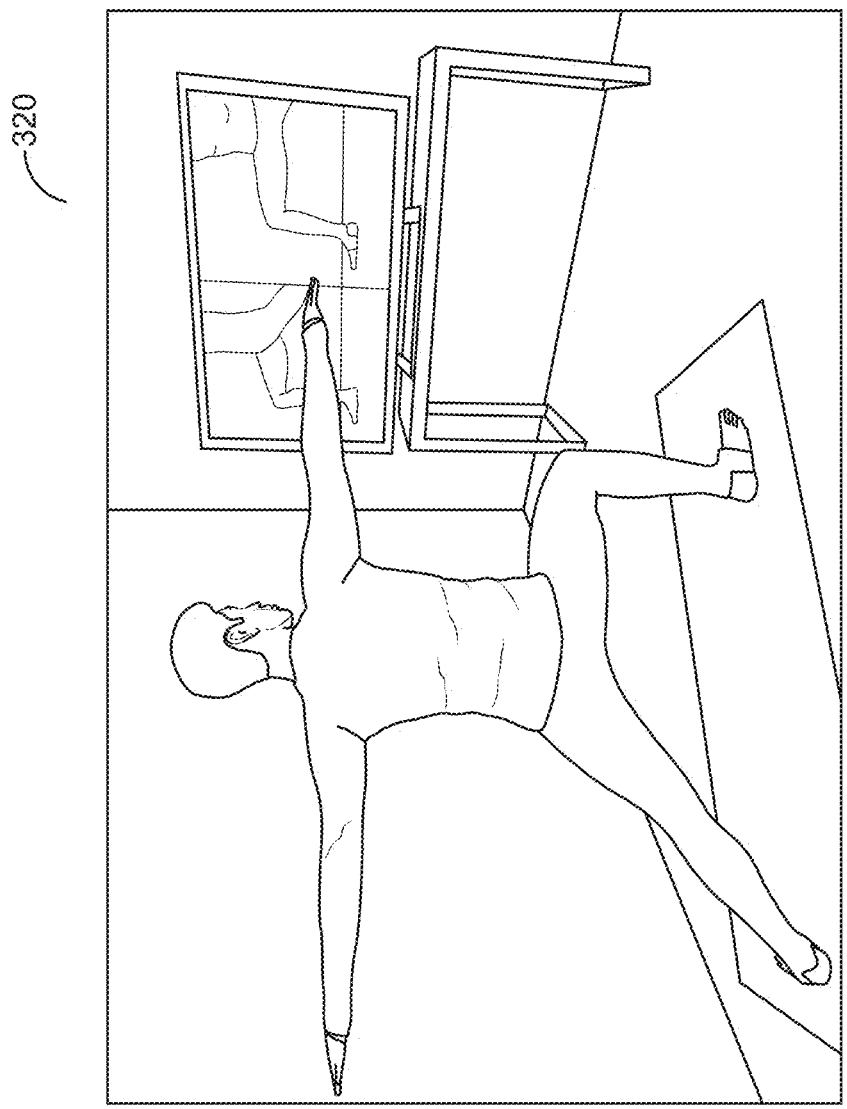
FIG. 3D shows a zoomed or close-up view of a user knee in a pose in comparison with the same performed by a chosen teacher, also in zoomed view.

FIG. 3B shows an example of a 45-Degree view, where the user avatar 302 is placed on the right side of the chosen teacher 304. FIG. 3C shows an example of a direct overview, where the user avatar 302 is placed on the left side of the chosen teacher 304. FIG. 3D shows a zoomed or close-up view 320 of a user knee in a pose in comparison with the same performed by the chosen teacher 304, also in zoomed view.

Figure 3E:
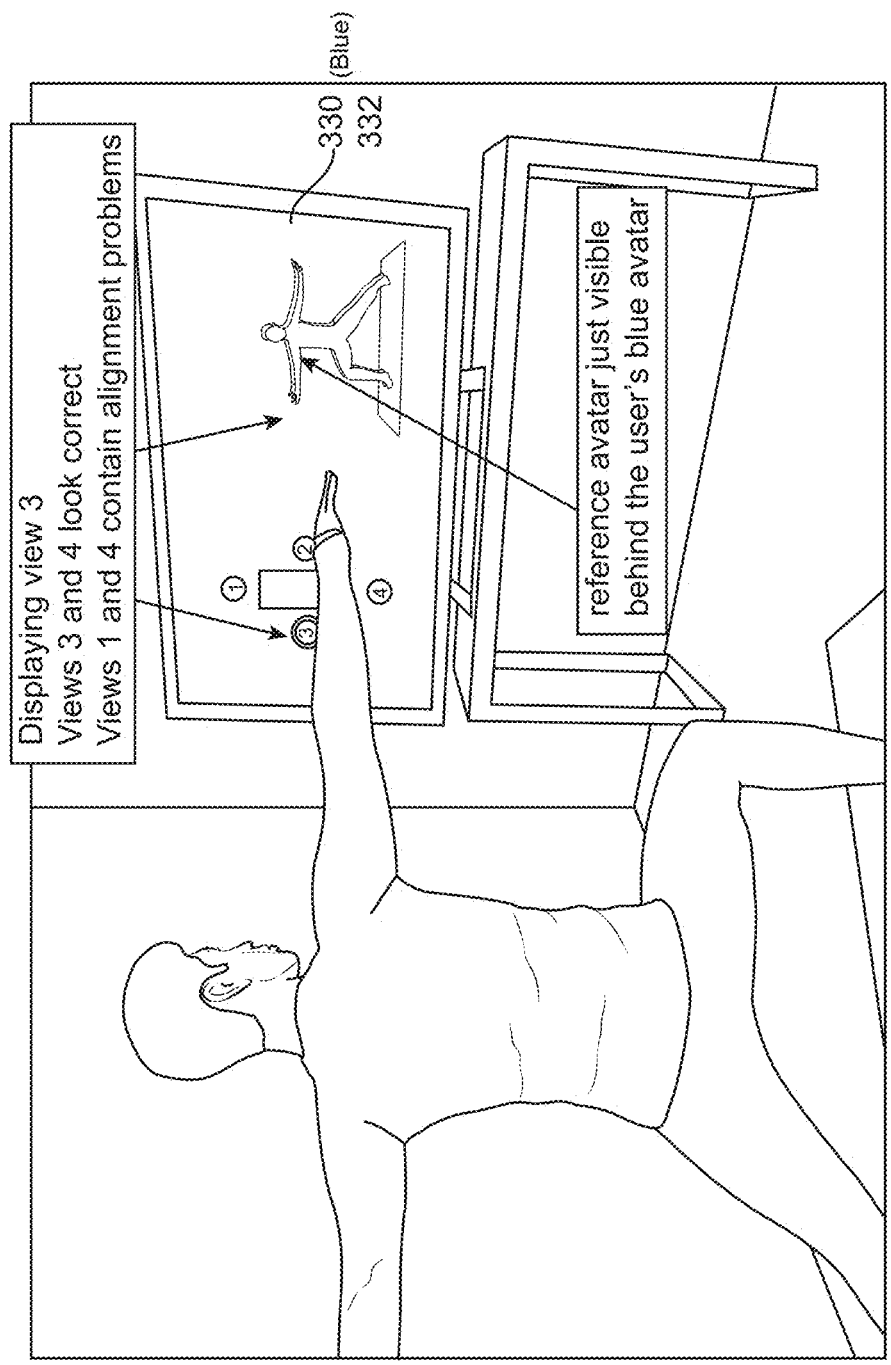
FIG. 3E shows what is referred to herein as Live Pose Comparison (LPC) Mode.

FIG. 3E shows what is referred to herein as Live Pose Comparison (LPC) Mode. Instead of being in a side-by-side video environment, the user is now presented in an environment that has been specially designed for pose comparison. In one embodiment, a user avatar 330 is superimposed directly on top of a reference avatar 332 (e.g., the teacher or a designated model by the teacher). Directly to the side is a numbered diagram of the mat, each side of the mat presents a different view of the avatar-teacher combination, and the user can switch among those views by calling out with his voice. According to one embodiment, as soon as the LPC is displayed, a teacher voice announces feedback in response to the pose the user is holding at the moment the user asked for feedback. This feedback may announce an important change that is needed at the moment and all done in the teacher voice. For example, the voice may indicate which body part needs to move, and how far in which direction.

Figure 3F:
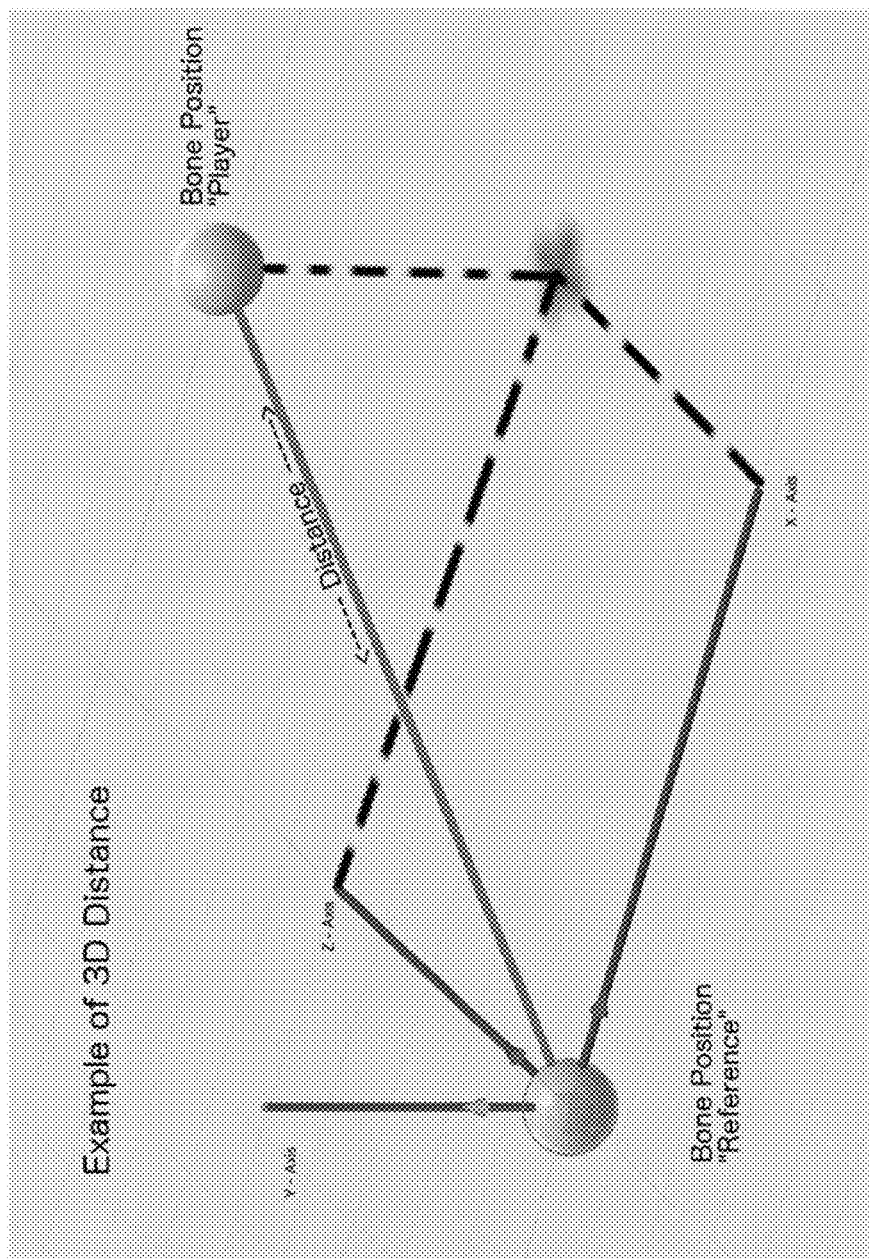
FIG. 3F shows the pose comparison by comparing the bones (or frames) of the user or player avatar to the bones (or frames) of the reference avatar.

In one embodiment, the pose comparison is done by comparing the bones (or frames) of the user or player avatar to the bones (or frames) of the reference avatar as shown in FIG. 3F. All of the bones are compared to their corresponding counterparts (e.g., the right hand of the player is compared to the right hand of the reference) using the basic 3D distance formula. This gives a distance between the current poses of the player and the reference. In one embodiment, the distance in Unity is measured in a predefined unit (e.g., meters or inches). The Unity is the 3D game engine software with which the system is designed.

With the results of this pose comparison, the player bone with the highest distance to its direct counterpart is identified. Errors between the two poses can then be determined. In one embodiment, an error is expressed in 3 component vectors (X/Y/Z), and a largest error component is to be corrected first. For example, if the bone with the largest error is the right knee, and the largest component of the error is −0.2 meters (negative corresponding to left) on the X Axis, then the player is instructed to move his right knee 0.2 meters to the right. This comparison is done in order and may be repeated if a threshold is not reached. In one embodiment, there is a default order. The player is instructed to correct his feet first, then his legs, chest, hands, and arms (in that order).

In addition to the pose correction, the decision about what body part to present for correction is a decision that can be made solely by the teacher. Each of the authoritative teachers adopted in the system may specify which errors in view of the pose differences to be corrected in any given pose, and a relative priority order of each of these corrections. In other words, different teachers may have different procedures to correct a pose error by a user (student). Accordingly, the selection of bones, the order in which they are corrected, and the axis that has priority for each bone, are determined and configured for each pose individually by a chosen teacher.

Regardless it is generic or teacher-specific pose correction, one of the important features is that the system (e.g., PIVOT Yoga) provides automatic confirmation of a user's adjustment to a correction. In one embodiment, as soon as the user had made the suggested correction (within a pre-set tolerance level), the App is designed to have a response from the teacher, e.g., "That's good!" or "Please move your right arm a bit more right".

In the LPC mode, the user avatar is superimposed onto the teacher avatar (normalized so that the heights of the two avatars are substantially similar or the same), and the user has the control for changing which side of his yoga mat is being displayed. If there are significant-enough alignment problems on a particular side of a pose, that corresponding view is highlighted (e.g., in red). The assessment is based on a tolerance level that may be predefined or set up by a user or the teacher.

A user may always rely on the avatar comparisons directly. The reference avatar can be in a different color (e.g., yellow) and visually behind the user avatar as shown in FIG. 3E, any yellow peeking through would generally indicate an alignment error for the user pose. Even though the user avatar and reference avatar are displayed in 2-dimension (2D) planes, the raw avatar data (bones and joint angles) are being tracked and compared in full 3-dimension (3D) space accuracy. More viewing angles in any 2D views (e.g., top view) and any 3D views (e.g., rotating in 360 or 720 degrees) can be provided and shown.

As an extension to the pose comparison, for each bone on the player, the axis with the highest degree of error is identified and counted. The axis is used to determine which angle would give the player the best view of his avatar for correcting his pose error. For example, if there are 10 bones, the user receives correction messages 5X, 3Y, and 2Z. In this scenario, the user has the most errors in the X Axis (left/right), so top-down or frontal view may be selected based on other refining factors.

For the teacher-specific pose comparison, the system is designed to automatically display to the user the camera view for the side of his pose which has the most severe alignment problems according to the chosen teacher. Based on the teacher's prioritized bone order of correction, the camera angle is selected based on the prioritized bone's largest error in the X, Y, or Z axis.

Figure 3G:
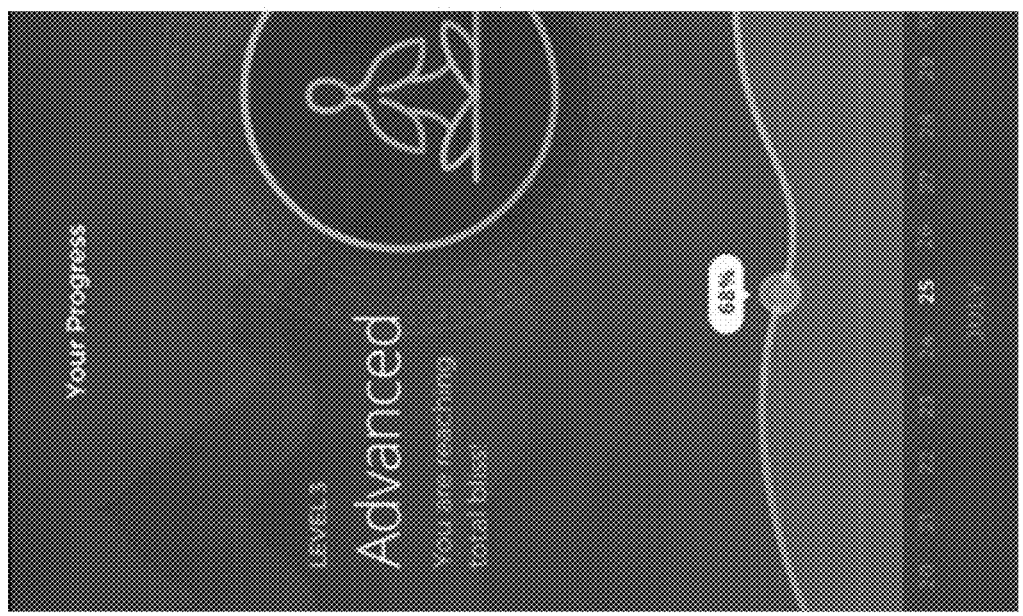
FIG. 3G shows an exemplary score chart.

According to one embodiment, a user scoring algorithm is designed. For each pose, there is a 3D reference model (e.g., based on or from the teacher). Based on the model, it can be calculated how closely the user is approaching that pose in 3D. The difference may be reported, for example, as a percentage. According to one embodiment, each frame is observed while the user is nominally in a given pose. The frame that has the smallest percentage of overall deviation against the reference pose is selected with full 3D accuracy. The percentage is recorded as a score for that pose in the teacher's sequence on that day, and can be used to track the pose (and display it to the user) over time. An underlying scoring algorithm is to leverage the pose comparison. For each bone on the player, the distance to its direct counterpart is saved. These distances are compared against a set of thresholds to determine the score. For example, if the minimum threshold is 0.05 meters, the maximum threshold is 0.25 meters, and all bones are greater than 0.25 meters from their counterparts, then the player would receive a score of 0 (zero). Likewise, if the bones were all less than 0.05 meters from their counterparts, the player would receive a score of 100 (one-hundred). Values on this scale are determined by how far each bone is from its counterpart. For a second example, if there are 10 bones, 8 of which are below the minimum threshold, and 2 of which are beyond the maximum threshold, then the player would receive a score of 80%. FIG. 3G shows an example of scoring of poses performed by a player over a period, which also shows the score statistics of the player for each pose or aggregated poses of each session, tracking the progress over time and multiple sessions. The App presents this scoring to show the user his "Best" or "Worst" pose, and enable the user to share each on a social media, e.g., Facebook.

To give more realistic animation, the user avatar is modeled as accurately as possible. In one embodiment, a user height is obtained from the user. The height information is used for all calculations, especially for modeling the user avatar when to place the avatar on the screen (e.g., where to place on the screen the head of the user who is bending at his knees). The standard anthropometric parameters are used, where the length of all body segments can be approximated as a ratio of user height (H) as shown in FIG. 3H. This approximation may differ in certain actual body segment length(s) of the user. In one embodiment, the user's actual body part lengths are adopted to scale the user avatar body parts, through initial calibration poses that could be actual yoga poses.

There are times, particularly in Yoga, certain poses have well known positions in which known body parts must be on the ground and at certain joint angles. For example, the Downward Facing Dog pose has both hands and feet on the ground (mat) with the legs, spine and arms fairly straight. If a user is asked to be in this pose, and yet the user avatar's hands or feet are not planted on the ground/mat, certain body segment length(s) are scaled accordingly to match user's actual pose with hands and feet on the mat. To reduce variation of the pose, markings (e.g., hand prints, foot prints) on the mat are used to position the user according to his height. So based on stored knowledge of which poses require which, the length of the avatar's bones can be mathematically expanded or contracted. In general, a user can be asked to do multiple "calibration" poses to arrive to the best body segment scaling of the avatar specific to the user.

Figure 3I:
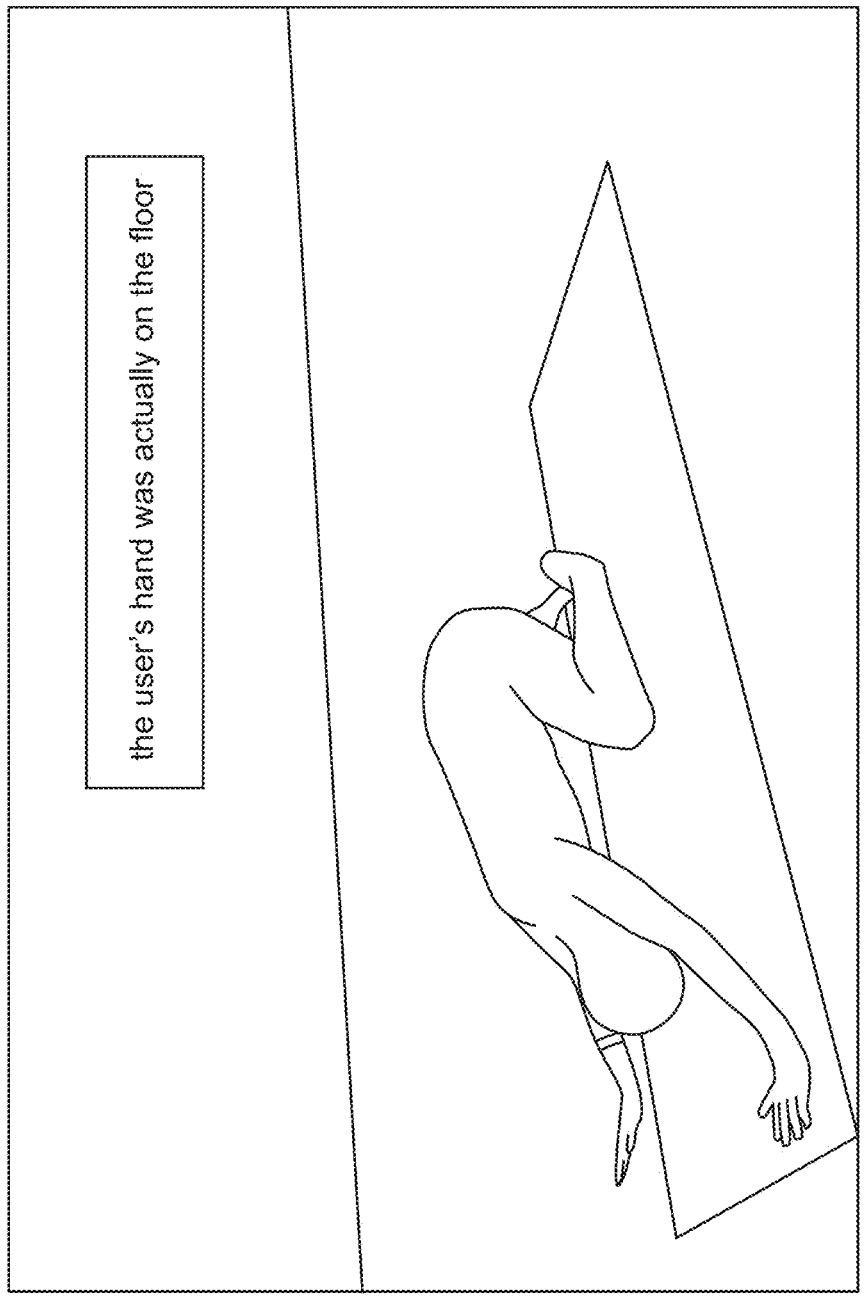
FIG. 3I shows an example in which a user's hand is not rendered to touch the floor.

Many calculations are made in real time to display all parts of a user's body properly. All of those calculations require an anchor which is a single point that all measurements are based from. It turns out that using the same anchor for all poses can create some small discrepancies. After all, some poses in yoga are standing up; and some poses are lying down; and some poses are on the hands and knees. If the user is in a pose with their hands on the floor, and we're using an anchor that assumed the user was standing up, the result will be that the user's hands, in the motion capture display, would not actually seem to touch the floor, as shown in FIG. 3I.

To address this, dynamic anchoring technique is designed to chooses an anchor point in the background based on a known pose. In one embodiment, the dynamic anchoring method ensures that any given avatar always remains on the 'ground' in 3D space (in Unity). This is achieved by identifying which bone on the avatar has the lowest position on the Y Axis, and moving the entire avatar by the opposite of that value such that the lowest bone is always at ground level.

Figure 4A:
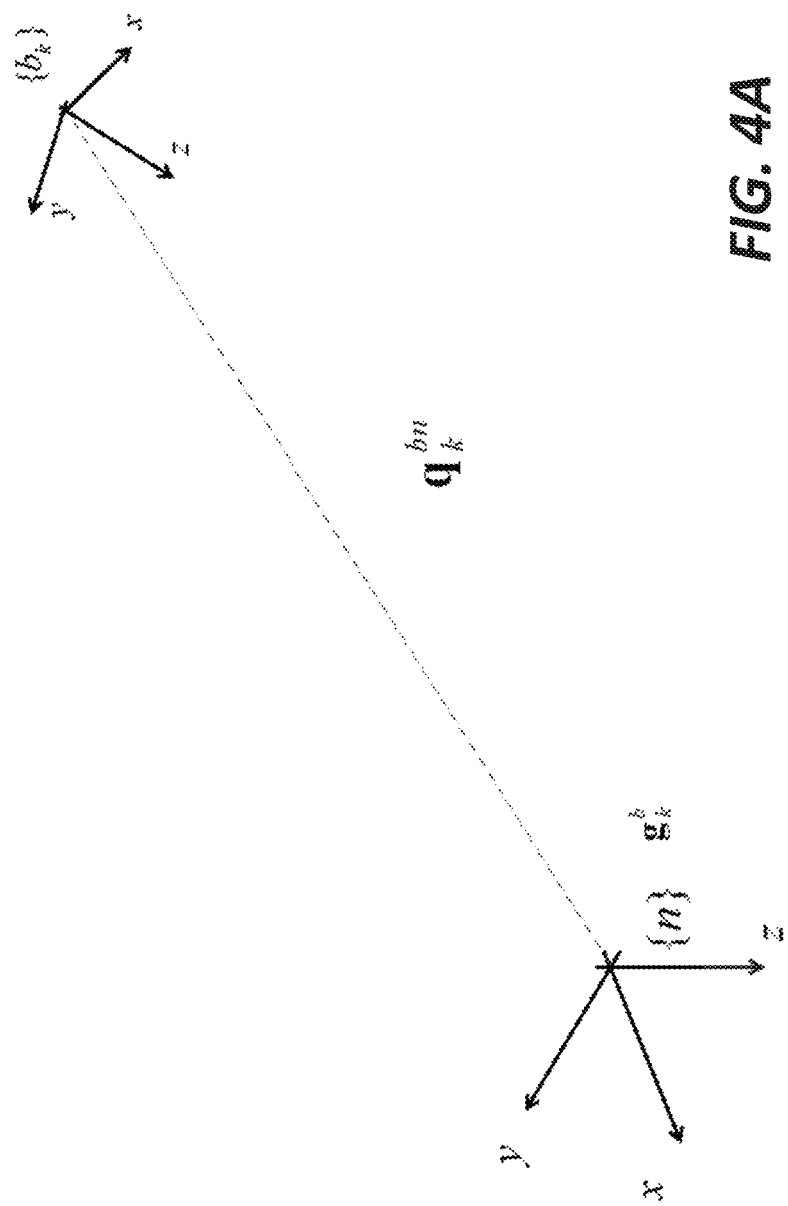
FIG. 4A illustrates a quaternion of orientation qf which rotates the global reference frame {n} into the sensor (local) reference frame {b} at time k.

According to one embodiment, a motion capture system (referred herein as PIVOT Mag Free) is designed and relies on gyroscope and accelerometer only. The inertial sensors in FIG. 1B are 6-axis inertial sensors having only gyroscopes and accelerometers. The design is based on an algorithm for tilt estimation (angles with respect to the vertical direction) which is augmented with gyroscope integration for the heading estimation (angle about the vertical direction). A sensor fusion algorithm is designed to take the accelerometer and gyroscope measurements as an input. The output is the quaternion of orientation $q_k^{bn}$ which rotates the global reference frame {n} into the sensor (local) reference frame {b} at time k, see FIG. 4A. The global reference frame of the sensor fusion algorithms running in each sensor has the z axis aligned with the vertical direction and the x and y axis (in the horizontal plane) resulting from the initial sensor orientation.

Figure 4B:
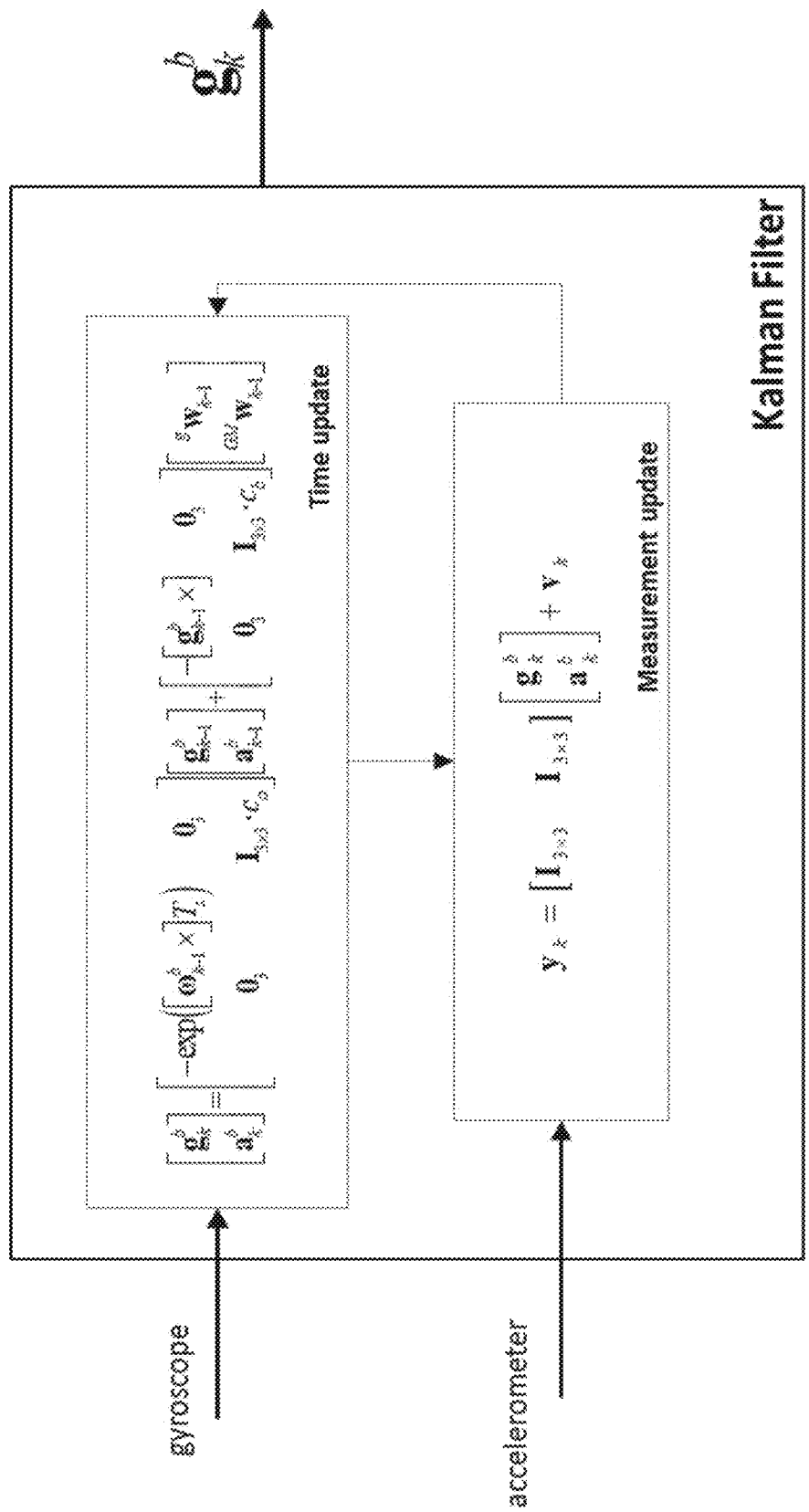
FIG. 4B shows an algorithm block diagram implementing a linear Kalman filter to estimate the vertical direction in dynamic conditions by means of the gyroscope and accelerometer data.

In one embodiment, a linear Kalman filter is used in order to estimate the vertical direction in dynamic conditions by means of the gyroscope and accelerometer data. The algorithm block diagram is presented in FIG. 4B. After the vertical direction is estimated, a horizontal reference needs to be available in order to compute the tree dimensional orientation of the sensor reference frame with respect to the global reference frame. Since a magnetometer is not used in PIVOT Mag Free, this horizontal direction can be computed with the gyroscope data. At time zero, the horizontal reference measured in the body frame is assumed to be a known canonical vector, i.e., the x axis (1, 0, 0) of the global reference frame. As the time passes and the body moves, the gyroscope data is used to project in time the horizontal reference in the body reference frame. The time-propagation equation of a 3D vector, given the body angular velocities, is given by the following equation:

$$\begin{cases} h_0^b = (1, 0, 0) \\ h_{k+1}^b = -\exp([\omega_k^b] T_s) h_k^b \end{cases}$$

Figure 4C:
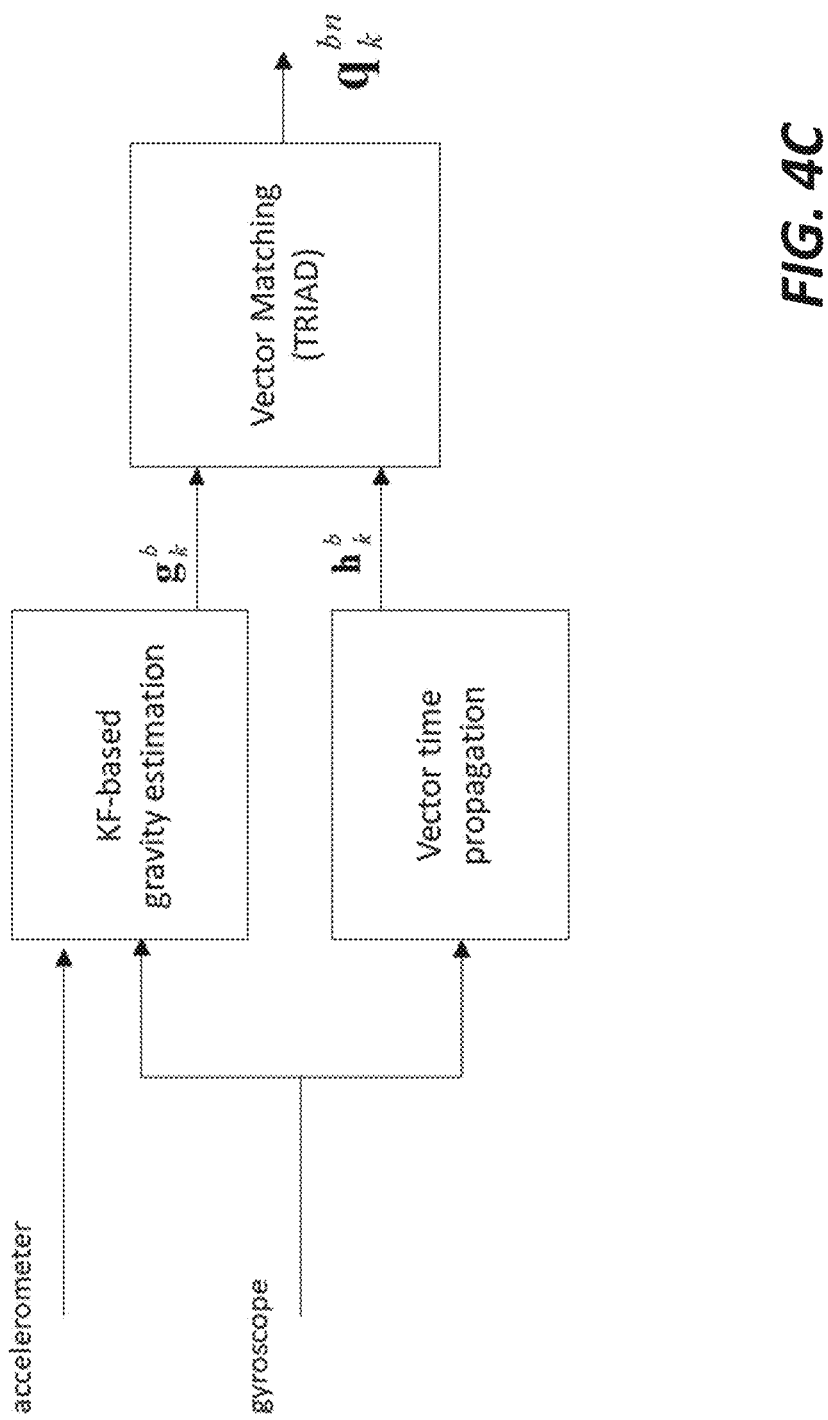
FIG. 4C shows an overall workflow of the three-dimensional orientation estimator according to one embodiment.

Once the horizontal and vertical directions are known in the global reference frame (known a priori) and in the sensor reference frame (estimated with sensor data), the orientation of the global reference frame with respect to the sensor reference frame can be computed. In one embodiment, the TRIAD method being a very popular computational procedure is used. FIG. 4C shows an overall workflow of the three-dimensional orientation estimator according to one embodiment.

A non-null bias in the gyro measurements sometimes results in a drifting error in the output of the angular speed time integration. Such a bias can be accurately estimated by averaging gyroscope measurements while the sensors are still (e.g., on a table). However, the accuracy of the estimated bias is heavily degraded by possible user motions during the calibration procedure. For this reason, the Kalman filter is designed for being able to estimate the gyroscope biases while the sensors are worn by the user. The rationale is to use a more complex algorithm (a Kalman filter vs. a simple average) to deal with user's (moderate to low) motion during the gyroscope calibration.

In one embodiment, the gyroscope measurements $gyr_k^b$ are modeled as the sum of the true angular velocity Wo, the gyroscope bias $b_k^b$ and the white noise $v_k^b$:

$$gyr_k^b = \omega_k^b + b_k^b + v_k^b$$

Figure 4D:
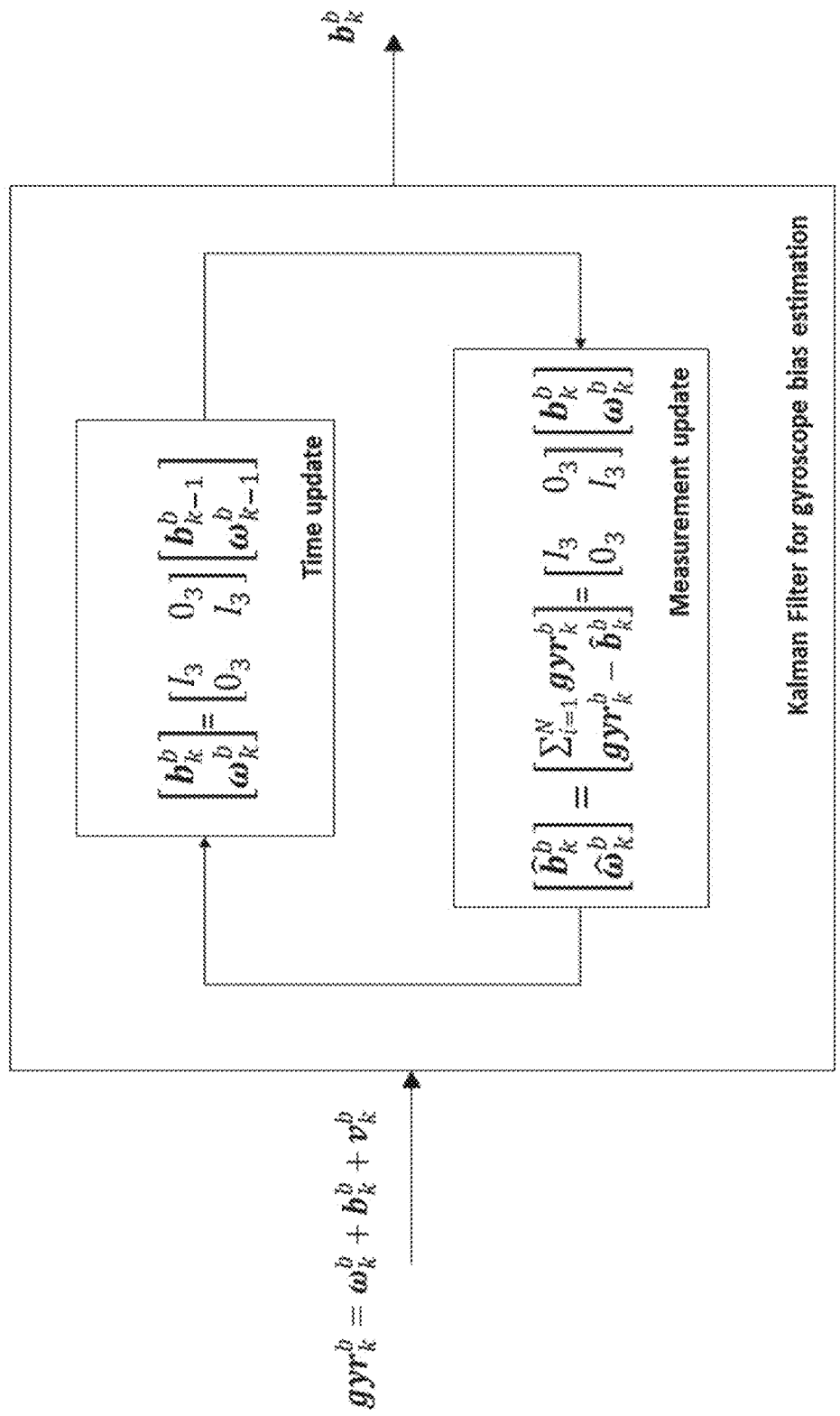
FIG. 4D shows an estimation of bias given the measurements $gyr_k^b$.

The aim of the Kalman filter in PIVOT Mag Free is the estimation of the bias $b_k^b$ given the measurements $gyr_k^b$, as shown in FIG. 4D. The bias and the angular velocity are considered as the inner state of a dynamical system. These two states are modeled as time-constant variable. These states are also considered to be the output of the dynamical system, as shown in FIG. 4D. They can be derived from the gyroscope measurements as follows:

$$\begin{cases} \hat{b}_k^b = \sum_{i=1}^{N} gyr_k^b \\ \hat{\omega}_k^b = gyr_k^b - \hat{b}_k^b \end{cases}$$

A biomechanical protocol implemented in PIVOT Mag Free includes a set of definitions and computational procedures that allow relating sensor readings (angular velocity and acceleration) and sensor fusion output (quaternions) to the motion of the body segment. Three main blocks are required to reach this goal: the biomechanical model definition, the Sensor-To-Segment (STS) calibration and the alignment of the global reference frames of each sensor attached to the body.

Biomechanical Model

Figure 4E:
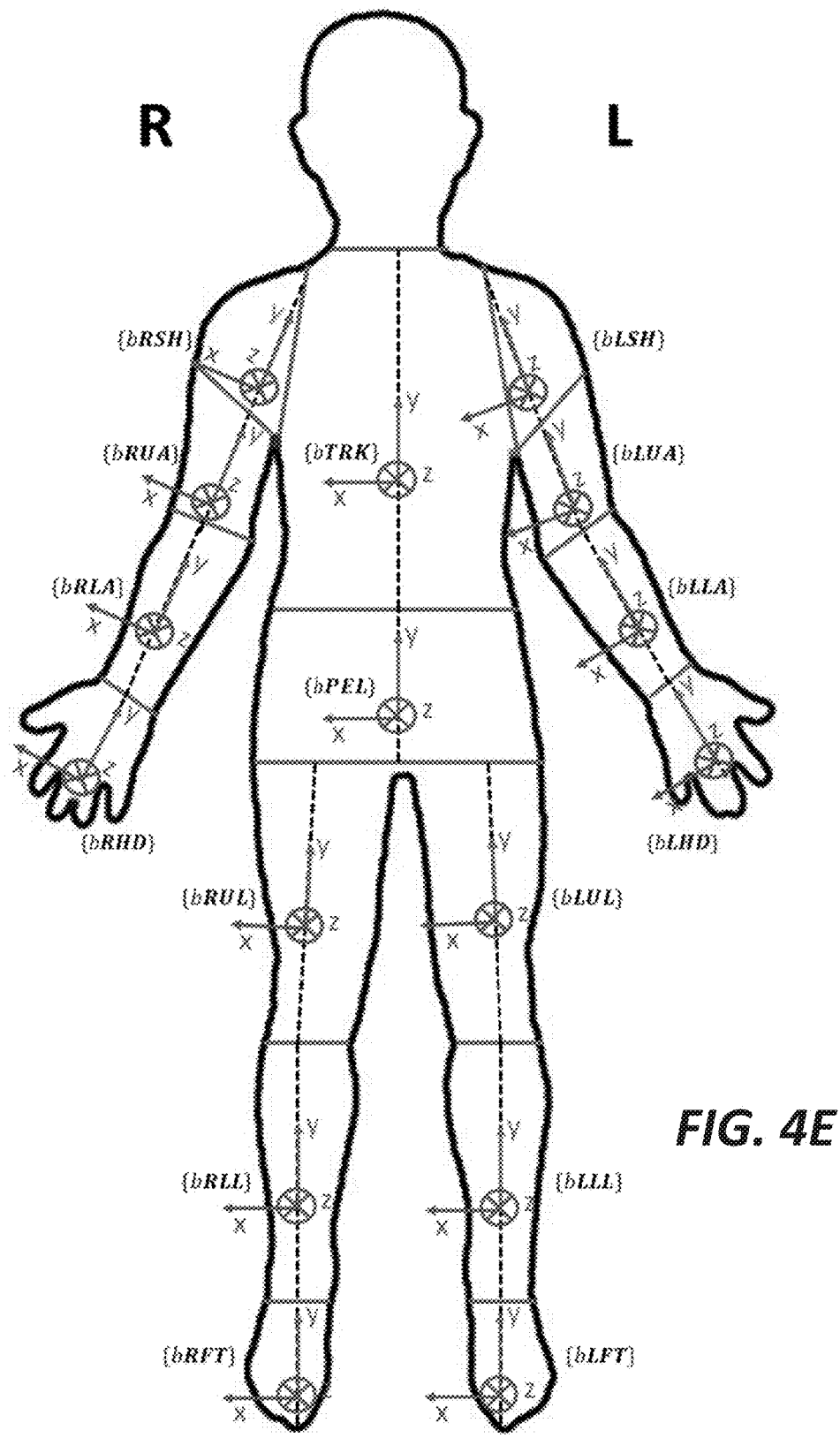
FIG. 4E illustrates an exemplary biomechanical model defined in the PIVOT Mag Free biomechanical protocol according to one embodiment of the present invention.

The biomechanical model defined in the PIVOT Mag Free biomechanical protocol is shown in FIG. 4E according to one embodiment of the present invention. Specifically, FIG. 4E shows an anatomical reference frame for all of the 16 body segments considered in PIVOT Mag Free. The y-axis is assumed to be the longitudinal axis for all the body segments while the x-axis is assumed to coincide with the medio-lateral direction (positive from left to right). Therefore, the z-axis is represented by the antero-posterior direction (positive from the front to the back). In one embodiment, fourteen body segments are considered: six segments for the upper limb: upper arm, forearm and hand (left and right), six segments for the lower limb: thigh, shank and foot (left and right), trunk and pelvis.

Sensor-to-Segment Calibration

It is known to those skilled in the art that there are two main approaches: anatomical methods, where a user is asked to stay still in simple and known body poses (N-pose, T-pose and etc.) and functional methods, where the user is asked to perform very simple calibration motions. In the former, the estimated quaternions are compared with the ones expected in the known static pose. From this comparison, the STS misalignment (STS quaternion) is estimated with the aim of compensating the IMUs quaternions during the motion capture session, where IMU stands for inertial measurement unit, each IMU is included in a sensor module. In the latter, body rotational axes are measured through the calibration motion in the sensor reference frame and then used to build the STS orientation.

As described above, the quaternions returned by PIVOT Mag-Free sensor fusion running for each body segment refer to a different global reference frame. In one embodiment, a functional method (two-step procedure) is used to estimate the STS quaternion based on the raw sensor data, i.e., accelerometer and gyroscope data.

Vertical Direction Estimation: N-Pose

The first step of the proposed calibration method includes asking a user to stay still in N-pose. For each sensor, accelerometer data is measured and averaged during this time window to produce an estimate of the reaction to the gravity (vertical direction, upward) seen from the sensor reference frame. The N-pose assumption derives that each body segment reference frame has the y-axis (see FIG. 4E and FIG. 4F) which is aligned with the vertical direction. For this reason, the averaged accelerometer vector represents an estimate of the longitudinal direction of the relative anatomical reference frame.

Medio-Lateral Direction Estimation: Functional Motions

Figure 4F:
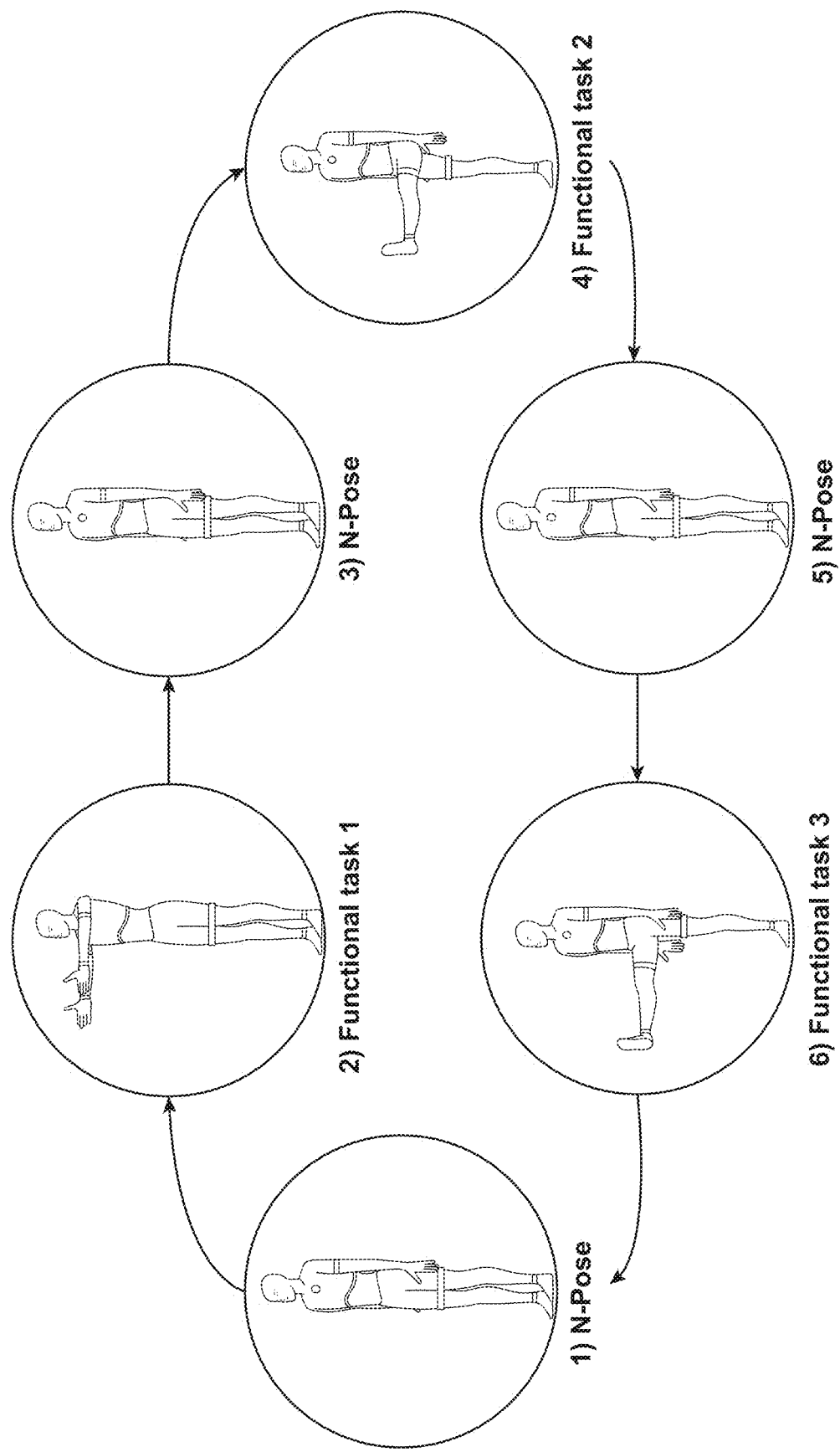
FIG. 4F shows that an N-pose assumption derives that each body segment reference frame has the y-axis.

The second step of the STS calibration implemented in PIVOT Mag Free is represented by the functional motions. In this stage, the user, starting from an N-pose, is asked to perform the following motion sequence as shown in FIG. 4F:

90 degrees flection of the upper arms in the sagittal plane, keeping the forearm and hand rigid with respect to the upper arms.

90 degrees flection of the left thigh in the sagittal plane, keeping the shank and the foot rigid with respect to the thigh; and 90 degrees flection of the right thigh in the sagittal plane, keeping the shank and the foot rigid with respect to the thigh.

During each motion, gyroscope measurements are acquired and normalized to one. The circular average of the normalized gyroscope represents the estimate of the Medio-lateral direction of that body segment seen from the corresponding sensor reference frame. No functional motions are required for the trunk and pelvis because sensor position on those body segments is quite constrained by the garment design. Therefore, the medio-lateral direction is assigned a-priori according to the physical orientation of the sensor with respect to the body.

Medio-Lateral Direction Refinement: Angular Grid-Search Method

The medio-lateral direction estimated during the functional motions described above can have a poor inter-subject repeatability. This is especially true for those body segments with a relevant amount of soft tissues and muscles such as the upper arms and the thighs. For this reason, in PIVOT Mag Free a computational procedure was introduced which is called angular grid-search. The underlying idea of this method is to consider the output of the functional motions output (i.e., the average mean of the gyroscope data) as an initial guess which is then refined based on the computation of a cost function over a pool of candidate directions. In the following, the main steps of the grid-search algorithm are listed and detailed.

Angular Grid Computation

Figure 4G:
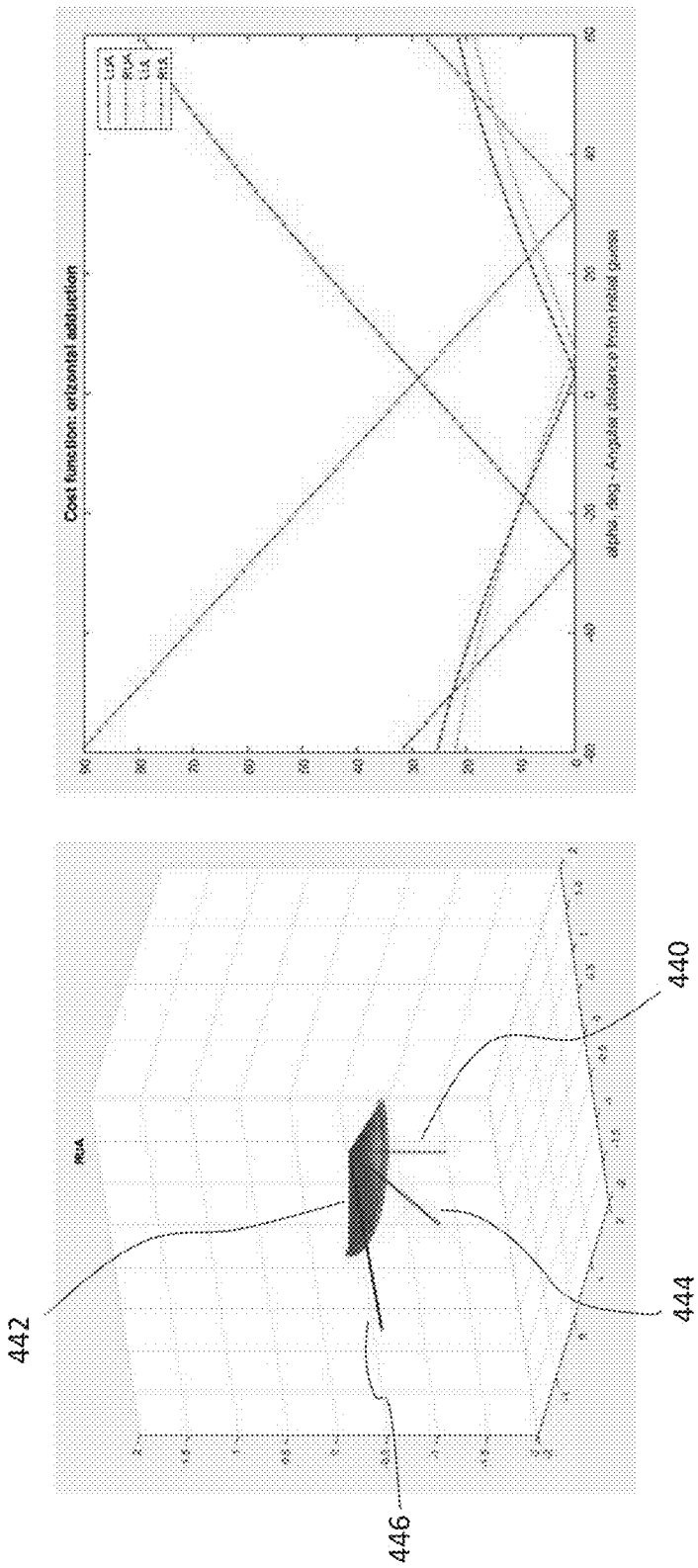
FIG. 4G shows (a) a grid search algorithm working principle for one body segment, angular grid, anatomical longitudinal axis, mediolateral direction initial guess and refined mediolateral direction (black), and (b) a cost function over the grid for four body segments left and right upper arm and left and right upper leg.

The angular grid is represented by a pool of directions which lie in the horizontal plane and are equally distributed in the range of +/−60 degrees with respect the initial guess. The horizontal plane is computed as the plane orthogonal to the vertical direction estimated during the first N-pose by means of the accelerometer data. In FIG. 4G, the line 440 represents the vertical direction while the lines 442 represent the guess directions. Such grid is built by computing all the directions in the horizontal plane with an increment of about 1.5 degrees, spanning the +/−60 degrees range with respect to the initial guess. The initial guess is represented by the projection onto the horizontal plane of the average gyroscope vector computed during the functional motions (the line 444). The refined (and final) direction is represented by the line 446.

Cost Function Computation

The cost function is based on the assumptions that functional motions are performed within the sagittal plane with null pronation. Hence, for the arm segments (upper arms, forearms and hands) the cost function to be minimized is represented by the horizontal adduction during the arm functional calibration (stage 2 in FIG. 4F). Same rule is applied to the leg segments, considering the corresponding functional calibration stage. The direction which results in the cost function minimum is taken as the medio lateral direction for that segment. As an example, in FIG. 4G, the cost function for the left upper arm, right upper arm, left upper leg and right upper leg are reported.

Final STS Orientation Estimation: TRIAD Method

From the biomechanical model definition, the vertical and medio-lateral directions of all body segments are assigned as (0, 1, 0) and (1, 0, 0) respectively. On the other hand, both directions have been measured in the two-step procedure described above. Therefore, given this coupled vector observations, the STS orientation can be computed easily by means of the TRIAD method.

Global Reference Frame Alignment

Figure 4H:
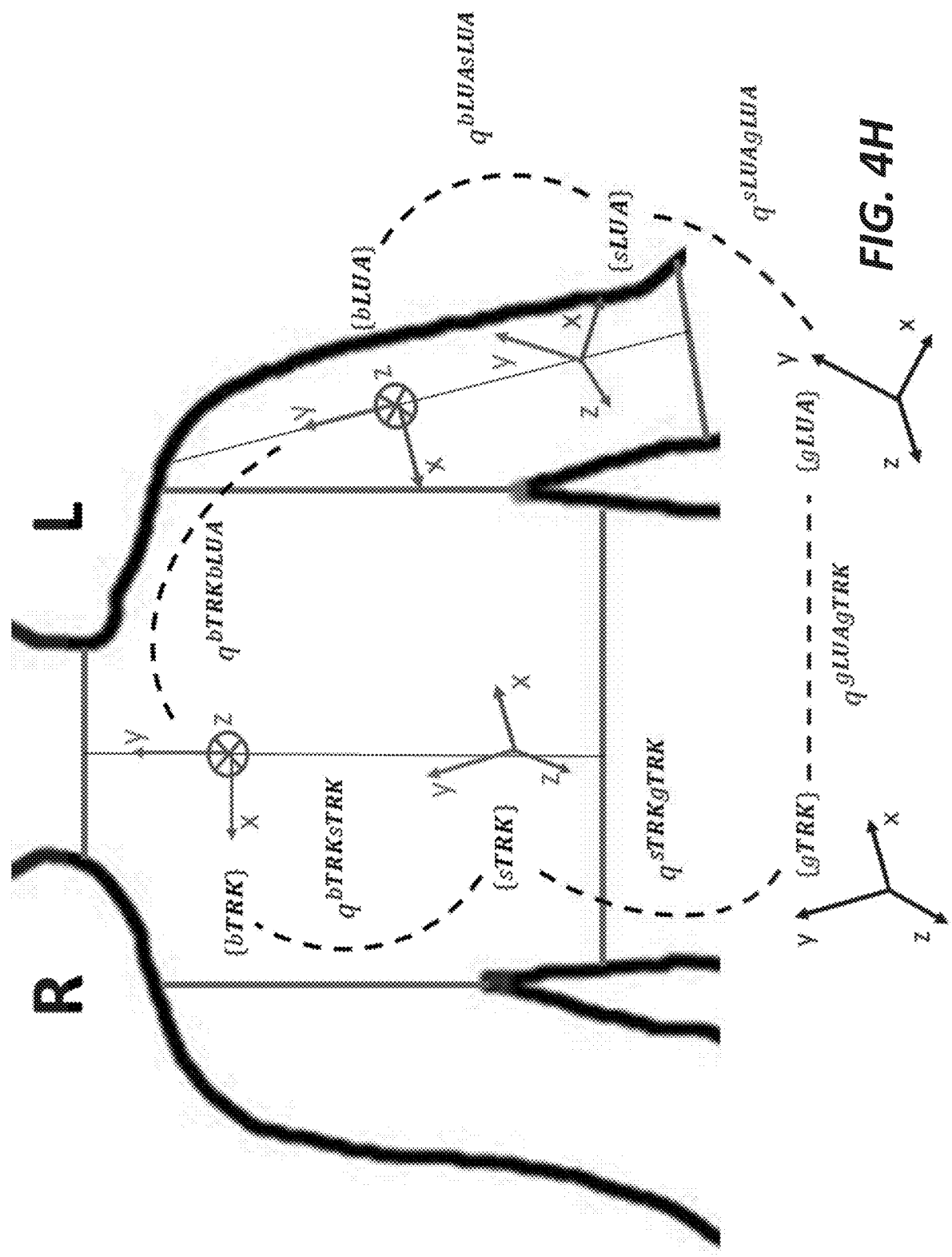
FIG. 4H shows each IMU has a global reference frame that depends on its physical orientation at the time in which a sensor fusion algorithm is started.

Each IMU has a global reference frame that depends on its physical orientation at the time in which the sensor fusion algorithm is started, as shown in FIG. 4H. Hence, a further compensation is needed when joint angles are to be computed. It should be noted that this additional step would not be required by standard sensor fusion algorithms that make use of magnetometer measurements. In fact, it is possible to define a unique global reference frame for all the sensors when magnetometer data are used. For this reason, an additional computational stage is added in the PIVOT Mag Free biomechanical protocol workflow. This procedure needs to be repeated every time a new motion capture session is started (i.e., all the sensor fusion algorithms are started on all the body segments). Two assumptions are necessary: the user is in an N-pose and STS calibration quaternions are already available.

For example, considering the trunk and the right upper arm, the following equation holds:

$$q^{gRUAgTRK} = (q^{sRUAgRUA})^{-1} \otimes (q^{bRUAsRUA})^{-1} \otimes q^{bRUAbTRK} \otimes q^{bTRKsTRK} \otimes q^{sTRKgTRK}$$

If assumption 1 hold, then $q^{bRUAbTRK}$ (1,0,0,0), since the trunk and right upper arm body segments are aligned during N-Pose:

$$q^{gRUAgTRK} = (q^{sRUAgRUA}|_{Npose})^{-1} \otimes (q^{bRUAsRUA})^{-1} \otimes q^{bTRKsTRK} \otimes q^{sTRKgTRK}|_{Npose}$$

If assumption 2 holds, then $q^{bRUAsRUA}$ and $q^{bTRKsTRK}$ are known and the global reference frame misalignment $q^{gRUAgTRK}$ can be computed.

In PIVOT Mag Free, the trunk is taken as the global reference. Therefore, the generic formula to estimate the global reference frame misalignments between the reference (trunk) and any other body segment X can be computed as follows:

$$q^{gXgTRK} = (q^{sXgX}|_{Npose})^{-1} \otimes (q^{bXsX})^{-1} \otimes q^{bTRKsTRK} \otimes q^{sTRKgTRK}|_{Npose}$$

It shall be noted that this estimated global reference misalignment will hold for all the motion capture sessions, but it needs to be recomputed if the sensor fusion algorithms are restarted.

The joint orientation computation between two body segments is computed with the following formula:

$$q^{bDISbPRX} = q^{bDISsDIS} \otimes q^{sDISgDIS} \otimes q^{gDISgTRK} \otimes$$
$$(q^{gPRXgTRK})^{-1} \otimes (q^{sPRXgPRX})^{-1} \otimes (q^{bPRXsPRX})^{-1}$$

where DIS stands for distal and PRX stand for proximal. This formula represents the way all the blocks described above (i.e., sensor fusion outputs, sensor to segment calibration and global alignments) are put together to estimate the joint orientations. It is also shown how the trunk global reference frame is taken as reference for all the other segments. The joint quaternion will then be transformed into joint angles with standard quaternion to Euler angles formula.

Figure 4I:
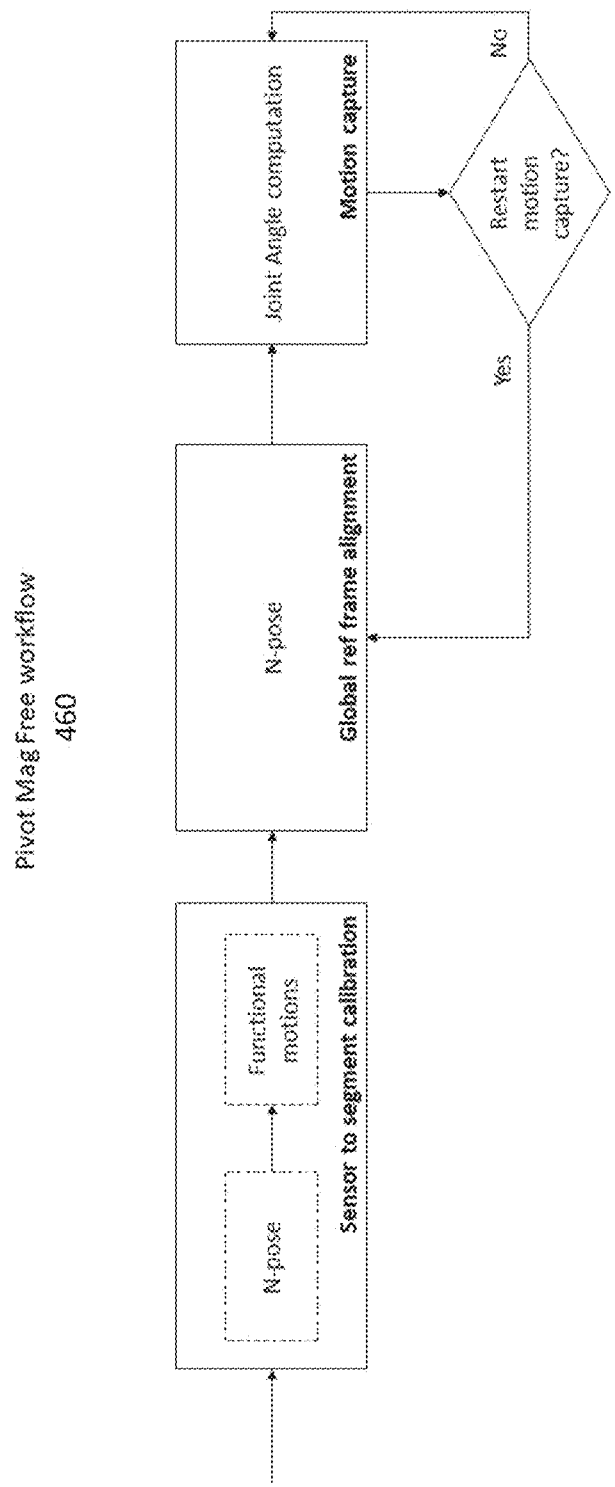
FIG. 4I shows a flowchart or process implemented in PIVOT Mag Free biomechanical protocol.

FIG. 4I shows a flowchart or process 460 implemented in PIVOT Mag Free biomechanical protocol. The very first phase is represented by the STS calibration, which consists in the first N-pose plus the functional motions. Then, to start a new motion capture session, sensor fusion algorithms are started. Since the user is supposed to stay in N-pose, it is possible to compute the global reference frame alignment described above. After that is accomplished, the real motion capture can start, with the joint angles computation as described in the formula above. Every time that the motion capture needs to be restarted, the user needs to go back to the global alignment stage to recompute the global reference frame alignment.

As the background application scenario involves the chance of an orientation drift, the yoga poses detection and classification algorithm must rely on measures unaffected by such errors. In one embodiment, a yoga pose is approximated with a quasi-static condition lasting for more than a second, it is then possible to exploit accelerometers data to compute body segments' attitude, thus inferring user's current pose in real time. A detection algorithm, also referred to herein as TuringSense Pose Detection Algorithm (TSPDA) is composed by the following sub-components or steps:

1) a model of each pose is detected, the model can be based on unprocessed accelerometers data or attitude angles, where the model may also comprise specific tolerance bounds for every body segment;
2) an algorithm capable of detecting user's absence of significant motion over a pre-defined time window in real-time;
3) an algorithm capable of extracting body-segments attitude angles from raw accelerometers' data, when the user is classified as 'still' or 'not moving' by the algorithm mentioned in (2);
4) a classifier capable of comparing body-segments attitude angles computed in (3) with the pose-models mentioned in (1), the classifier identifies in real time if the user is assuming one of the poses defined in the model databased (1). Even if no pose is detected, the classifier will detect a pose closer to the user's body configuration. The classifier is designed to be capable of improving the classification using the current 3D joint angles computed by the Mag Free algorithm;
5) a specific scoring system to provide the feedback on how much the user was close to the pose detected on (4), where the scoring system algorithm provides:
a bounded (i.e., 0%-100%) score describing the overall user ability to match the reference pose
a bounded (i.e., 0%-100%) score describing, for every body segment, the user's ability to match the reference pose.

Every pose to be detected will be modelled and described, based on the data collected with the TS Mag-Free system, in terms of: body segments attitude, body segments-specific attitude tolerances, body segments raw accelerations, body segments-specific raw accelerations tolerances, 3D joint angles, and joint-specific 3d joint angles tolerances and statistical weights.

Figure 5A:
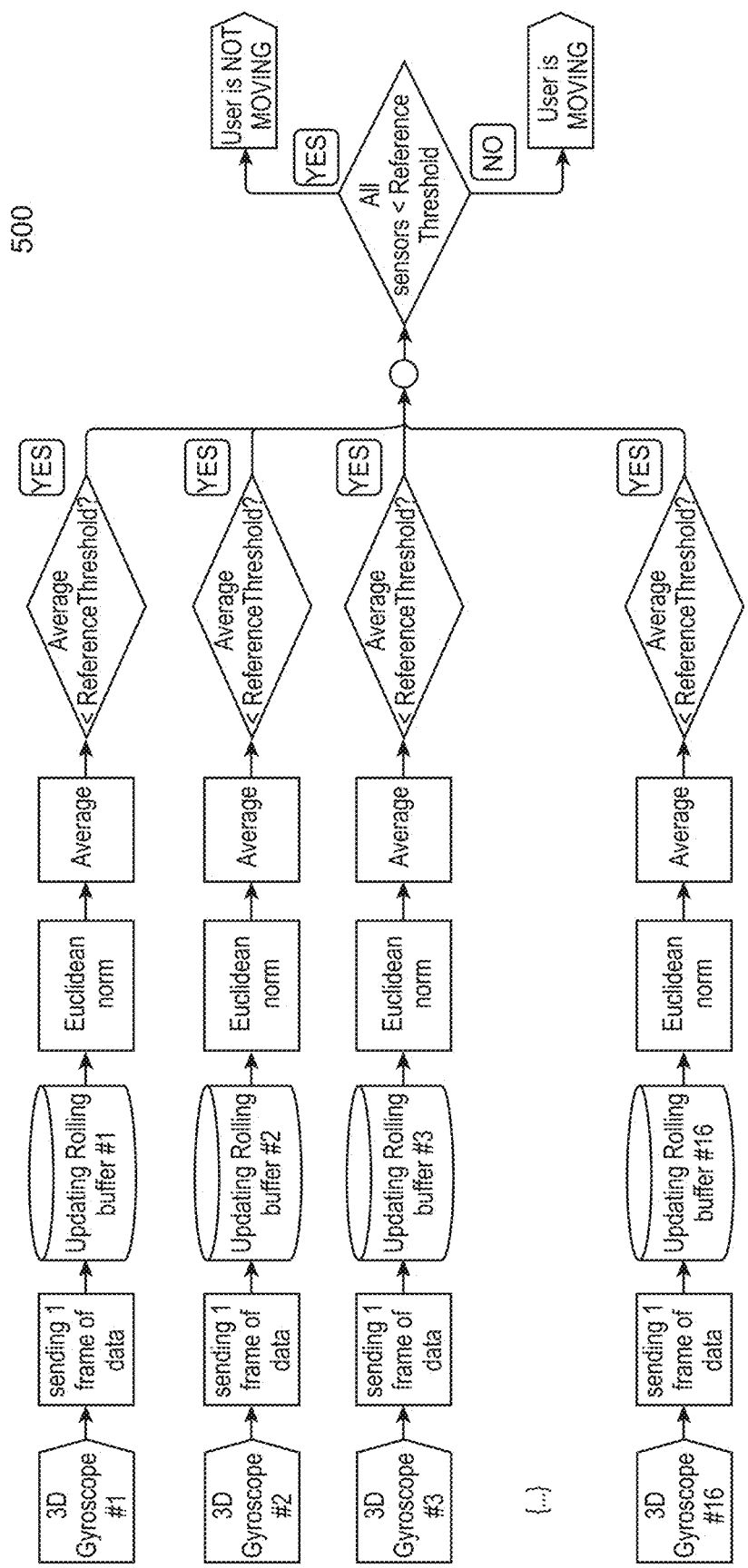
FIG. 5A shows a flowchart or process of detecting stillness (no motion) in a user.

An algorithm, also referred to as Body-Motion Detection Algorithm, is designed to collect and update in real time a rolling buffer of gyroscopes' data; the length of such buffer is pre-defined (e.g., 1 second), but can be changed at any time during the recording. Data is collected from the sensors placed on or near designated body segments of a user. Once the analysis buffer is filled (e.g., after the first second of recording), gyroscopes data is postprocessed, averaged and compared against pre-defined thresholds. If the current post-processed and averaged gyroscopes data coming from all involved body segments is found lower than the pre-defined thresholds, the user's state shall be classified as "not moving". Only if the user's state is classified as "not-moving", the pose detection and classification will proceed further with the above steps (3) (4) and (5). FIG. 5A shows a flowchart or process 500 of detecting stillness (no motion) in a user.

An algorithm, also referred to as Body Segments' Attitude Estimation Algorithm, is designed to collect and update in real time a rolling accelerometers data buffer of a pre-defined length (i.e., 1 second). The data is collected from the Sensors placed on all user's body segments involved by the TS Mag Free protocol. In the same fashion, if already present, 3D joint angles data can be collected as well to improve the classification. Once the analysis buffer is filled (i.e., after the first second of recording), accelerometers data will be postprocessed and averaged.

Figure 5B:
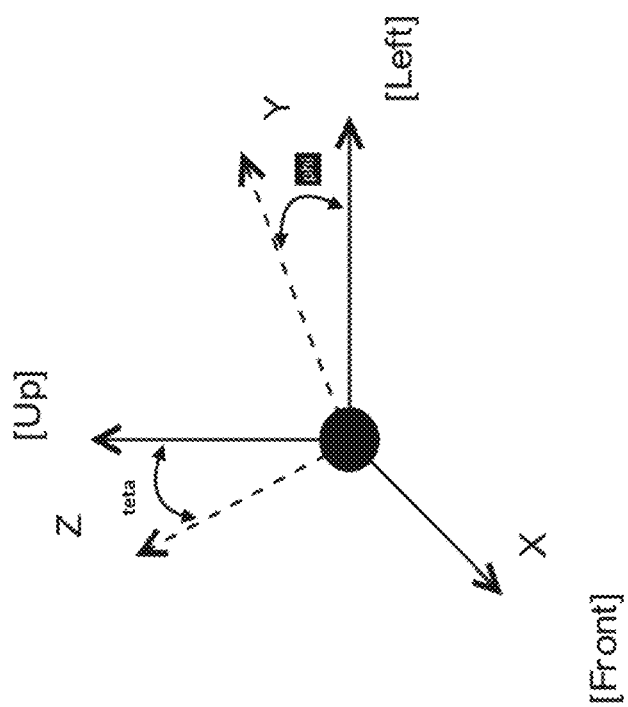
FIG. 5B shows the computations of attitude angles (phi, teta) for each body segment.

Knowing the sensors orientation a-priori, accelerations can be expressed in the body-segment system of reference, the attitude angles (phi, teta) for each body segment are computed as shown in FIG. 5B:

$$phi = \tan^{-1}\left(\frac{a_x}{\sqrt{a_y^2 + a_z^2}}\right)$$

$$teta = \tan^{-1}\left(\frac{a_y}{\sqrt{a_x^2 + a_z^2}}\right)$$

Figure 5C:
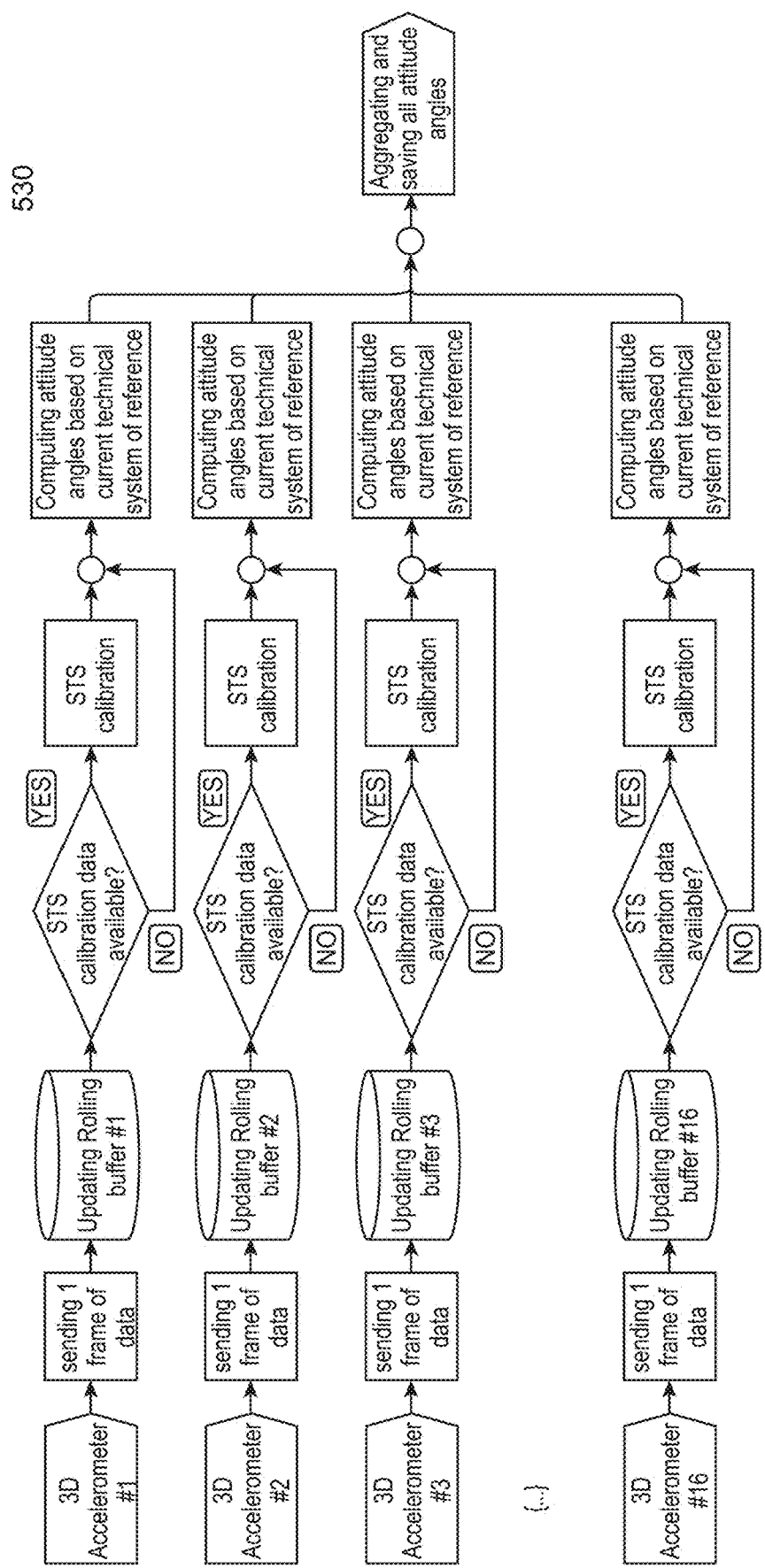
FIG. 5C shows a flowchart or process of performing attitude angle estimation.

Attitude angles (phi, teta) for each body segment are stored and used next in the above sub-components (4) (5) for the pose classification and scoring. If present, 3D joint angles are stored as well. FIG. 5C shows a flowchart or process of performing Attitude Angle Estimation.

All parameters computed in step (3) are compared with the models for all the poses described in step (1). In order to compute the degree of matching between one user's body segment and the reference value contained in one reference pose model (1), separate methods are applied:

M1:
a) divide user's body segment averaged 3d acceleration by its Euclidean norm

|a|=norm(a);

b) compute the angle between the 3d vector |a| and the 3d vector contained in the reference pose (|aref|)

delta_angle=a cos(|a|DOT|aref|)

where DOT is the dot product.

M2 2:
  a) compute the difference between the body segments' attitude angles (teta, phi) calculated in (3) and the corresponding values saved in the reference pose model (1).
M3: similar to M1 1, if available, compute the overall degree of the agreement between the user's joint angles and the values saved in the reference pose model.

Figure 5D:
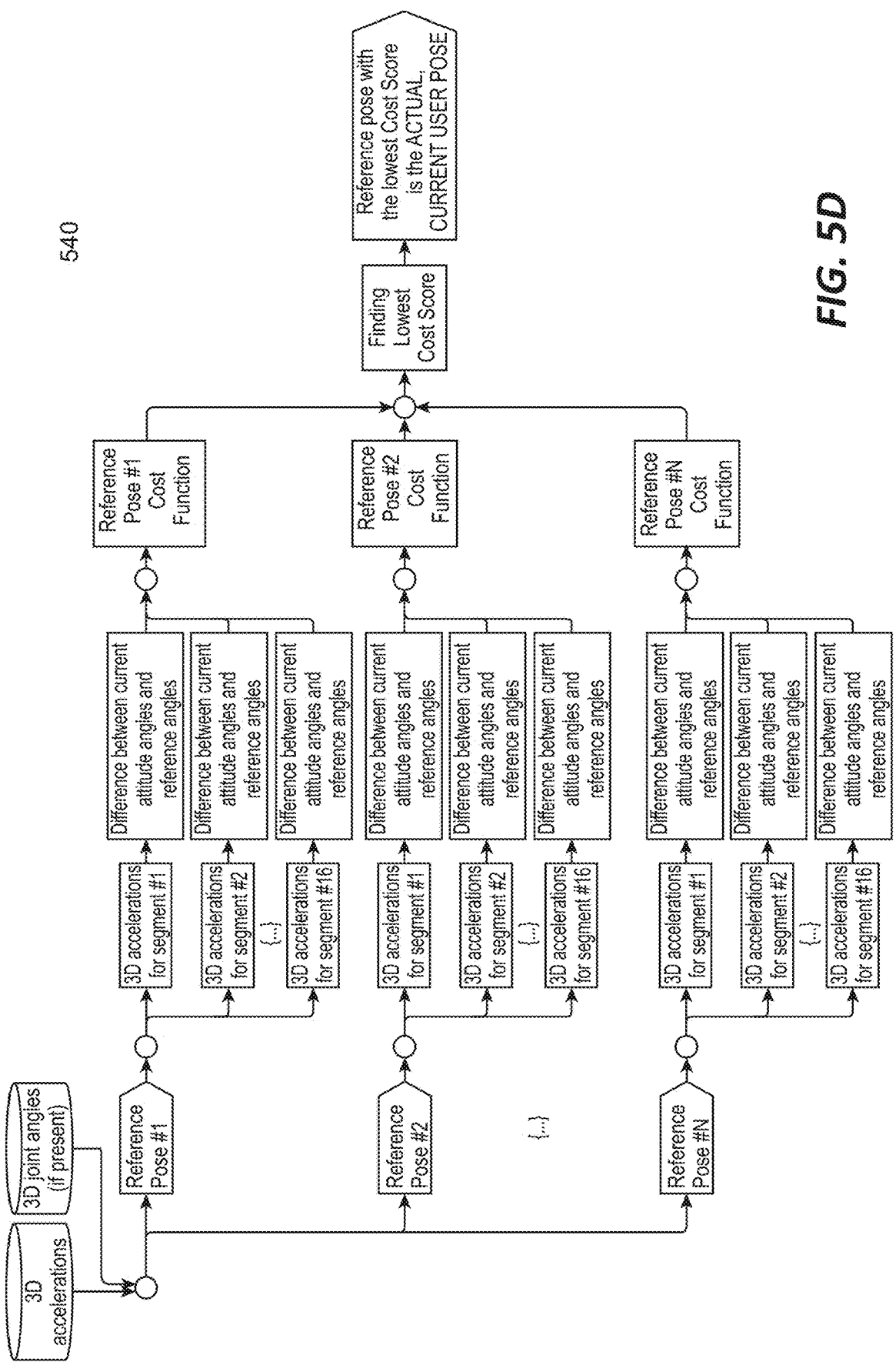
FIG. 5E shows a flowchart or process of estimating user pose scoring.
FIG. 5F shows an exemplary sigmoid transfer function.

Once (M1), (M2), and eventually (M3), are computed for each body segment, their values are combined into a per-pose cost function which will assign an overall agreement score among the user's current pose and the pose model used for the comparison. Once all pose models (1) agreement scores have been computed, the model pose with the highest agreement score is selected as the user's current pose. FIG. 5D shows a flowchart or process 540 of Reference Pose Classifier.

Once the current user's pose is classified (4) and matched with a pose model in the reference pool (1), it is possible to compute the following outcomes:
  O1: current user's pose MATCHES or NOT MATCHES the reference pose model;
  O2: overall pose matching score; and
  O3: per-body segment matching score.

Comparison metrics computed in (4) are combined in a segment- and pose-specific cost function representing the degree of matching between the user's current, actual pose and the reference.

In the following diagram is described the classification of every user body segment into:
  1) matching/not matching the reference pose model (Cost_ score–O1, O2)
    cost_score=1 indicates that the body segment matches the reference model
    cost_score=0 indicates that the body segment does not match the reference model
  2) Overall percentage of agreement with the reference pose model (PA %—O2)

Figure 5E:
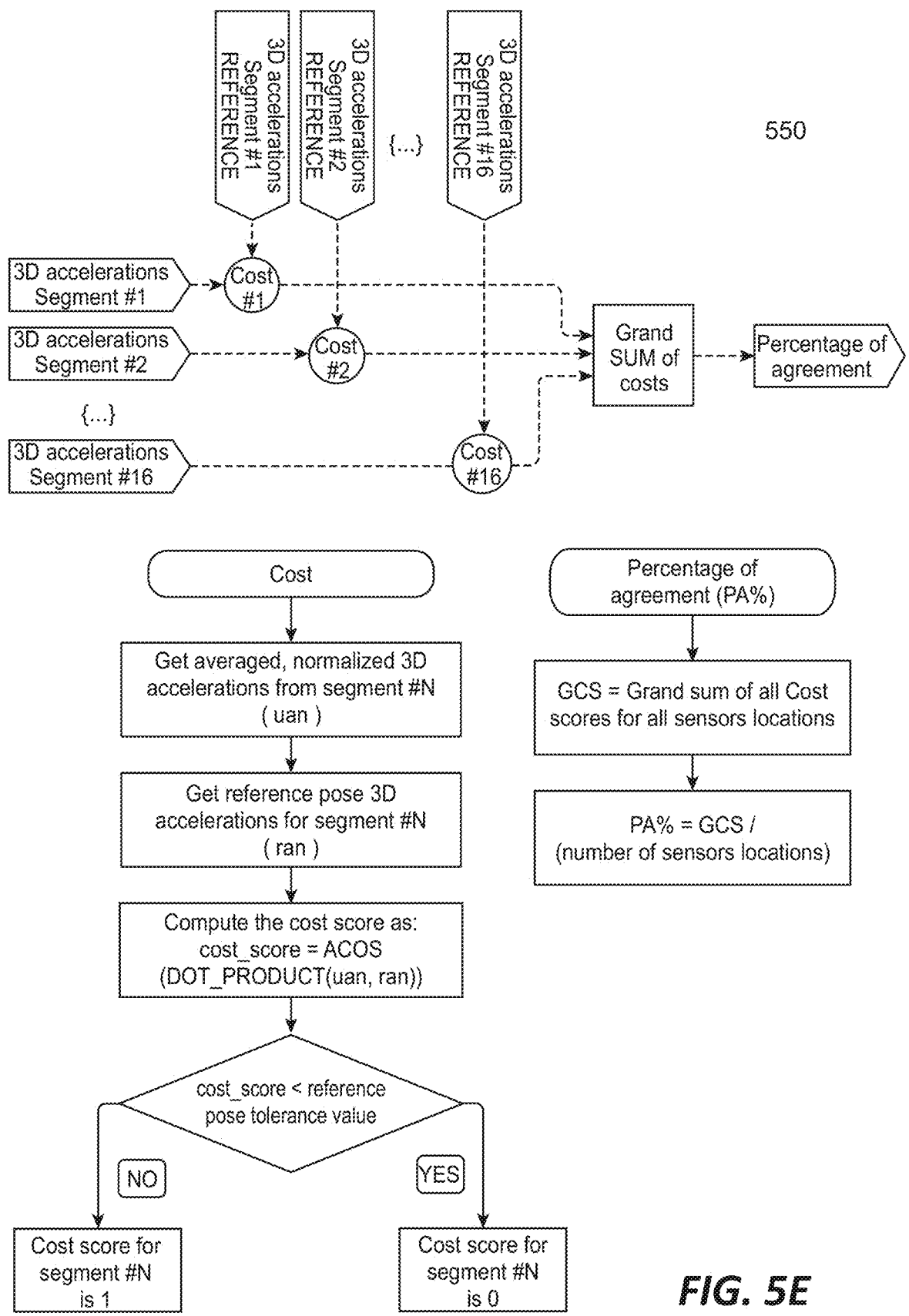
Figure 5F:
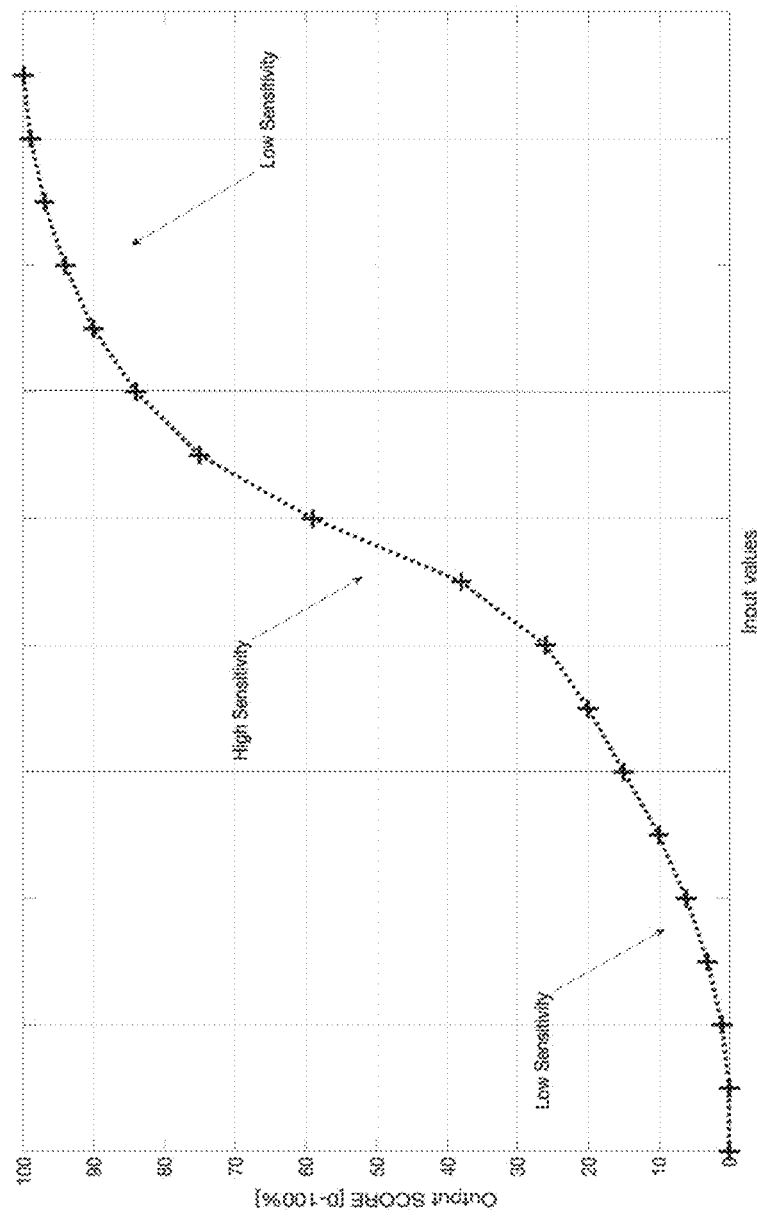

Once the current user's pose is classified in step (4) and matched with a pose model in the reference pool (1), it is possible to compute the following outcomes as shown in a flowchart or process 550 FIG. 5E. Depending on the method applied, the per-segment and per-pose cost function can be unbounded and ranging from minus-infinity and plus-infinity. In order to normalize the score and make it at the same time comparable inter-user and inter-session and easily interpretable, a segment-specific and pose-specific sigmoid transfer function is applied to the cost function in order to translate the original unbounded values into bounded and easy-readable ones (e.g., 0%-100%). The sigmoid transfer function can be calibrated on the user specific level of ability in performing the pre-defined pool of poses (i.e., novice, amateur, expert, professional), so that the final score can be adapted to his experience progression.

As described above, one of the strategies to deal with the angular drifting error in PIVOT Mag Free is the pose reset. The idea is to exploit those moments while the user is doing a yoga pose (and it is still) to restart the sensor fusion algorithms. Note that the user stillness alone is not a sufficient condition to apply a sensor fusion reset in the mag free scenario. In fact, after the reset, each sensor fusion algorithm will take a different global reference frame. Therefore, the same global reference frame alignment procedure explained above needs to be performed. For doing so, it is necessary that the physical orientation of the sensor is known at the time the sensor fusion algorithm is reset. There are two reset strategies possible and hereafter they are called as soft pose reset and hard pose reset.

FIG. 6A shows a workflow or process 600 of soft pose reset. The process 600 may be launched every time a user is detected to be still. In that time instant, the current orientation of all the body segments of the user is stored and a sensor fusion algorithm reset is issued. The quaternions produced after the sensor fusion reset will be matched with the stored orientations before the reset in order to compute the previous global reference frame alignment procedure as described above. After the compensation, the motion capture session can be resumed.

The process 600 takes advantage in accuracy through the sensor fusion reset. However, it must be noted that the resuming condition for the sensor fusion algorithms could already be affected by some drift. Repeating this procedure many times may still result in a slow accumulation of drifting errors. In fact, the expectation of the soft pose reset is to make the drift slower but not to produce drift-less motion capture. Despite this drawback, however, this procedure is relatively simple to be implemented.

Figure 6B:
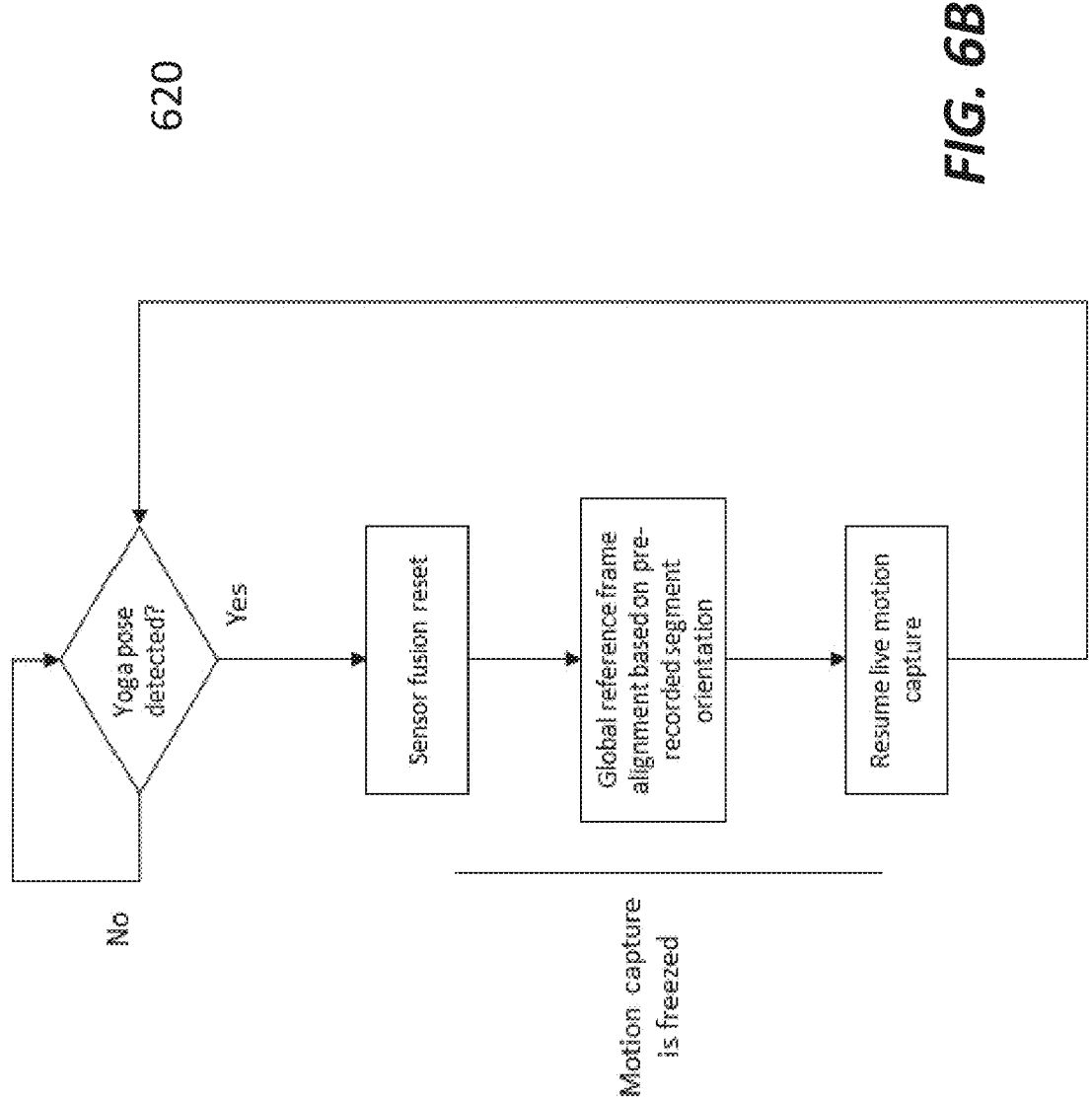
FIG. 6B shows a workflow or process of hard pose reset.

Another reset solution is implemented in PIVOT Mag Free in order to provide a drift-less estimate over a longer time window, which is called hard pose reset. This procedure is very similar to the soft pose reference, as shown in FIG. 6B with the following two main differences:
  1. The reset must be triggered when the user is in a specific yoga pose (N-pose or yoga pose), the yoga pose detector described above is therefore used to trigger the hard pose reset.
  2. The global reference frame alignment is computed based on reference (pre-recorded) body segment orientations. These reference poses can also be acquired with other (more accurate) motion capture systems, like stereo-photogrammetric systems.

The advantage of the hard pose reset over the soft pose reset is that not only sensor fusion algorithms are reset, but the reference pose used to resume the mocap is pre-recorded. This means that the reference pose is drift free, maybe even acquired with high accuracy systems. For this reason, triggering this procedure multiple times during will result in drift-less motion capture. However, this procedure is more complex and requires a specific yoga pose detection algorithm on top of it.

The description of the present invention is now focusing on what is referred herein as Double Tap Gesture Detection. The purpose of double tap gesture detection is to detect in real time a user performing specific gestures while wearing smart-clothing. Detected gestures are used to trigger specific actions on the App as instance play, and to pause the video. For double tap, the technique is intended to detect the act of tapping twice with one of the user hands' palm or fingers over one body segment. It is also possible to detect double tapping gestures over objects such as desks or walls. At least one involved body segment (the "active" or "tapping" hand and the "passive" or "tapped") is supposed to be instrumented with a smart-clothing.

The technique is based on the analysis of accelerometers and/or gyroscopes data coming from MEMS (micro electro mechanical systems) or NEMS (nano electro mechanical systems) contained within the smart clothing. In order to allow the detection of the broadest possible spectrum of combinations of tapping locations, data from all available sensors locations will be acquired and processed. This will allow to detect any combination of double-tapping events, both being performed with an instrumented body segment over another (T2), or with one instrumented body segment over a non-instrumented one (T1).

Examples of a tapping event happening between two instrumented body segments:
- T2.1: instrumented left hand double-tapping on instrumented right hand
- T2.2: instrumented left hand double-tapping on instrumented chest
- T2.3: instrumented right hand double-tapping on instrumented left forearm Examples of a tapping event happening between one instrumented body segment and a non-instrumented body segment/object:
- T1.1: instrumented left hand double-tapping on non-instrumented right hand
- T1.2: non-instrumented left hand double-tapping on instrumented chest
- T1.3: instrumented left hand double tapping on the desk
- T1.4: instrumented right hand double tapping on the wall It is possible to detect only double taps in which the time intercurring the two tapping events is lower than a predefined threshold; such threshold can be altered while the algorithm is already running.

The technique is composed by a chain of 4 specific functional blocks:
- FB1: sensor data collection and buffering;
- FB2: sensor data processing;
- FB3: Double-Tap event detection on a single sensor; and
- FB4: Double-Tap events aggregator and classifier.

Figure 7A:
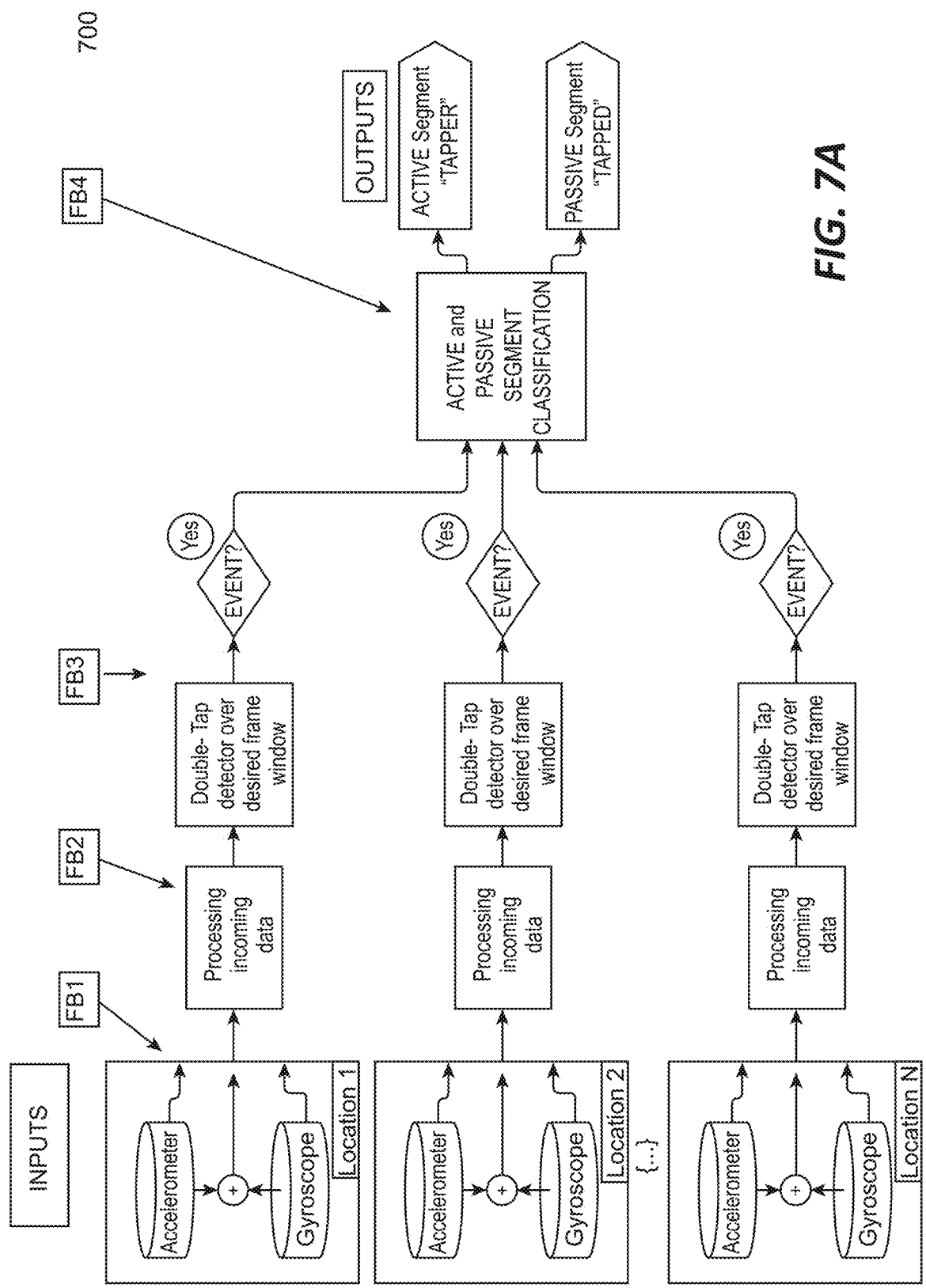
FIG. 7A shows a flowchart or process of double tap gesture detection.

FIG. 7A shows a flowchart or process 700 of double tap gesture detection. Data from all sensors locations (e.g. left hand, right hand, chest) is collected and streamed to the detection algorithm using one rolling data buffer (FIFO) per sensor, per location. The buffer will contain as much data as the maximum allowed duration of the double tap. As instance, considering:
- 100 Hz sampled data; and
- a maximum allowed time of 1 second for the second tap to happen.

The technique is composed by a chain of 4 specific functional blocks. The rolling buffer contains 100 (100 Hz*1 sec) samples per satellite location. For every sensor location, the algorithm will be aware of the number and type of sensors present:
- S1: Accelerometer
- S2: Gyroscope
- S3: Accelerometer AND Gyroscope Depending on the scenario (S1-S3), the algorithm will apply different, specific signal processing methods (e.g., high-pass or low-pass filtering) in order to remove spurious noise and to isolate only the signals' spectra band required. Additional postprocessing methods can be applied in order to maximize the chances of double tap detection; in the following examples:

Gyroscopes data will be processed to compute the frame-by-frame norm; norm is the frame-by-frame Euclidean norm of the gyroscope data.

$$|g| = \sqrt{g_x^2 + g_y^2 + g_z^2} \quad \text{(f1)}$$

Accelerometers data will be processed to compute the normalized jerk; normalized jerk is the Euclidean norm of the time-derivative of the acceleration data.

$$\underline{j} = \frac{da\_(t)}{d(t)} \quad \text{(f2a)}$$

$$|j| = \sqrt{j_x^2 + j_y^2 + j_z^2} \quad \text{(f2b)}$$

After processing the incoming signal, an iterative, dynamic threshold approach will be applied on the buffered and processed data. After setting the amplitude threshold value, a local maxima detection algorithm will seek the buffered data for signal peaks above the set threshold. A local maximum is identified by the following rules:
- R1: three subsequent frames above the set threshold
- R2: data at frame t has a lower amplitude than data at frame t+1
- R3: data at frame t+1 has a higher amplitude than data at frame t+2

Considering the number of above-threshold local maxima found, the signal can be classified as:
- E1: no local maxima are found higher than the threshold;
- E2: 1 local maximum is found higher than the threshold;
- E3: 2 local maxima are found higher than the threshold; and
- E4: more than 2 local maxima are found higher than the threshold.

If 2 or more local maxima are found (E3, E4), the iterative process will stop.

If 2 local maxima are found (E3), a double tap event occurring in the current location is identified.

If 1 or none local maxima are found (E1, E2), the amplitude threshold value is lowered by a predefined value (e.g., 5%) and the local maxima algorithm is iterated again.

This method is iterated until one of the following events occur:
- E3: 2 local maxima are found;
- E5: the amplitude threshold reached the lowest value allowed (e.g., 200 deg/sec).

Figure 7B:
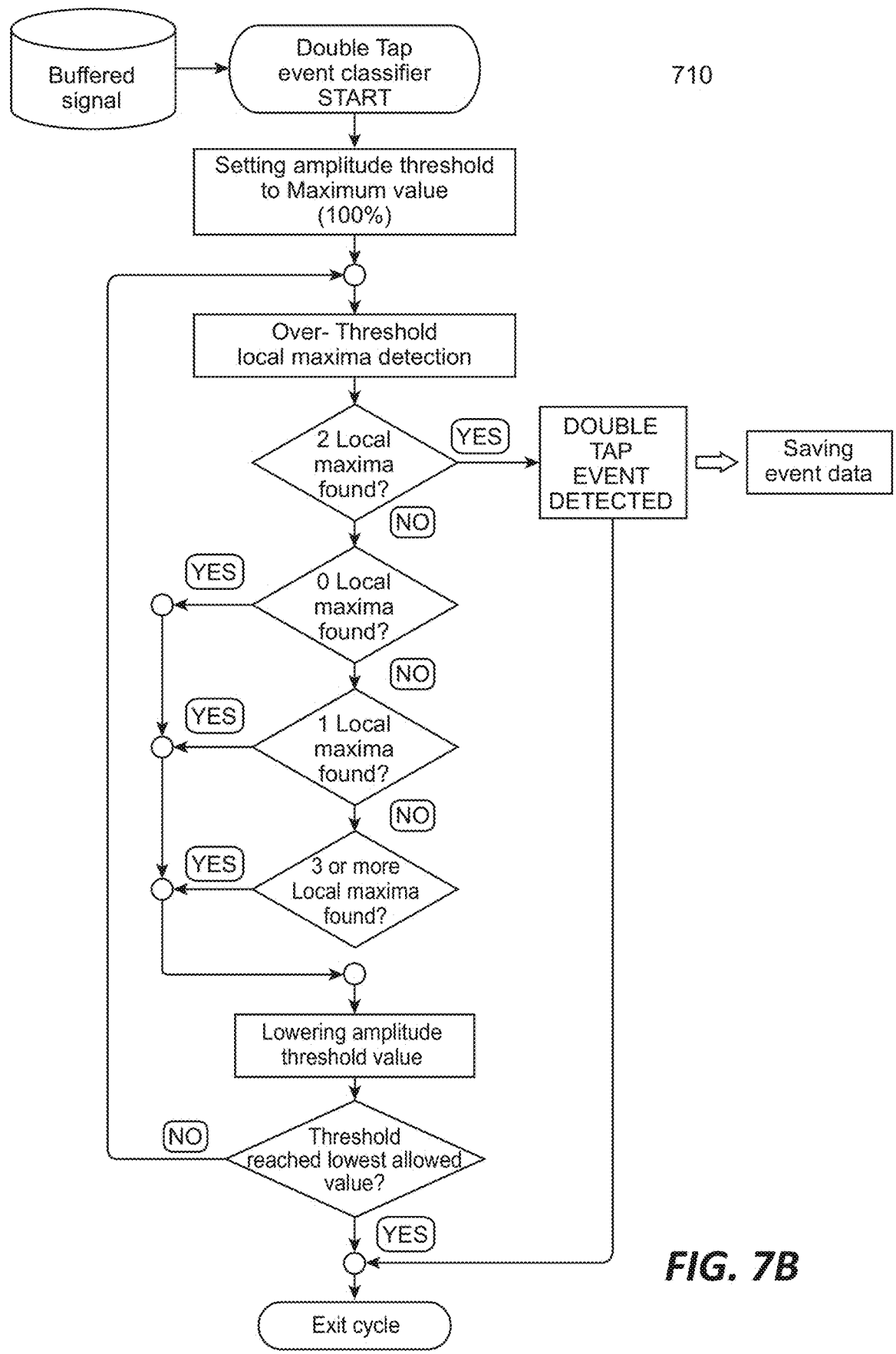
FIG. 7B shows a flowchart or process of double tap event detection.
Figure 7C:
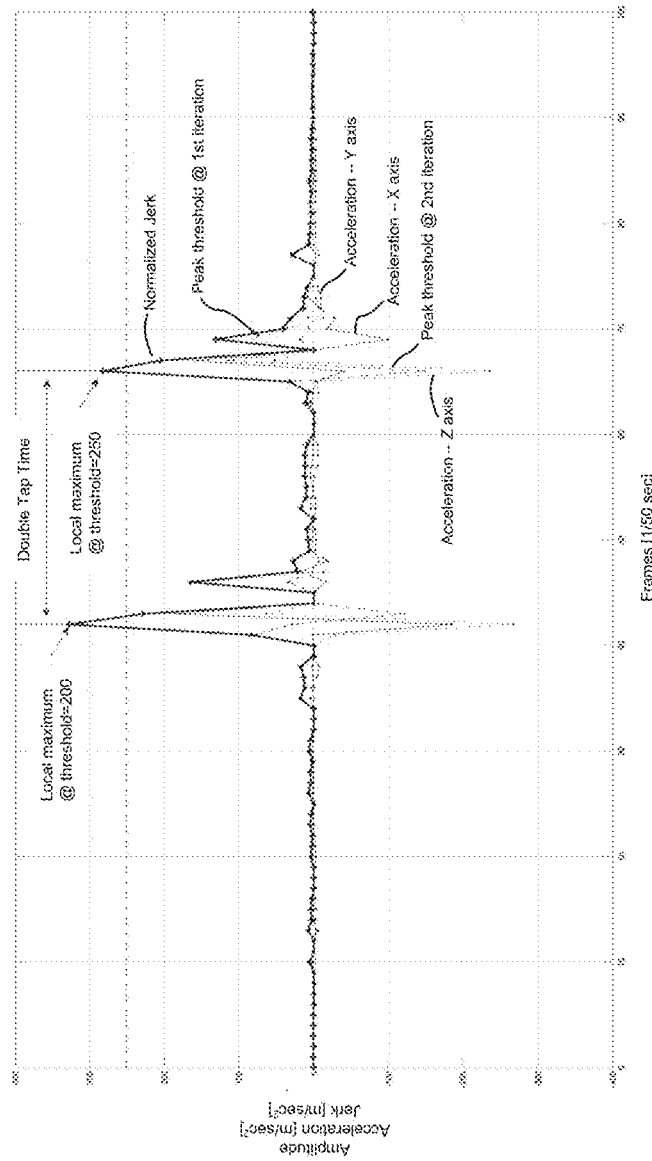
FIG. 7C shows an example of double tap event found on accelerometer data after applying two different peak thresholds.
Figure 7D:
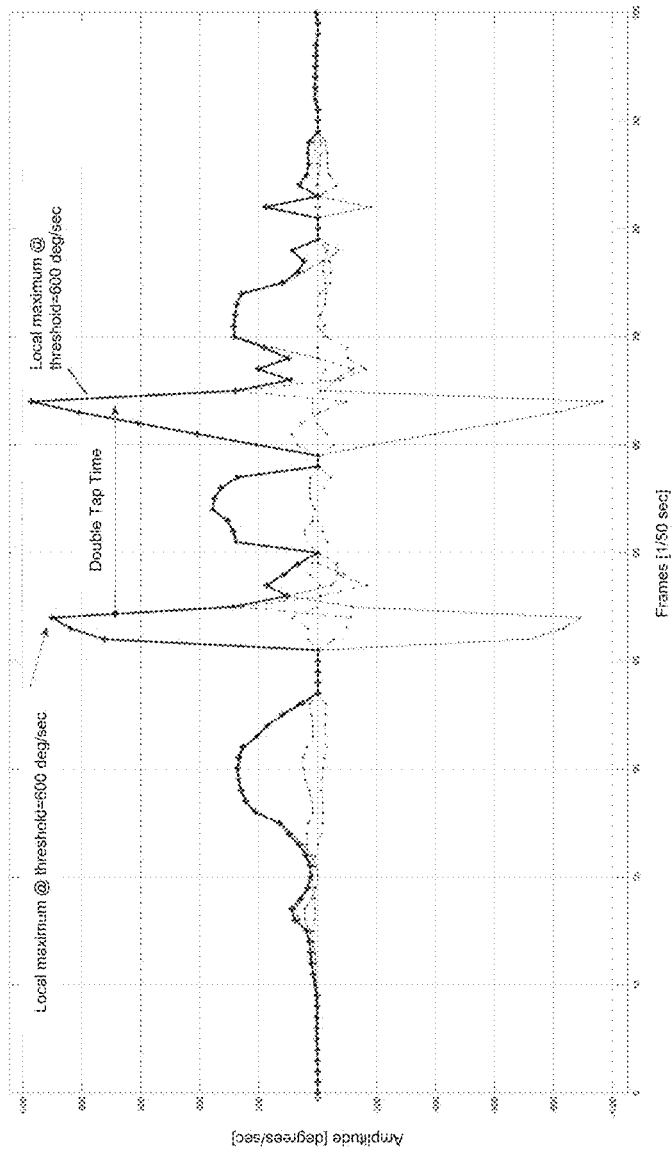
FIG. 7D shows an example of double tap event found on gyroscope data.

FIG. 7B shows a flowchart or process 710 Double Tap Event Detection Flowchart. FIG. 7C shows an example of double tap event found on accelerometer data after applying two different peak thresholds. FIG. 7D shows an example of double tap event found on gyroscope data.

Based on the events occurred (E1-E4), a first classification of the signal takes place on the sensor data:
- E1: NO DOUBLE TAPPING occurred, as no related signal's pattern landmarks are found
- E2: NO DOUBLE TAPPING occurred, as no related signal's pattern landmarks are found
- E3: DOUBLE TAPPING EVENT OCCURRED
- E4: NO DOUBLE TAPPING occurred, as the signal's pattern found is related to motion noise or non-conforming gestures (e.g., triple taps, hands shaking).

If a double tap event is found on 2 or more sensors locations, the data from the sensors which generated the events is passed to the active/passive segment classifier.

The active/passive segment classifier will analyze the data and provide:
- O1: if present, which sensor location was the "active" tapping segment (or "tapper")
- O2: if present, which sensor location was the "passive" tapping segment (or "tapped").

Figure 7E:
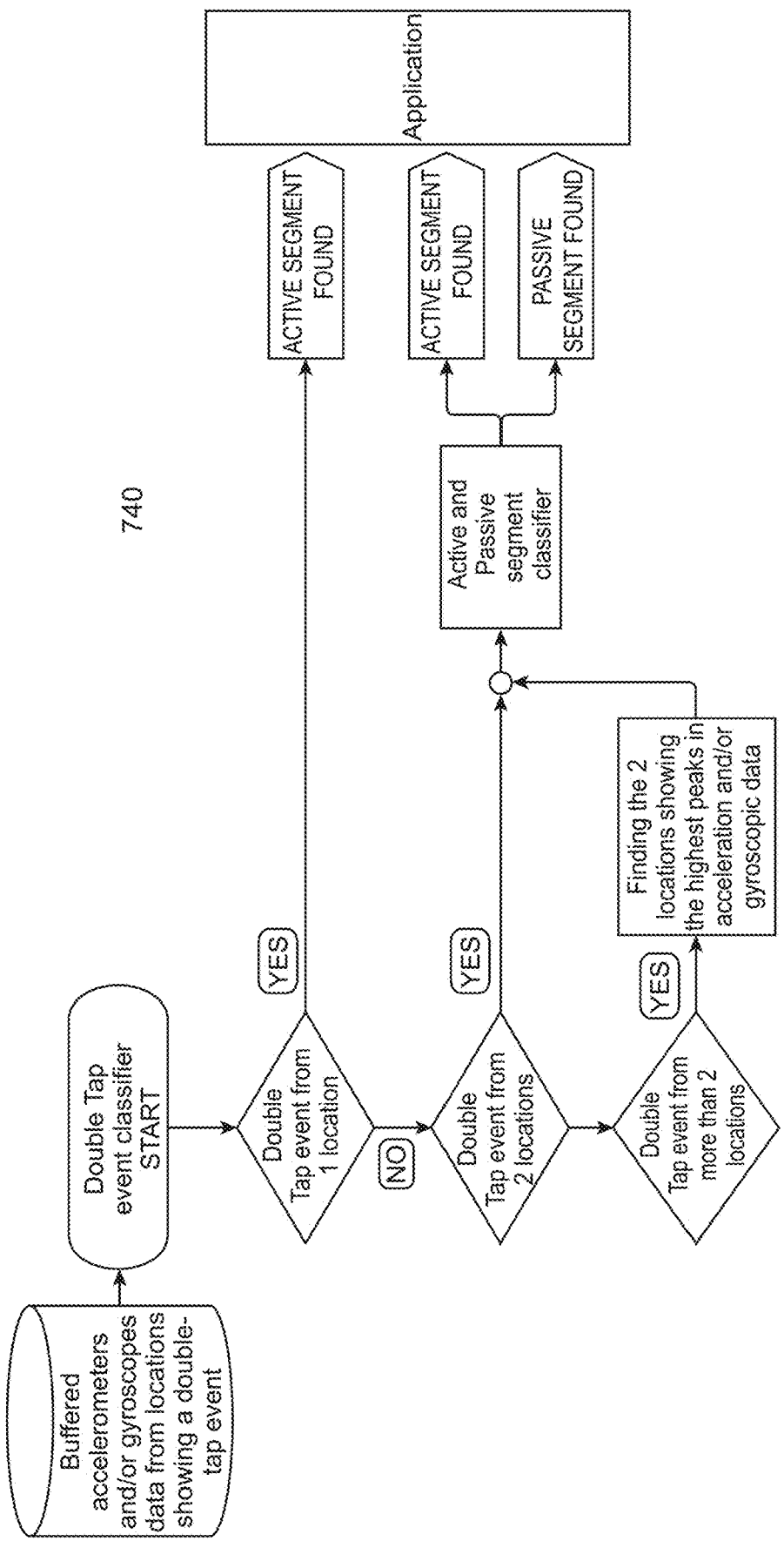
FIG. 7E shows a flowchart or process of double tap event details classifier.

If more than two sensors locations generated the double tap event (E3), as instance due to a particular fast user motion, the classifier will be capable of detecting the actual O1 and O2 by analyzing and comparing signal patterns characteristics from all sensors locations which generated the double tap event (E3). FIG. 7E shows a flowchart or process 750 of double tap event details classifier. Once the double-tapping event is detected and classified in all of its parameters (time, O1, O2), the algorithm communicates the decoded event to the App, which applies the specified action.

As instance:
Example 1:
Tapping Time: 0.4 seconds;
O1: left hand is the active tapper;
O2: right hand is the passive tapper; and
This combination of events is associated to the app's command: "Stop video".
Example 2:
Tapping time: 0.5 seconds;
O1: right hand is the active tapper;
O2: no events; and
This combination of events is associated to the app's command "Resume Video".

Figure 8A:
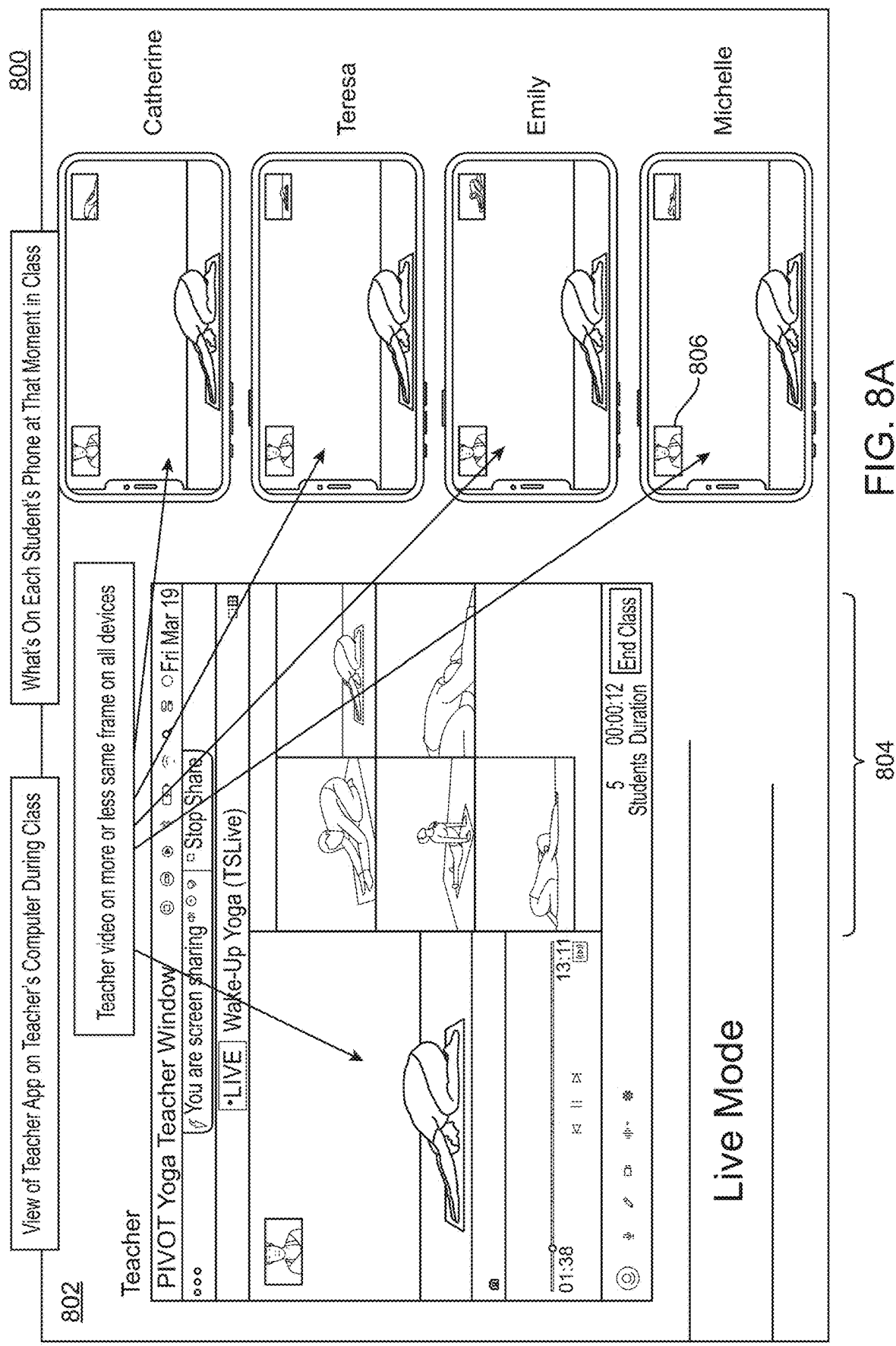
FIG. 8A showing a screen shot of an exemplary view by an instructor (or trainer) teaching a class (e.g., Yoga or dancing) according to one embodiment of the present invention.

Referring now to FIG. 8A showing one embodiment of the present invention, it is a screen shot 800 of an exemplary view by an instructor (or trainer) teaching a class (e.g., Yoga or dancing). The screenshot 800 includes a main view 802 being mirrored in a plurality of connected devices by trainees. The main view 802 shows motions performed by an authoritative instructor (e.g., the trainer himself or a selected instructor from a library). There are also a set of gallery views 804 providing monitoring video of each or all of the trainees performing the same following the instructor. At any moment, the trainer can select one of the gallery views 804 and examine how the corresponding trainee is doing. The selected gallery view may be privately viewed by the trainer or shared with some or all of the trainees in the class or even recorded for sharing late.

The students or trainees meanwhile see the teaching video play along with an inset video 806 of the trainer as the trainer guides them. According to one embodiment, each student pre-records the video of the instructor for the class as part of registration. Then during class, the teaching video is synched between the instructor and the students using periodically broadcasted WebSocket messaging ("heartbeat") sent over the Internet that keeps each device used for the class to within a (threshold) predefined number of frames of each other, taking the network latency into calculation. In any case, the instructor can stop, start, annotate, and scrub the teaching video and the synch is maintained as the teacher app is continuously sending out a "heartbeat" signal that keeps all the student devices synchronized within a frame or two. This works not just for students in the class, but also students who join the class late or who lose then regain their Internet connection. Also, if the trainer has entered pose titles for the teaching video, she can, during class, skip ahead to each pose, as if they were chapters in the video.

Figure 8B:
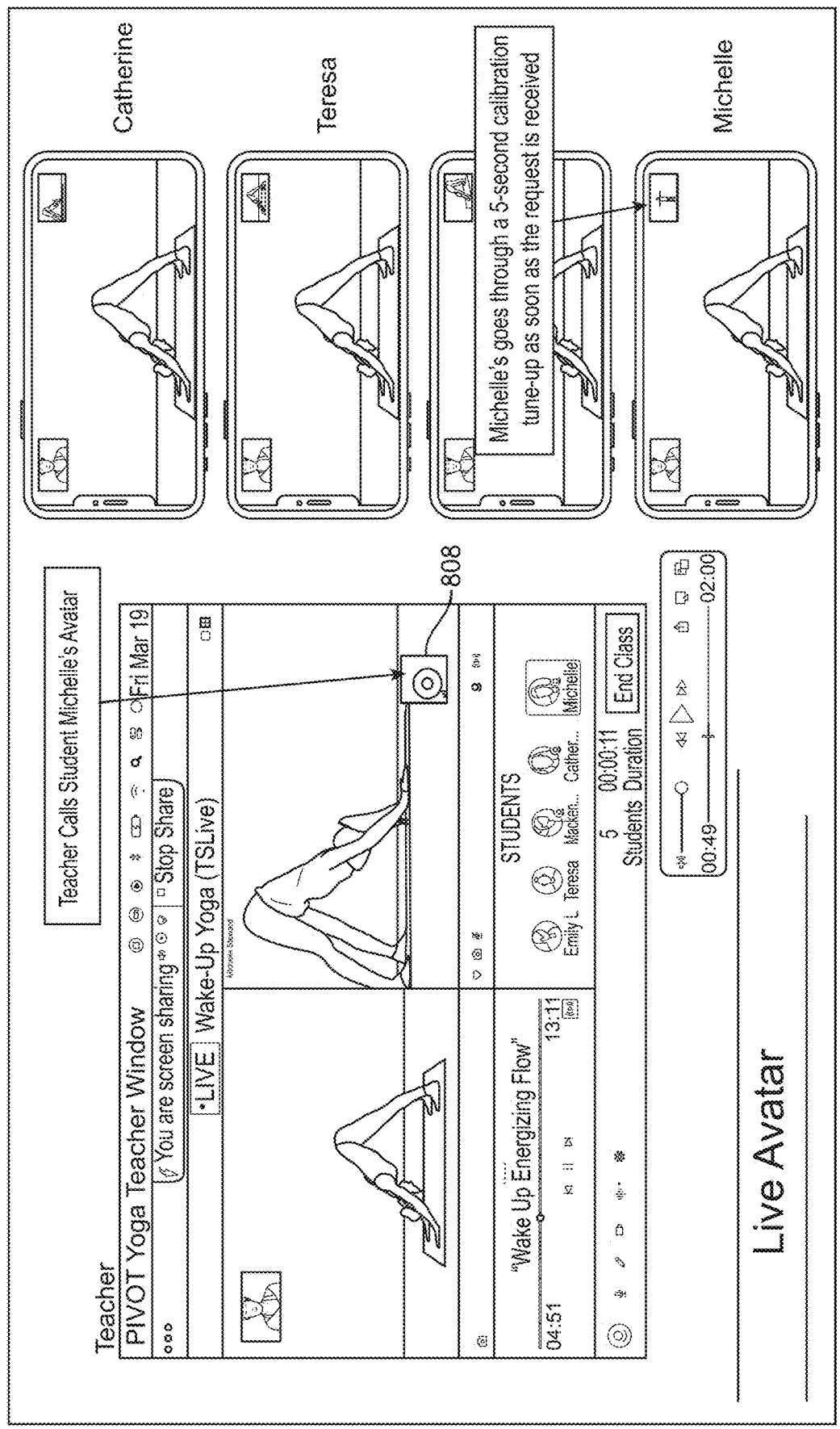
FIG. 8B shows that one of the gallery views is selected, instead of determining how the trainee is doing visually in the video, the trainer chose a function 808 that initiates the generation of an avatar representing the trainee.

FIG. 8B shows that one of the gallery views is selected. Instead of determining how the trainee is doing visually in the video, the trainer chose a function 808 that initiates the generation of an avatar representing the trainee. The avatar in 3D is generated based on the sensing data from the sensor modules in the clothing worn by the trainee as described above. The avatar is allowed to be viewed from any chosen perspective on a 2D display. Depending on implementation, the avatar may be generated locally in the computing device used by the trainer or a remote computing device.

Figure 8C:
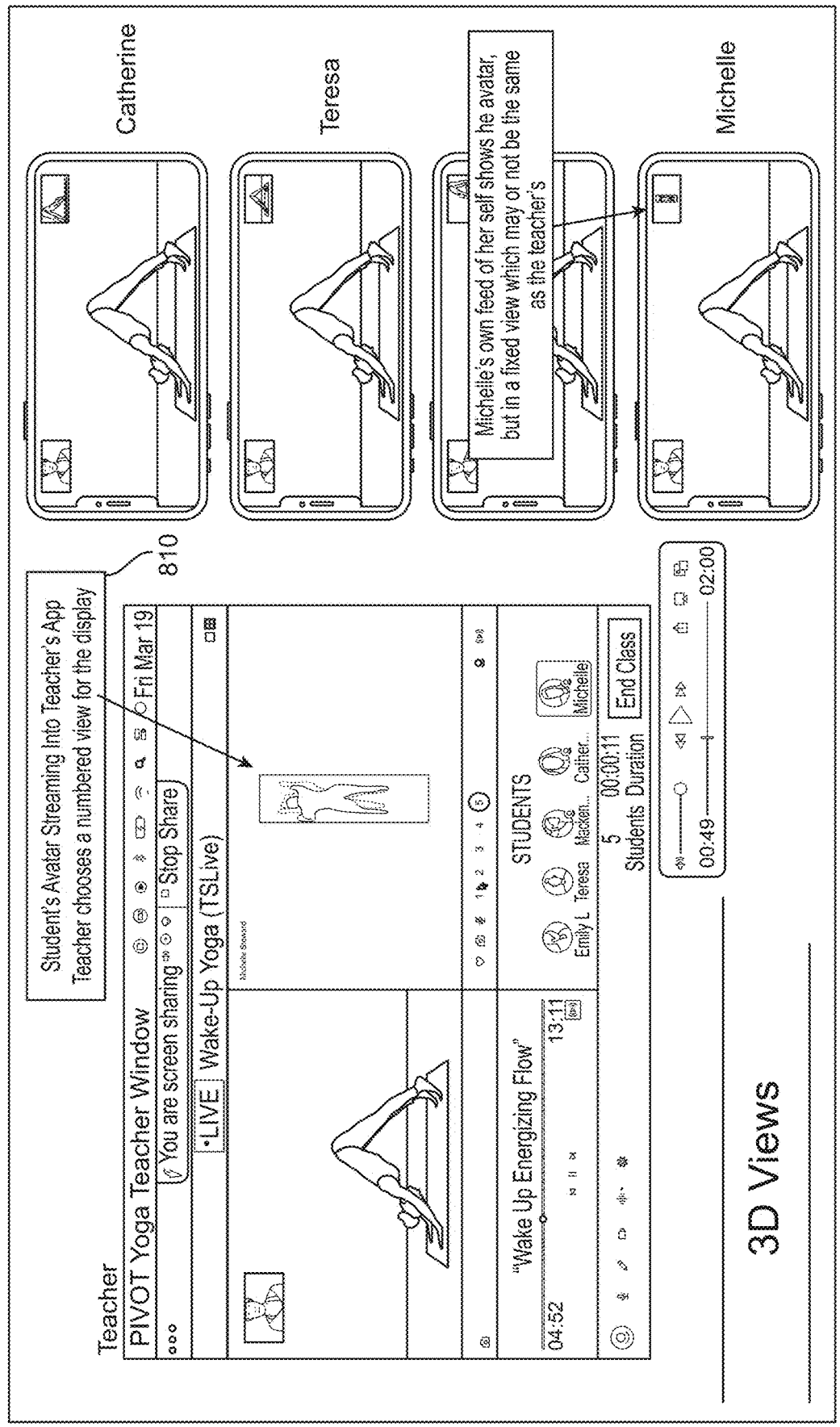
FIG. 8C shows a view in which one avatar is superimposed on another.

FIG. 8C shows a view 810 in which one avatar is superimposed on another. According to one embodiment of the present invention, not only can the avatar representing the trainee be viewed in any perspective, but another avatar representing an instructor can be superimposed thereon so that the trainer can visualize explicitly where the trainee has done wrongly or how the trainee has been or is doing in view of the avatar of the instructor. It shall be noted that the video camera used by the trainee is only used for the trainer to see the presence of the trainee, the video data is not used to generate the avatar of the student. It is the sensing data from the sensors is used to generate the avatar thereof, where the sensors are positioned properly within the clothing worn by the trainee.

In one embodiment, data from each student streams live into the computing device used by the teacher, where the computing device executes one embodiment of the present invention (a.k.a., Teacher App) during class so that the teacher sees a live 3D avatar representing the body movements of each of the students. The teacher can view the avatar from any chosen side, including overhead. There are no cameras involved in generating or viewing the avatar, no furniture blocking the view. The camera with a student may be placed without too much restriction. Further any lighting conditions in a student home would not interfere with the view of a pose of a student to be viewed by the teacher. Essentially, the teacher can analyze the pose of a student regardless where the student performs the motion, and make specific recommendations to the student anytime, during or after the class or session.

According to one embodiment, the pose intelligence is applied to the avatar. For example, in a standing pose, that both feet of the student would not be off the ground, and the priori knowledge is used to filter out any errors that may be received directly from the sensors when generating an avatar of the student. Students in the class can be respectively represented by their avatars, the teacher decides when to display an avatar of a specific student. In one embodiment, each avatar can be instantaneously presented in one of 5 different orthogonal views—front, back, both sides, and overhead, each readily at the command of the teacher. The teacher can click a button to screenshot a moment, either from the teaching video, or video of a student, or a live avatar of the student. This capture forms a frame and then stores it inside the Teacher App (and/or a cloud computer). Any annotations are included along with the screenshot to form a highlight for the student. If any highlights are created by the teacher, she can share all the highlights with students at the end of the class during a Warm Down period at the end of the class. The highlights rotate through in a slideshow that the teacher can stop, skip forward or scrub. Optionally the instructor can email the highlights to one or more students after class with a few clicks.

Figure 8D:
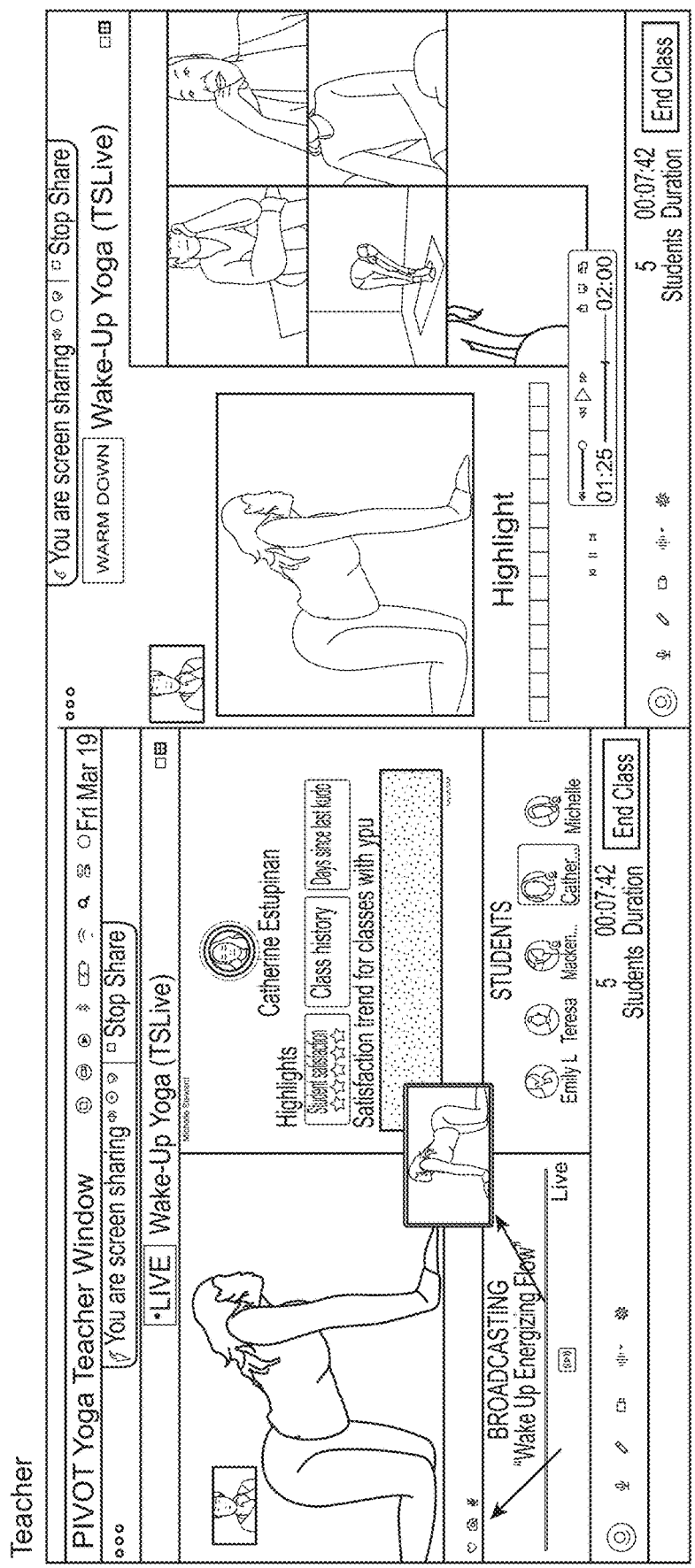
FIG. 8D shows an example of two screenshots from the display used by the teacher during a warm-down session.

FIG. 8D shows an example of two screenshots 812 and 814 from the display used by the teacher during a warm-down session. The screenshot 812 shows that the teacher records or annotates a session of a chosen student having performed or performing some poses remotely. It allows the teaches to rewind the recorded video to illustrate where the student has done incorrectly, which may be based on a view or comparison of the corresponding avatar to that of an instructor. The screenshot 818 shows a plurality of students are watching the same. Essentially, the teacher can share the errors by one student with other students so that all may watch out the same poses if they do the poses again.

Figure 8E:
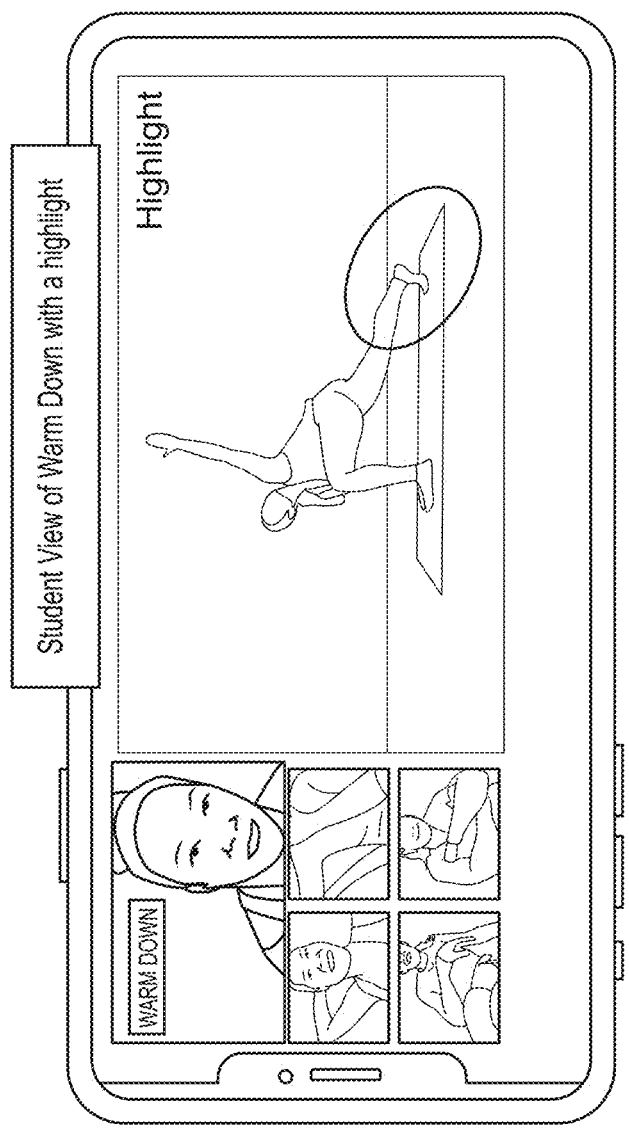
FIG. 8E shows a corresponding view by a student, where the view is synched with the view being viewed or controlled by the teacher.

FIG. 8E shows a corresponding view 820 by a student. The view 820 is synched with the view being viewed or controlled by the teacher. When the teacher points out which body part of a chosen student is posed incorrectly, or highlights the body part, the interactions between the teacher and the student are simultaneously shown on the view 820.

Figure 8F:
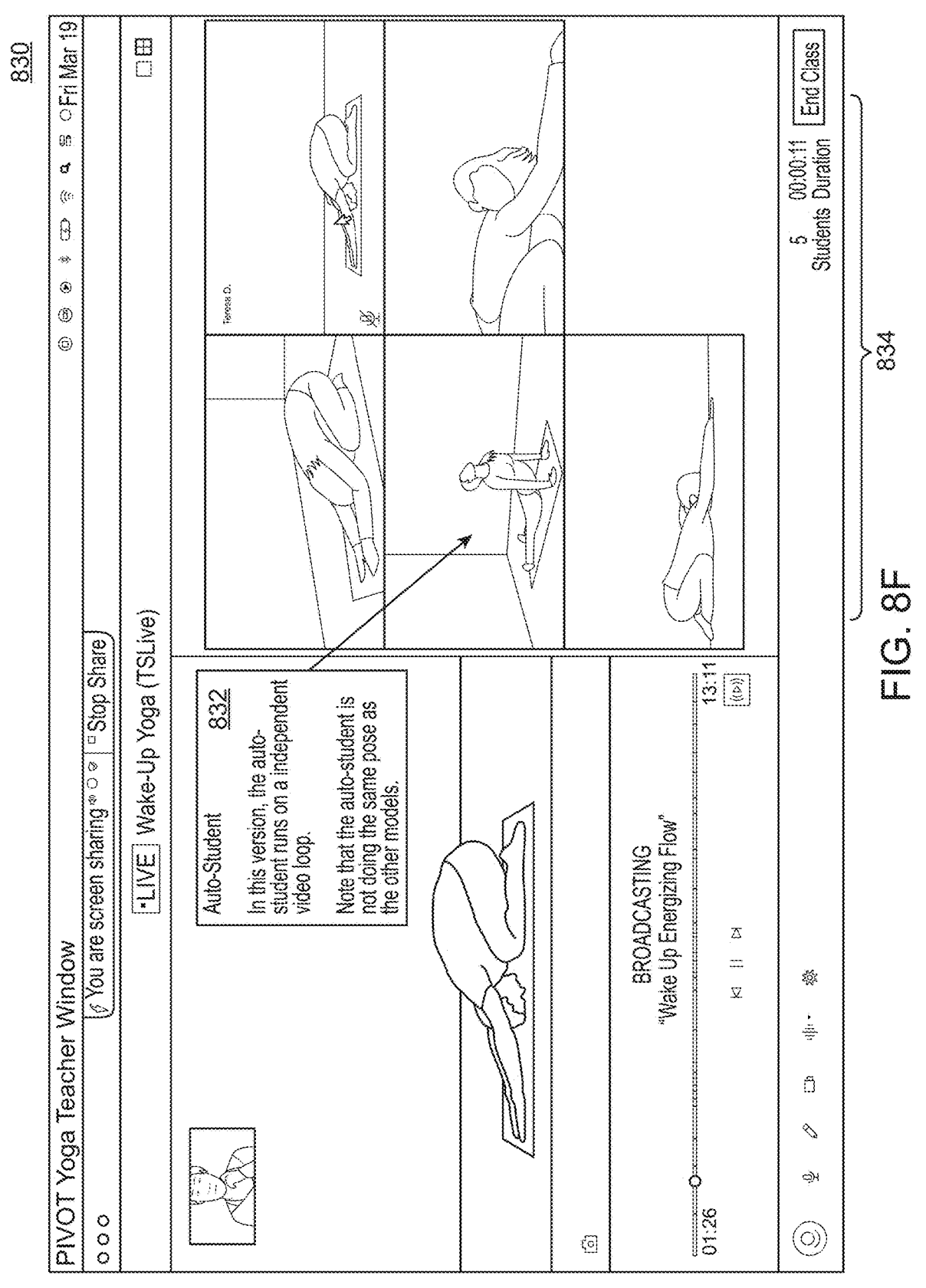

Referring now to FIG. 8F, it shows a view 830 by a teacher that includes what is referred herein as auto-student. It means that a student who is present in a class or session is not a real one. According to one embodiment, a prerecorded video of the student is played back in the session, where the video recorded pre-defined poses the student performed prior to the class. When the class is started, the video is inserted as if it appears that the student is actually in the session, performing similar motion with others. The video may be synched with other video streams as described above. A trainer may still use the avatar of a model (e.g., auto-student or skilled one) to show pose differences when compared to the same of a chosen student. According to another embodiment, the auto-student may act for an advertiser showing products or services that may be used by others in the class. For example, a seller of the garment 116 and 120 shown in FIG. 1C and FIG. 1D might have engaged a professional to wear the clothing to show how these gears would facilitate an interactive training session online with an instructor as if all were in one room. Those skilled in the art shall understood that products or services may be offered via this auto-student feature.

Figure 8G:
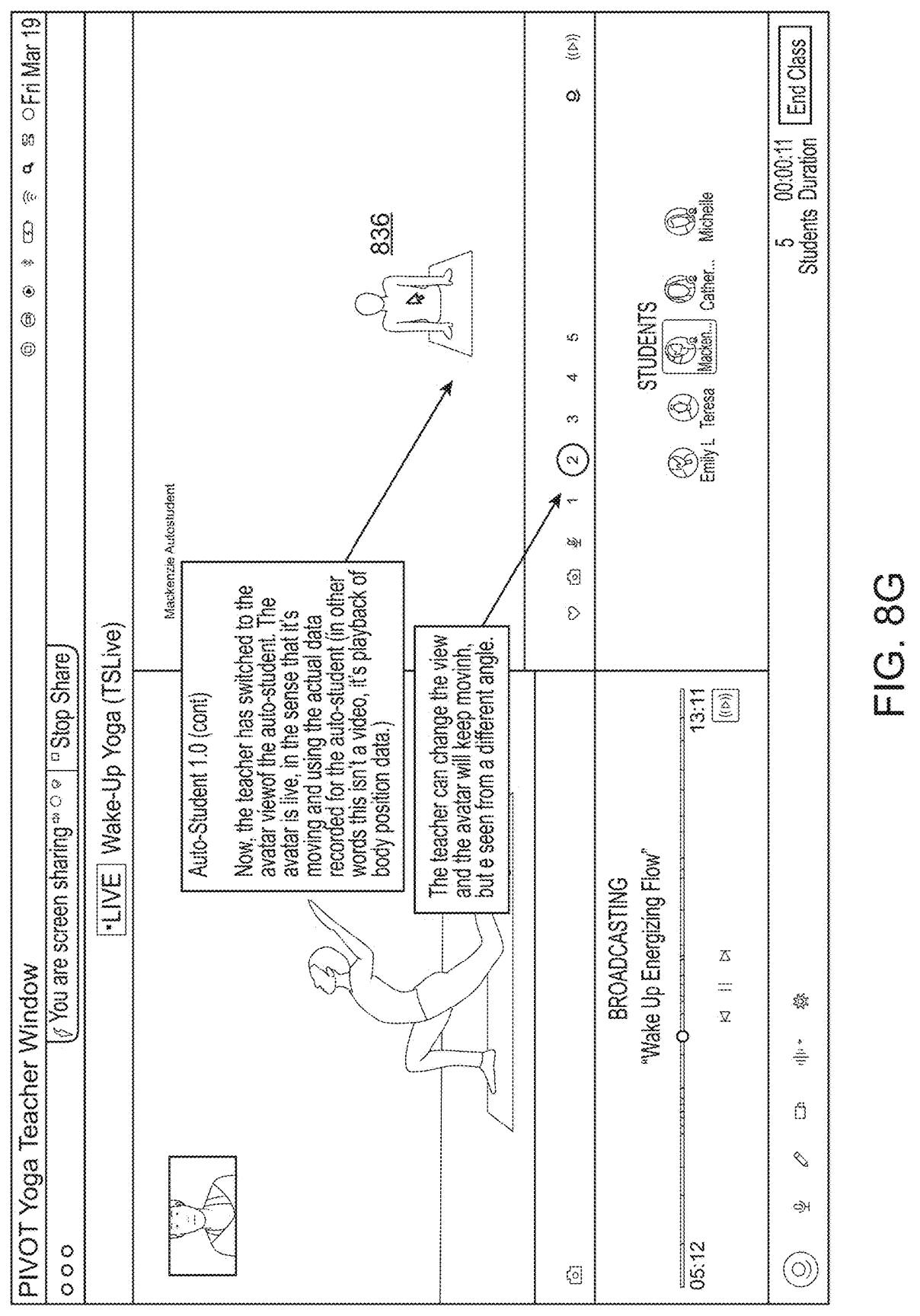

FIG. 8G shows the teacher has switched to the avatar view of the auto-student. The avatar 836 is live in the sense that it is moving and using the actual data recorded for the auto-student. It should be noted that the avatar being shown to perform is not from the video, it is a playback of body position data generated from the sensing data collected when the video is recorded. Like examining the motion performed by each of the students in the class, the instructor can view the avatar from any angle or share the same with one or all of the students in the class.

Figure 8H:
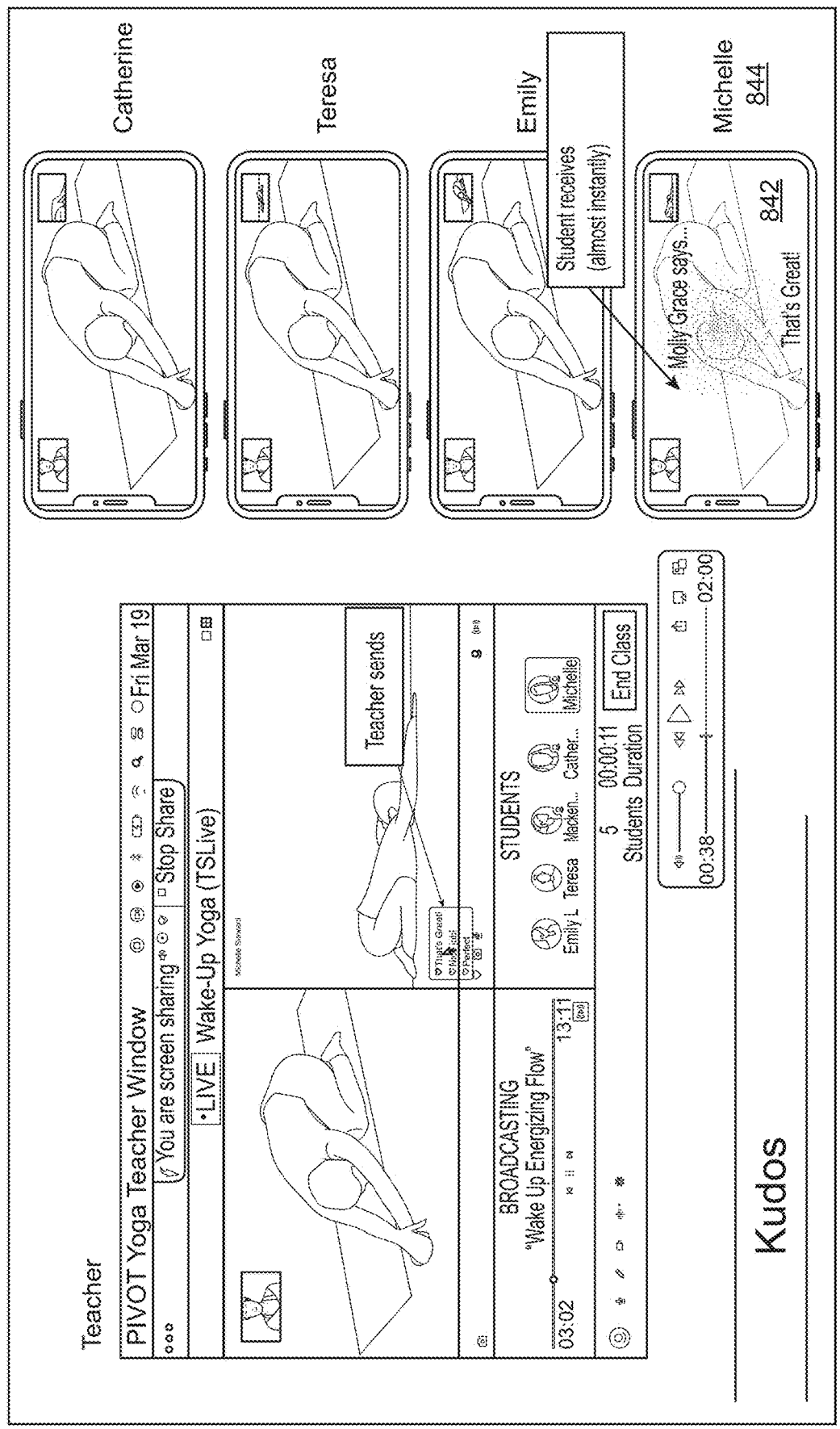
FIG. 8H shows that the teacher can send out pre-determined short messages to a particular student or all of the students.

FIG. 8H shows that the teacher can send out pre-determined short messages 840 to a particular student or all of the students. One example of such messages 842 is to encourage a tiring student 844. Another example of such messages is to instruct the entire class. The message is played along with an animation of digital symbols or signs (e.g., flowers) together with a sound effect on the student device. The fact that this kudo was sent, to whom, during what class, and during what pose, are all recorded and available for display to the teacher later after class is over.

Figure 8I:
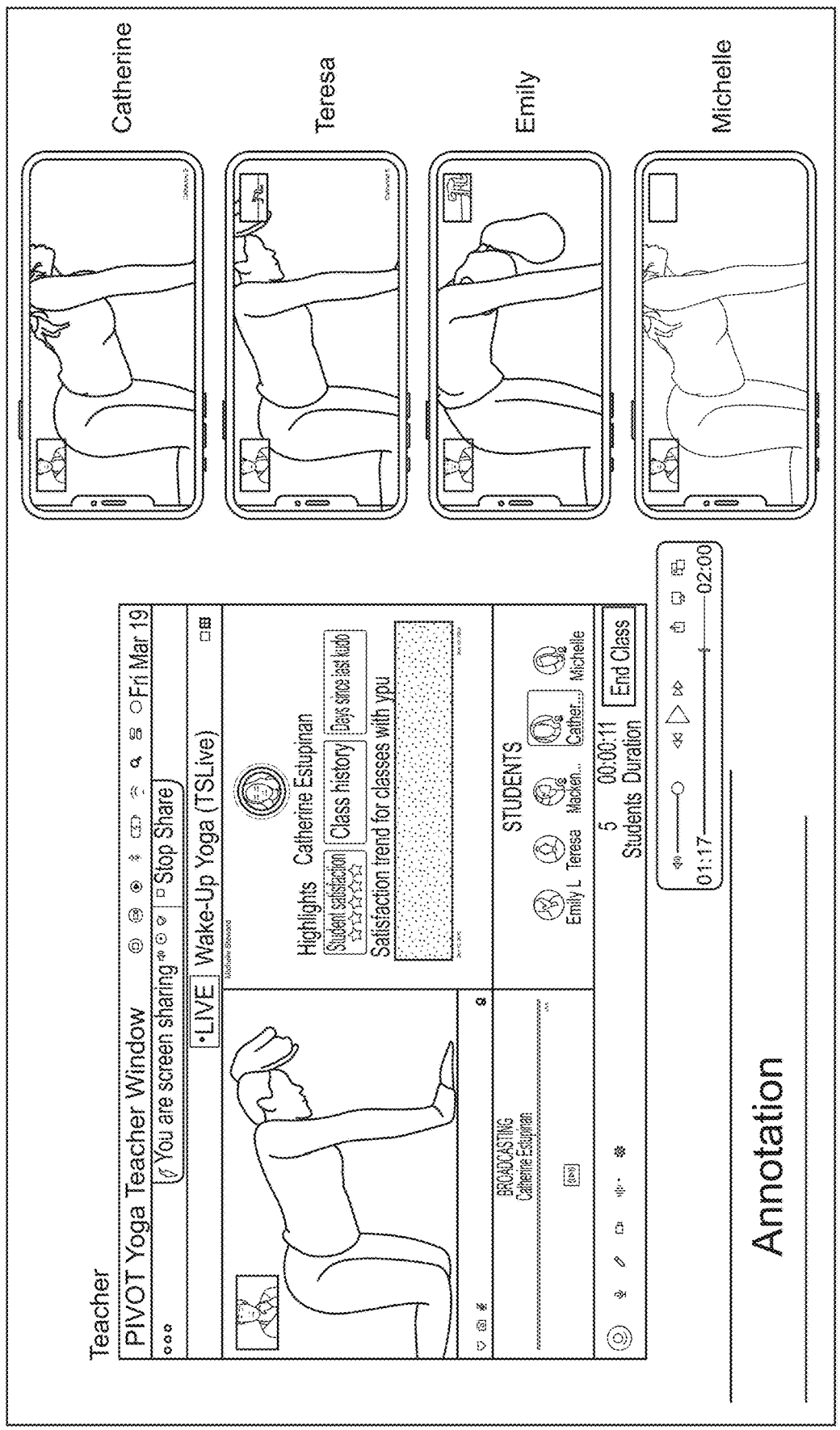
FIG. 8I shows a feature that allows a teacher to annotate directly on top of a moving video feed being shared and synched immediately with all the other students in the class.

Annotation in a shared space (e.g., a whiteboard) is common in many video applications. FIG. 8I shows a feature that allows a teacher to annotate directly on top of a moving video feed being shared and synched immediately with all the other students in the class. According to one embodiment, the teacher can annotate and broadcast on top of a student avatar feed as well.

Figure 8J:
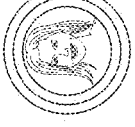
FIG. 8J shows an exemplary display of key metrics about a chosen student Sally Beasley.

While a teacher is rebroadcasting (i.e., sharing one student's video or avatar feed with the rest of the class), the teacher gets a heads-up display of key metrics about the student, including where he or she lives. FIG. 8J shows an exemplary display 850 of the key metrics about a chosen student Sally Beasley. The display 850 of the statistics about a student shows the progress the student has achieved through the past classes he or she has since joined. In other words, the platform as discussed herein performs continuously statistics for each of the students in predetermined aspects (e.g., match scores against an authoritative demonstrator or instructor, even if a student is never chosen by the teacher).

According to one embodiment, a live class is classified into three modes: Warm Up, Live, and Warm Down. The Warm Up session is designed to encourage students to get to know each other and to chitchat while the teacher checks their mat setups and etc. The Live session is when the yoga sequence starts, each or all performing under the instruction of the teacher. The Warm Down session is for more feedback, chitchat, and a chance for the teacher to discuss Highlights with the students. One of the features in the embodiment is the automatic switching of all student microphones On or Off depending on the mode of the class. In any case, a student can always ask to be unmuted if they have a question, and the teacher can unmute one or more students if needed.

Figure 8K:
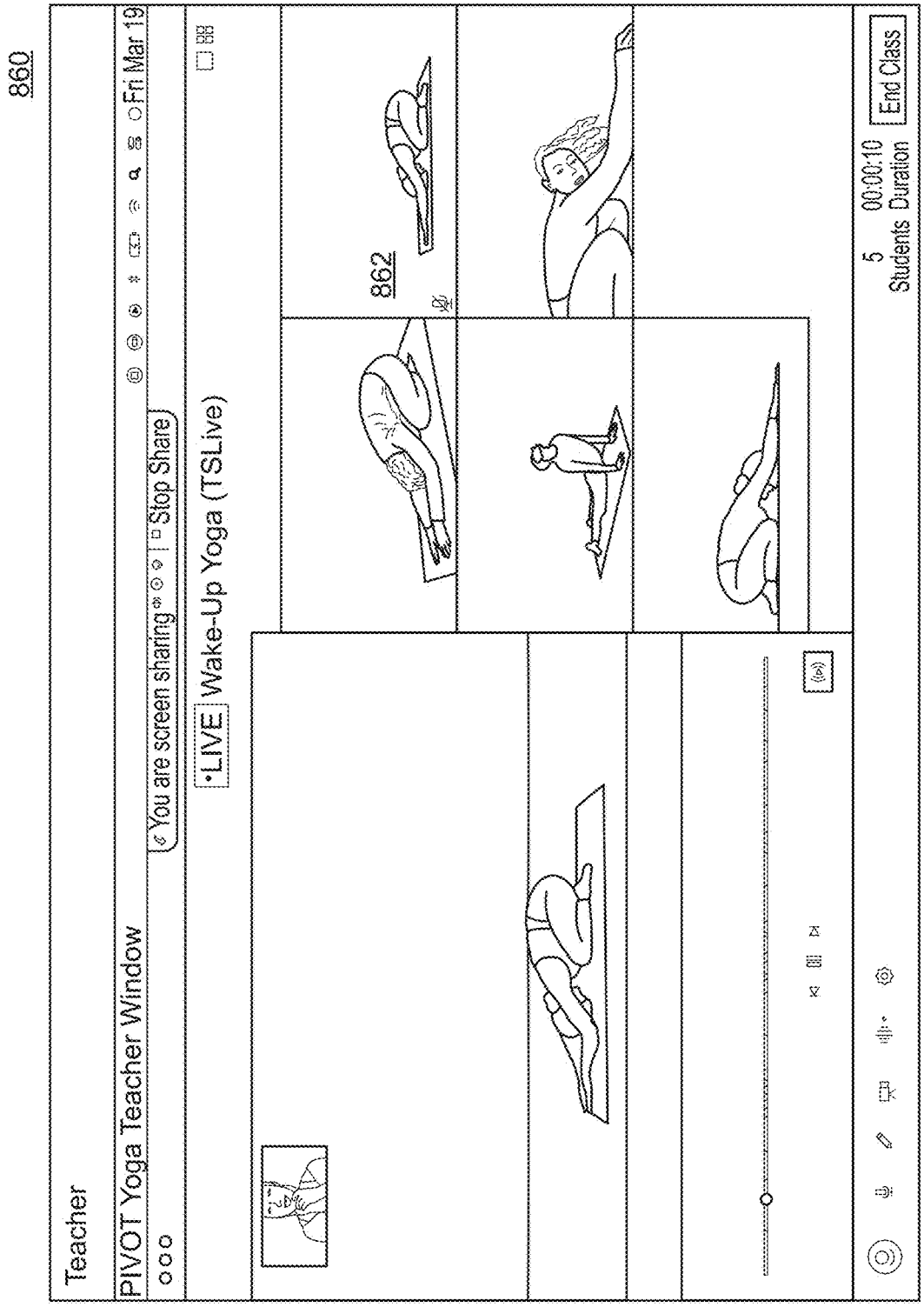
FIG. 8K shows a figure in which one of the students is muted (his mic is shown off)

FIG. 8K shows a FIG. 860 in which one of the students is muted (his mic 862 is shown off). In other words, the student can listen to what the teacher or other students are talking but no one can hear what he wants to say, unless he unmutes himself or is unmuted by the teacher. According to one embodiment, the mode of a class determines whether the students shall be muted to avoid possible distraction from others. In other words, when the class enters the live mode, all students are automatically muted. If one wants to speak, he can unmute himself. When the class enters the warm-up or warm-down mode, all students are automatically unmuted, everyone can hear everyone.

Figure 8L:
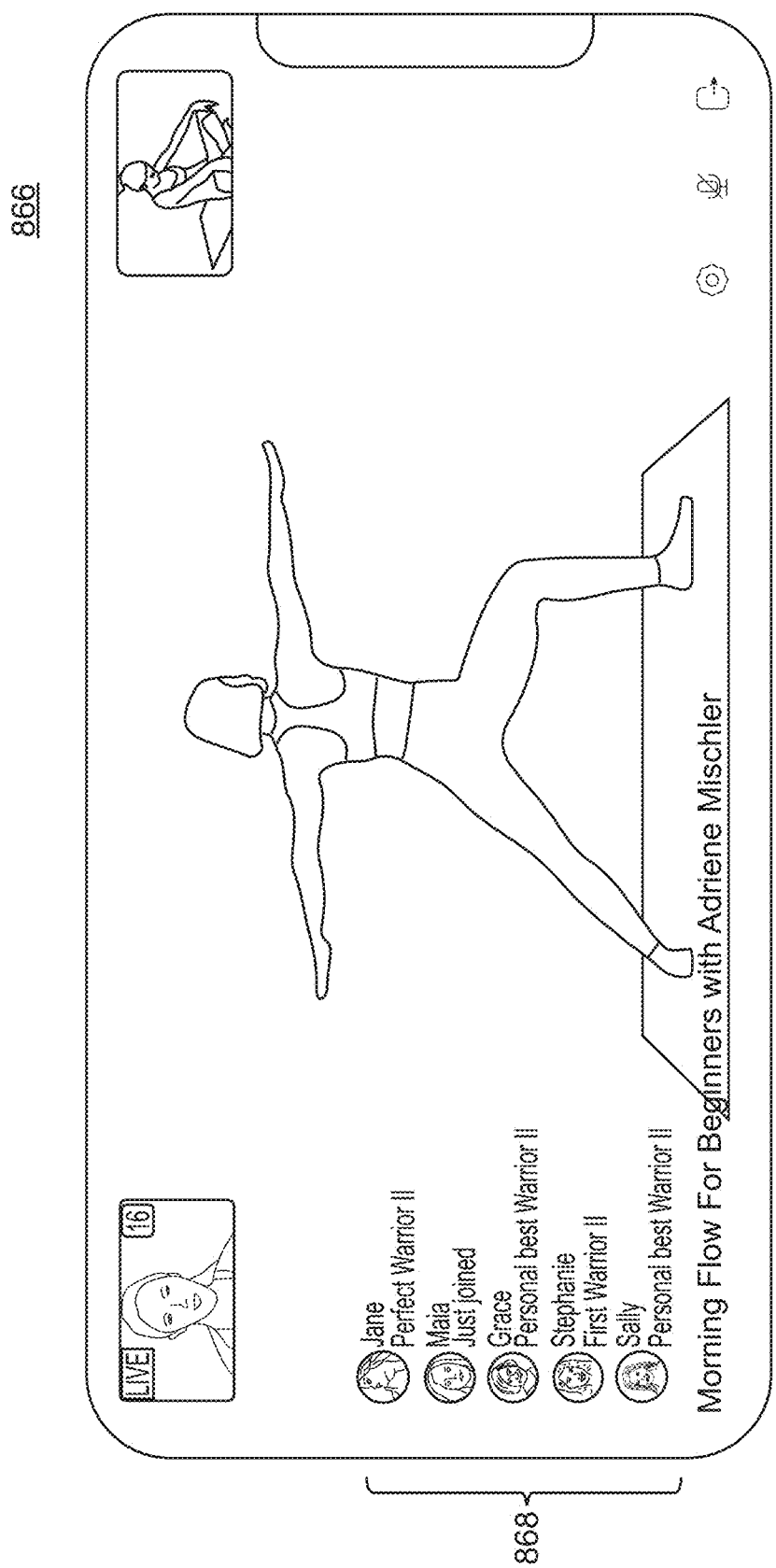
FIG. 8L shows a display on the side of a student, where student performance milestones are respectively shown, for example, the first time a student has ever done a pose, the first time a student has done a pose with the teacher, and their personal best in a pose.

Many live streaming products stream student comments, or exit/entrance, into the audience experience. FIG. 8L shows a display 866 on the side of a student, where student performance milestones 868 are respectively shown, for example, the first time a student has ever done a pose, the first time a student has done a pose with that teacher, their personal best in a pose, or even a particularly high match score on a pose. In operation, the platform as described herein keeps performing records of each student registered therein and participated in one or more classes, and their progresses with an instructor or a chosen authoritative model.

Figure 8M:
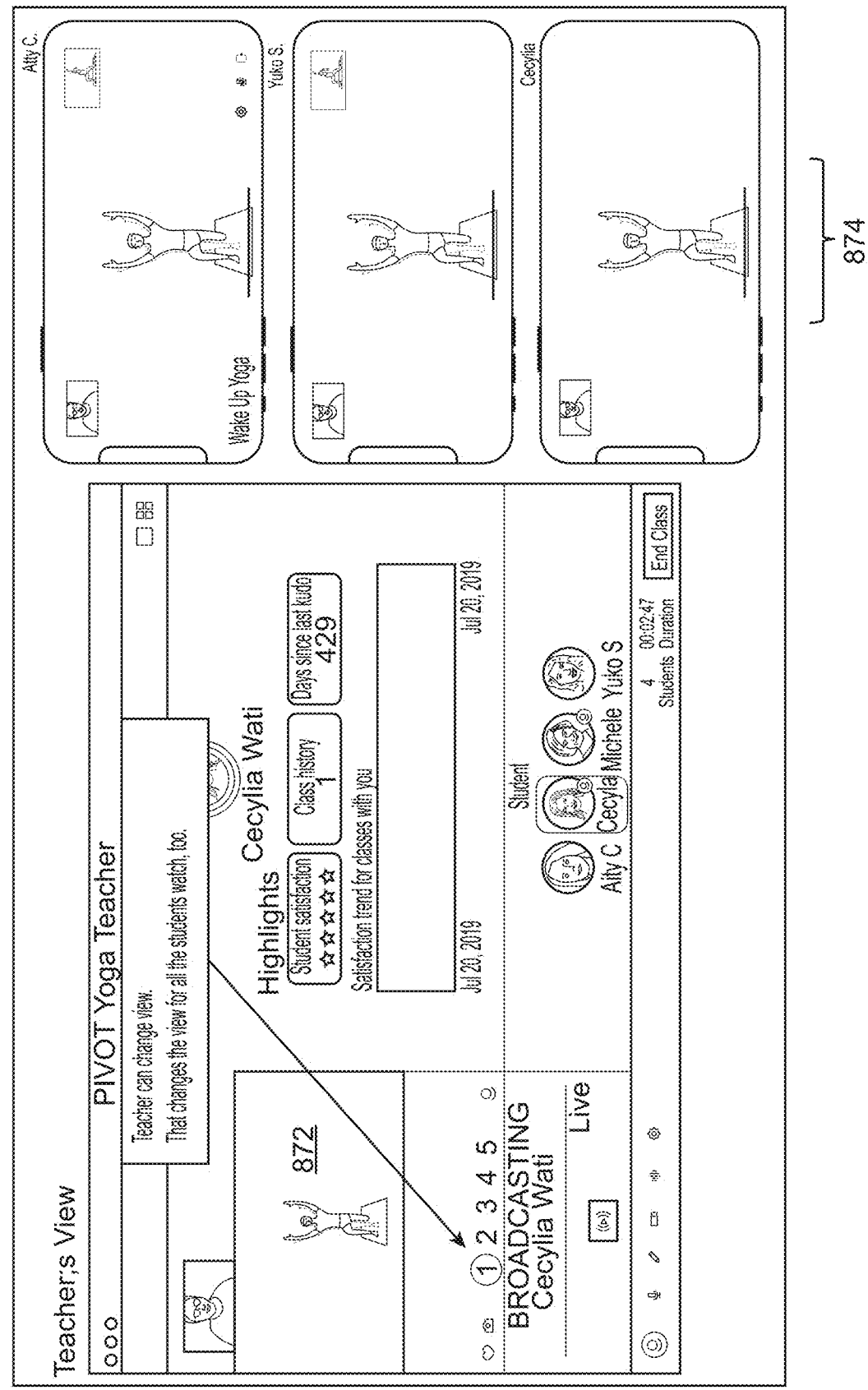
FIG. 8M shows an exemplary synched display of the avatar feed of one student to all other students.

Referring now to FIG. 8M, it shows an exemplary synched display 870 of the avatar feed of one student to all other students. Different from many prior art video products that share one video to all others, the display 870 shows that the avatar 872 of a student can be shared with all other students 874. In operation, a teacher can choose a perspective of the student, where the avatar 872 of the student in the perspective is generated and synched with the display of all other students. In other words, the shared screen is not a video from any of the feeding (e.g., from the cameras being used by the students), but a generated graphics that includes an avatar of a participant and/or an avatar of a model to allow the teacher to illustrate where the student may improve in view of the model.

According to one embodiment, when the teacher changes the view by clicking on one of the view numbers, the view updates for all the students as well. To do this live video streaming, a feature Texture Shader (within Unity 3D) is used to modify the video image stream and use texture memory as the alternate video source instead of the camera feed to broadcast the avatar view. The Teacher app simply sends the student id that needs to be zoomed in or shown in full screen to all Student apps. Each Student app then shows the video stream from that particular student in full screen.

Figure 8N:
FIG. 8N shows an exemplary display of records maintained by the platform for registered students and maybe accessed by authorized personnel (e.g., the teacher)

FIG. 8N shows an exemplary display of records maintained by the platform for registered students and maybe accessed by authorized personnel (e.g., the teacher). The records maintain individual accounts, each for one registered student. Besides keeping a profile for each student and other administrative data (e.g., name, DOB, fees and etc.), one embodiment of the present invention (e.g., the teacher APP) archives and updates all highlights related to a student in one place. For example, what class the student has participated, his matching scores to an identified instructor (avatar comparisons in respective perspectives), his progress and selected sessions of his classes along with his feedback to the teacher.

According to one embodiment, with a live feed at 50 Hz of a student body position, the maximum stillness of the student is calculated. Through pose titling in the teaching video, it can be inferred what pose the student is supposed to be doing. The platform keeps a library of reference avatar postures for all the poses according to an activity, where the references are updated and growing periodically. With a student wearing the clothes as shown in FIG. 1C and FIG. 1D and doing a yoga sequence in view of a chosen instructor from the library, a Match Score is calculated for each pose by the student. For each of the major body parts being tracked via the sensor modules (e.g., 16 of them), the XYZ delta between the student avatar position and the reference avatar pose position as well as a reference pose at a particular body part, and score it as a 1 or a 0, allowing for a tolerance level. In one embodiment, the scores are summed and divided by 16 to find their Match Score for the pose. By an analogous piece of math, the Match Score for the student entire class performance can be calculated. Optionally, the Match Score for all the students in the class can be calculated. This Match Score is tracked historically and can be displayed on a trend chart. We also mark a student as having reached an Intermediate or Advanced status once his Match Score across all (or a set of poses predesignated) reaches a threshold level. FIG. 8O shows an exemplary snapshot of a student for a predefined period (e.g., last 12 weeks).

Figure 8P:
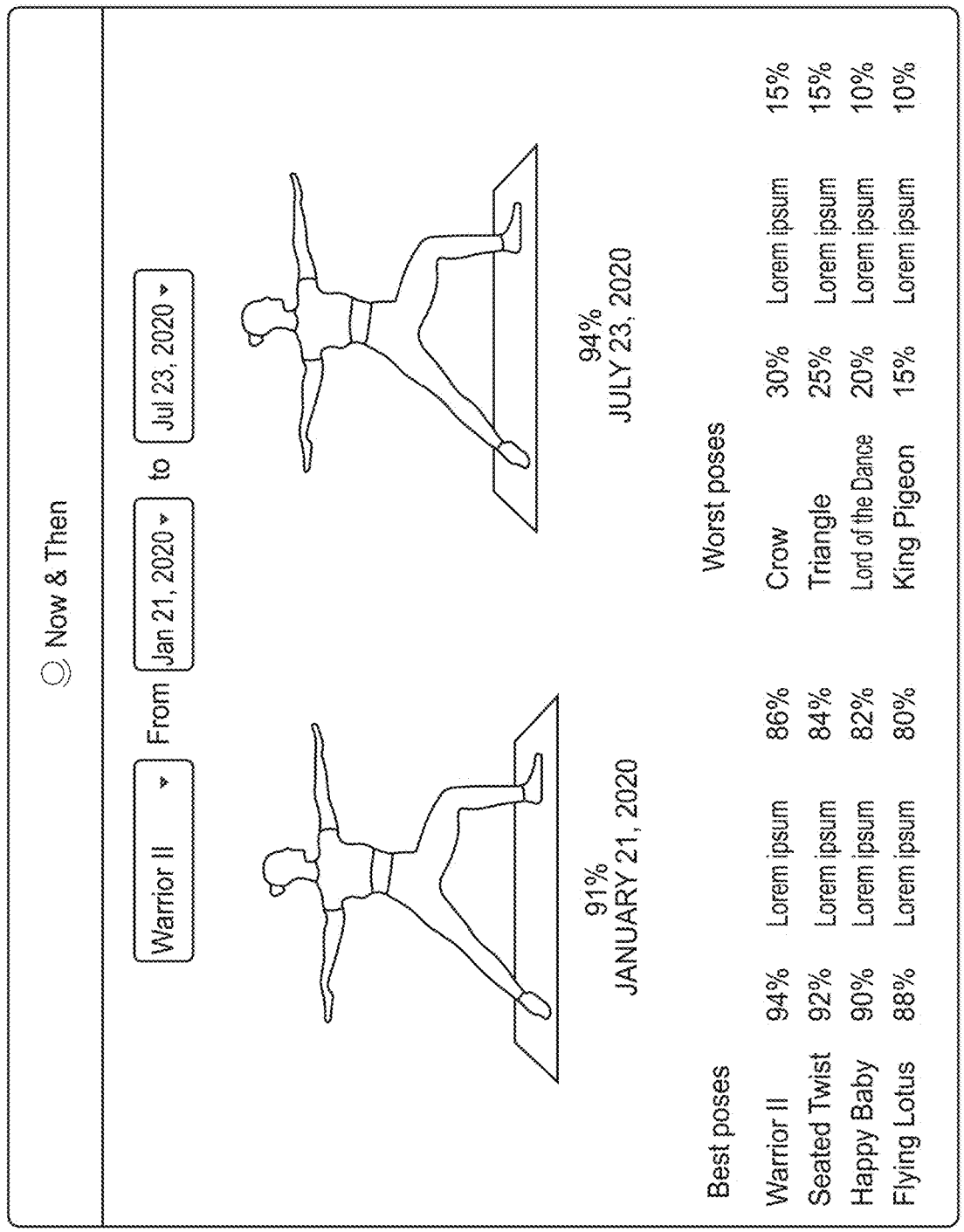
FIG. 8P shows an example of tracking and displaying evolution of student performance on a single given pose.

FIG. 8P shows an example of tracking and displaying evolution of student performance on a single given pose. Aside from the Match Score tracking in above, the joint angles of the student at every point of maximum stillness in all the titled poses in a yoga sequence are also archived. Each set of data is dated, so that the teacher (and the student, in the student app) can pick a pose of interest and compare two points in time of his performance of that pose.

Figure 8Q:
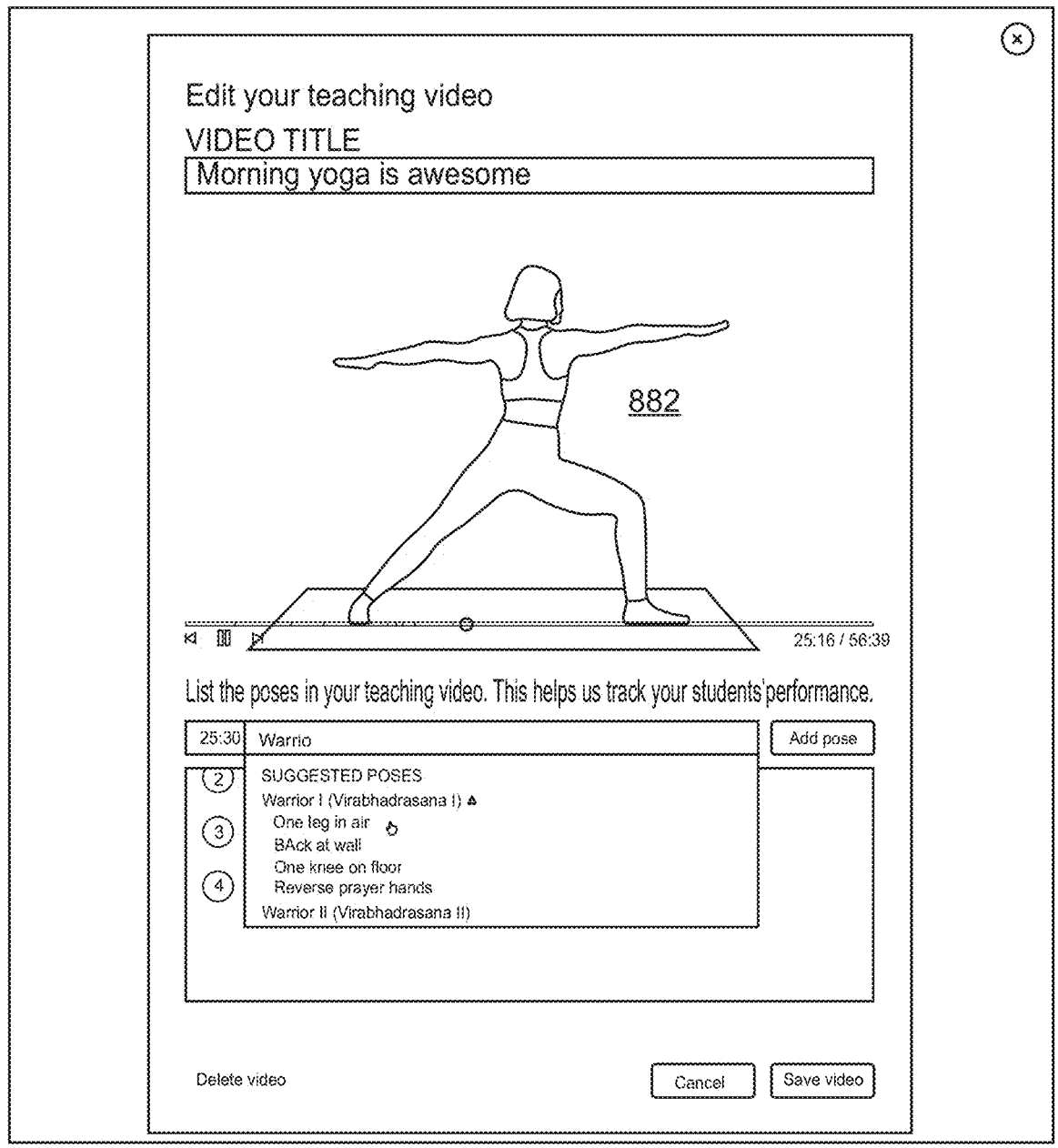
FIG. 8Q shows an example in one embodiment in which a teacher is allowed to add his comments to a pose by a student.

FIG. 8Q shows an example 880 in one embodiment in which a teacher is allowed to add his comments to a pose by a student. Such comments may be reviewed later by the student to improve his pose. The comments may be associated with a section of video that can be specifically titled and time stamped (saved with the metadata). The video can be played back to see how the student 882 was performing. The student can improve his pose based on the comments in his leisure time when needed. A pose definition with 3D reference avatar pose images can be displayed to the teacher/user to disambiguate when a pose name is not clear or has multiple name/pose variations. Then, once the pose names are inserted, they are written to the metadata for the video and in turn, when the video is run inside a class as a teaching video, the Pose Titles are displayed automatically to students and teachers based on the metadata. (The pose titles also function as chapter markers, in the sense that the teacher can skip forward and backward between pose titles in the video. Optionally, the student 882 can be viewed in an avatar anytime to compare with an avatar of an instructor for comparison and matching score.

Figure 8R:
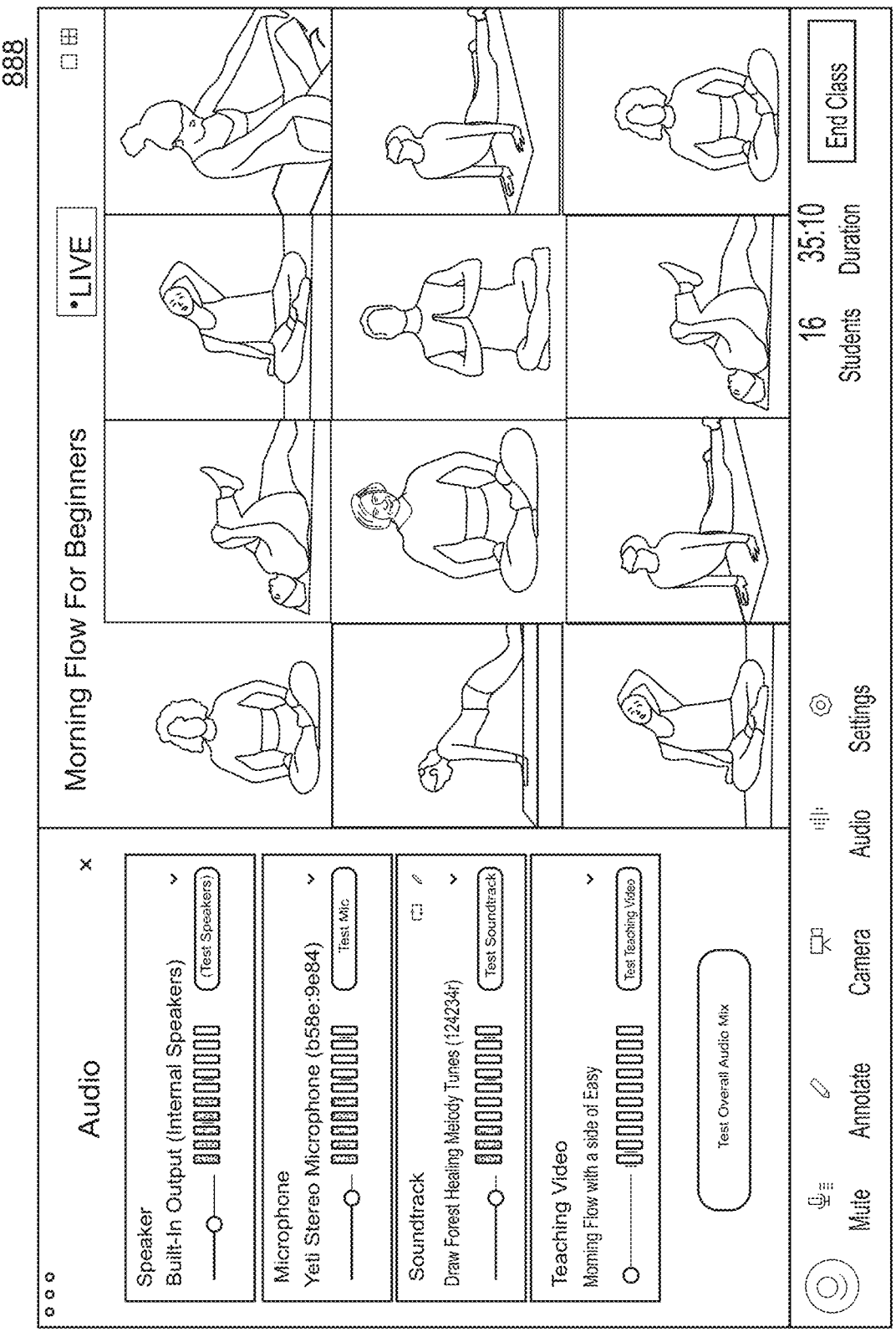
FIG. 8R shows an example to allow a teacher to have a full audio control including managing teaching video and soundtracks, including the microphone, the speaker, the teaching video itself, and any soundtrack that they upload.

FIG. 8R shows an example 88 to allow a teacher to have a full audio control including managing teaching video and soundtracks, including the microphone, the speaker, the teaching video itself, and any soundtrack that they upload. Those levels can also be tested individually, and then the teacher can test the entire audio mix at once.

The platform, the applications (teacher App or student App) or the algorithms described above are preferably implemented in software, but can also be implemented in hardware or a combination of hardware and software. The implementation of these can also be embodied as computer readable code on a computer readable medium. The computer readable medium is any data storage device that can store data which can thereafter be read by a processor or a computer system. Examples of the computer readable medium include read-only memory, random-access memory, CD-ROMs, DVDs, magnetic tape, optical data storage devices, and carrier waves. The computer readable medium can also be distributed over network-coupled computer systems so that the computer readable code is stored and executed in a distributed fashion.

The present invention has been described in sufficient detail with a certain degree of particularity. It is understood to those skilled in the art that the present disclosure of embodiments has been made by way of examples only and that numerous changes in the arrangement and combination of parts may be resorted without departing from the spirit and scope of the invention as claimed. While the embodiments discussed herein may appear to include some limitations as to the presentation of the information units, in terms of the format and arrangement, the invention has applicability well beyond such embodiment, which can be appreciated by those skilled in the art. Accordingly, the scope of the present invention is defined by the appended claims rather than the forgoing description of embodiments.

We claim:

1. A method for instructing a class online, the method comprising:
   receiving in a control computer data streams from computing devices respectively associated with students performing poses in accordance with a predefined activity, wherein each of the streams includes sensing data from a plurality of sensor modules disposed respectively to designated body parts of a student;
   deriving in the control computer attributes from the sensing data to generate an avatar of the student;
   displaying the avatar in a chosen perspective while the student performs the poses, wherein the avatar moves in accordance with the poses the student performs; and
   sharing with others a display of the student along with the avatar, wherein said sharing with others a display of the student comprises:
   displaying on the control computer a heads-up display of key metrics about the student, wherein the heads-up display is not shared with others.

2. The method as recited in claim 1, further comprising:
   displaying a reference avatar to allow a viewer to associate the reference avatar with the student along with a score to illustrate how close the student performs a pose when compared with the reference avatar.

3. The method as recited in claim 2, wherein the score is a numerical number between zero to indicate a total mismatch and a predefined maximum number to indicate a perfect match.

4. The method as recited in claim 2, wherein the reference avatar is one of reference avatars maintained in a library periodically updated or growing.

5. The method as recited in claim 1, wherein said sharing with the students a display of the student along with the avatar comprises:
   displaying a reference avatar of a model to allow a viewer to visualize any differences of the student and the model both performing the poses.

6. The method as recited in claim 5, further comprising:
   calculating a matching score between the model and student; and
   displaying the matching score in real time.

7. The method as recited in claim 5, wherein said displaying the avatar in a chosen perspective is on the control computer or a different computer.

8. The method as recited in claim 1, wherein the student wears a set of clothing embedded with the sensor modules, the sensors are respectively affixed to predefined areas of the clothing and captures motions of the designated body parts of the student.

9. The method as recited in claim 8, wherein at least one of the sensor modules sends out to a computing device the sensing data generated therein.

10. The method as recited in claim 9, wherein each of the sensor modules including at least an inertial sensor and a transceiver for intercommunication with a hub module or a computing device.

11. The method as recited in claim 1, wherein the control computer is used by a teacher and remotely located with respect to the plurality of computing devices, and the method further comprising:
controlling from the control computer displays on the computing devices, wherein the displays are synchronized with the control computer, the control computer is configured to send out a periodic heartbeat to the computing devices to facilitate synchronization of the displays.

12. The method as recited in claim 11, further comprising:
allowing a teacher to choose a kudo from a list to encourage the student to keep doing what the student is doing; and
archiving highlighted sections of the student performing the poses, wherein at least one of the highlighted sections includes the avatar of the student, and an avatar of a model to allow a viewer to visualize any differences of the student and the model both performing the poses.

13. The method as recited in claim 11, wherein the control computer is configured to send out automatically a command to the plurality of computing device in synchronization of a mode of the class.

14. The method as recited in claim 13, wherein the command includes data to mute or unmute the computing devices being used by the students.

15. The method as recited in claim 1, wherein each of the computing devices includes a camera but there is no requirement how each of computing devices is positioned with respect to a corresponding student.

16. The method as recited in claim 15, wherein said deriving attributes from the sensing data to generate an avatar of the student does not use any data from the camera.

17. A computer comprising:
a display screen;
a memory space for storing code;
a processor, coupled to the memory space, executing the code to cause the computer to perform operations of:
receiving streams from computing devices remotely located and respectively associated with students performing poses in accordance with a predefined activity, wherein each of the streams includes sensing data from a plurality of sensor modules disposed respectively to designated body parts of a student;
deriving motion analysis attributes of the student from the sensing data generating a display in the control computer to show how the student performs the poses in a chosen perspective based on the analysis attributes; and
sharing the display with others, wherein said sharing the display with others comprises:
displaying on the control computer a heads-up display of key metrics about the student, wherein the heads-up display is not shared with others.

18. The computer as recited in claim 17, wherein the student wears a set of clothing embedded with the sensor modules, the sensors are respectively affixed to predefined areas of the clothing and captures motions of the designated body parts of the student.

19. The computer as recited in claim 17, wherein the sensor modules generate individually the sensing data when the student performs the poses, and transporting wirelessly to a computing device the sensing data.

20. The computer as recited in claim 17, wherein the operations further comprise:
displaying on the display screen a video of the student along with an avatar generated from the motion analysis attributes to allow a viewer to associate the avatar with the student.

* * * * *